US 9,657,014 B2

(12) United States Patent
Ceccarelli et al.

(10) Patent No.: US 9,657,014 B2
(45) Date of Patent: May 23, 2017

(54) SUBSTITUTED 1,6-NAPHTHYRIDINES

(71) Applicant: Hoffmann-La Roche Inc., Little Falls, NJ (US)

(72) Inventors: Simona M. Ceccarelli, Basel (CH); Ravi Jagasia, Loerrach (DE); Roland Jakob-Roetne, Inzlingen (DE); Rainer E. Martin, Basel (CH); Jens-Uwe Peters, Grenzach-Wyhlen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/717,109

(22) Filed: May 20, 2015

(65) Prior Publication Data

US 2015/0252044 A1   Sep. 10, 2015

Related U.S. Application Data

(63) Continuation of application No. PCT/EP2013/074012, filed on Nov. 18, 2013.

(30) Foreign Application Priority Data

Nov. 20, 2012  (EP) .................................... 12193311

(51) Int. Cl.
| | | |
|---|---|---|
| A61K 31/4375 | (2006.01) | |
| C07D 471/04 | (2006.01) | |
| A61K 31/444 | (2006.01) | |
| A61K 31/496 | (2006.01) | |
| A61K 31/506 | (2006.01) | |
| A61K 31/5377 | (2006.01) | |
| A61K 31/541 | (2006.01) | |

(52) U.S. Cl.
CPC ........ *C07D 471/04* (2013.01); *A61K 31/4375* (2013.01); *A61K 31/444* (2013.01); *A61K 31/496* (2013.01); *A61K 31/506* (2013.01); *A61K 31/5377* (2013.01); *A61K 31/541* (2013.01)

(58) Field of Classification Search
USPC .......................................... 514/300; 546/122
See application file for complete search history.

(56) References Cited

U.S. PATENT DOCUMENTS

| | | | | |
|---|---|---|---|---|
| 6,534,520 B2 * | 3/2003 | Bedard | ................ | C07D 513/04 514/301 |
| 7,282,506 B2 * | 10/2007 | Hanson | ................ | C07D 471/04 514/300 |
| 8,685,981 B2 * | 4/2014 | Kanno | ................ | C07D 217/22 514/217.07 |

FOREIGN PATENT DOCUMENTS

| | | |
|---|---|---|
| EP | 2380878 | 10/2011 |
| EP | 2418203 | 2/2012 |
| WO | 2008/046072 | 4/2008 |
| WO | 2010/101949 | 9/2010 |

OTHER PUBLICATIONS

International Search Report and Written Opinion for International Patent Application No. PCT, mailed on Dec. 2, 2014, 6 pages.
Isenmann et al., "Molecular determinants of retinal ganglion cell development, survival, and regeneration" *Science Direct* 22:483-543 (2003).
Izumikawa et al., "Auditory hair cell replacement and hearing improvement by Atoh1 gene therapy in deaf mammals" *Nature Medicine* 11 (2005).
Kraus et al., "Noise Trauma Impairs Neurogenesis in the Rat Hippocampus" *Neuroscience*:1216-1226 (2010).
Landa et al., "Weekly Vaccination with Copaxone (Glatiramer acetate) as a Potential Therapy for Dry Age-Related Macular Degeneration" *Current Eye Research* (2008).
Libert et al., "Neurogenesis directed by Sirt1" *National Institute of Health*:373-374 (2008).
Ming et al., "Adult Neurogenesis in Mammalian Brain: Significant Answers and Significant Questions" *Neuron*:687-702 (2011).
Sahay et al., "Pattern Separation: A Common Function for New Neurons in Hippocampus and Olfactory Bulb" *Neuron*:582-588 (2011).
Tiberi et al., "BCL6 controls neurogenesis through Sirt1-dependent epigenetic repression of selective Notch targets" *Nature Neuroscience* 15:1627-1635 (2012).

* cited by examiner

*Primary Examiner* — Charanjit Aulakh

(57) ABSTRACT

The present invention relates to the use of compounds of general formula I wherein R', $R^1$, $R^2$ and $R^3$ are as defined herein, or to a pharmaceutically acceptable acid addition salt, to a racemic mixture or to its corresponding enantiomer and/or optical isomers thereof, and for methods to treat a variety of neurodegenerative and neuropsychiatric diseases.

4 Claims, No Drawings

SUBSTITUTED 1,6-NAPHTHYRIDINES

The present invention relates to the use of compounds of general formula

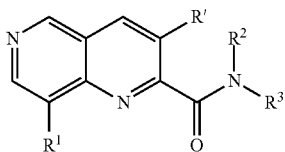

wherein
R' is hydrogen or lower alkyl;
$R^1$ is halogen, lower alkyl, cycloalkyl or cyano; or
  is phenyl, optionally substituted by one to three substituents, selected from lower alkyl, lower alkyl substituted by halogen, lower alkoxy, lower alkoxy substituted by halogen, halogen, cyano, hydroxy, C(O)—NH-lower alkyl, $CH_2$—C(O)—NH-lower alkyl, $CH_2$—NH—C(O)-lower alkyl, $CH_2NH_2$, $S(O)_2CH_3$, $S(O)_2N(CH_3)_2$, or by heterocycloalkyl groups; or
  is pyrazol-1, 4 or 5-yl, optionally substituted by lower alkyl; or
  is thiazol-5-yl, optionally substituted by one or two lower alkyl groups; or
  is pyridine 2, 3 or 4-yl, optionally substituted by lower alkyl, lower alkoxy, halogen or $N(CH_3)_2$; or
  is 3,6-dihydro-2H-pyran; or
  is benzo[d][1,3]dioxol-5-yl; or
  is 2,3-dihydrobenzo[b][1,4]dioxin-6-yl;
$R^2$ is hydrogen, lower alkyl or lower alkyl substituted by alkoxy;
$R^3$ is hydrogen, lower alkyl, lower alkyl substituted by halogen, lower alkyl substituted by hydroxy, NH—$S(O)_2$—$CH_3$, —$(CH_2)_m$—O-lower alkyl or —$(CH_2)_n$—$S(O)_2$—$CH_3$; or
  is —$(CR_2)_n$-phenyl, optionally substituted by —$S(O)_2CH_3$ or lower alkoxy; or
  is —$(CH_2)_n$-heterocycloalkyl, optionally substituted by lower alkyl and =O; or
  is —$(CH_2)_n$-heteroaryl, optionally substituted by one or two lower alkyl groups; or
  is —$(CH_2)_n$-cycloalkyl, optionally substituted by cyano;
or $R^2$ and $R^3$ form together with the N atom to which they are attached a heterocyclic ring, selected from morpholine, piperidine, 1,1-dioxo-thiomorpholine or piperazine which may be substituted by lower alkyl or C(O)O-lower alkyl, or may form a pyrrolidine ring, optionally substituted by hydroxy;
R is independently from n hydrogen or lower alkyl;
n is 0, 1, 2, 3;
m is 2;
or to a pharmaceutically acceptable acid addition salt, to a racemic mixture or to its corresponding enantiomer and/or optical isomers thereof,
for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuroactive drugs, such as alcohol, opiates, methamphetamine, phencyclidine or cocaine.

In the literature are described 1,6-naphthyridine derivatives for use
  in a pharmaceutical composition for stimulating bone acceleration for improving bone metabolism (JP2012036168 A),
  to treat cancer, inflammation, arthritis and angiogenesis (US2006030584),
  to treat diseases associated with bone metabolism, preferably osteoporosis (WO2010082563),
  to treat insulin resistance, metabolic syndrome and diabetes (WO2010101949),
  to treat accelerating bone formation, improving bone metabolism, and osteoporosis (WO2010116915),
  to treat infections in chemotherapy or organ transplant or AIDS (WO9734894),
  to treat virus infections (Journal of Medicinal Chemistry, 1999, 42(16), 3023-3025),
  to treat cancer, inflammatory disorders, immunological disorders, diabetes or obesity (WO2008036308),
  to treat melanoma (WO2008012782),
  to treat viral infections caused by herpes simplex virus and others (WO02051413).

Now it has been shown that the present compounds stimulate neurogenesis from neural stem cells (NSCs). Neurogenesis occurs in the developing and adult brain. Conceptually, this process of neurogenesis can be divided into four steps: (i) proliferation of NSCs; (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyrus of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyrus, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

The stimulation of adult neurogenesis represents also a therapeutic target for optic neuropathy (S. Isenmann, A. Kretz, A. Cellerino, Progress in Retinal and Eye Research, 22, (2003) 483) and macular degeneration (G. Landa, O. Butovsky, J. Shoshani, M. Schwartz, A. Pollack, Current Eye Research 33, (2008) 1011).

Hence, chemical stimulation of adult neurogenesis offers new regenerative avenues and opportunities to develop novel drugs for treating neurological diseases and neuropsychiatric disorders.

Therefore, the object of the present invention was to identify compounds that modulate neurogenesis. It has been found that the compounds of formula I are active in this area and they may therefore be used for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine.

The most preferred indications for compounds of formula I are Alzheimer's disease, depression, anxiety disorders and stroke.

The present invention relates to specific novel compounds of formula I, to the processes for their production, as well as to the use of compound of formula I in the treatment or prevention of disorders, relating to neurogenesis, in the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine and to pharmaceutical compositions containing the novel compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, and isopropyl.

The term "alkoxy" denotes a group —O—R' wherein R' is lower alkyl as defined above. The term "lower alkyl substituted by hydroxy" is an alkyl group as defined above, wherein at least one hydrogen atom is replaced by a hydroxy group. The preferred group is $CH_2OH$, $CH_2CH_2OH$ or $CH(CH_3)C(CH_3)_2OH$.

The term "lower alkyl substituted by halogen" denotes a lower alkyl group as defined above, wherein at least one hydrogen atom is replaced by a halogen atom. The preferred group is $CF_3$.

The term "lower alkoxy substituted by halogen" denotes a lower alkoxy group as defined above, wherein at least one hydrogen atom is replaced by a halogen atom. The preferred groups are $OCF_3$ and $OCH_2CF_3$.

The term "heterocycloalkyl" comprises non aromatic rings, containing at least one heteroatom, selected from N, O or S. Such groups are piperidinyl, morpholinyl, pyrrolidinyl, piperazinyl or 1,1-di-oxo-thiomorpholinyl.

The term "heteroaryl" comprises aromatic rings, containing at least one heteroatom, selected from N, O or S. Such groups are pyridinyl, imidazolyl, pyrazolyl, pyrazinyl, pyrimidinyl or, thiazolyl.

The term "halogen" denotes chlorine, bromine, fluorine or iodine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention is the use of a compound of formula I for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine, for example the compounds listed in Tables 1 and 2.

One embodiment of the invention are specific novel compounds falling into the scope of formula I, this compounds are listed in Table 1.

One embodiment of the invention are novel compounds falling into the scope of formula I for use as therapeutically active substances. These compounds are listed in Table 1.

One embodiment of the invention are novel compounds falling into the scope of formula I for use in the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine, which compounds are listed in Table 1.

One further embodiment of the invention is a pharmaceutical composition comprising a novel compound falling into the scope of formula I, which compounds are listed in Table 1.

One embodiment of the present invention is the use of a compound of formula I for the preparation of medicaments for the therapeutic and/or prophylactic treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine, which compounds are listed in Tables 1 and 2.

A further embodiment of the invention is a method for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine, which method comprises administering an effective amount of a compound of formula I, for example compounds disclosed in Tables 1 and 2.

The present new compounds of formula I and their pharmaceutically acceptable salts can be prepared by methods known in the art, for example, by processes described below, which process comprises a) reacting a compound of formula

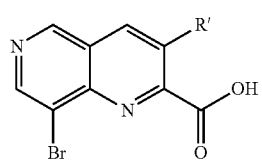

I with a compound of formula $NHR^2R^3$      2 to a compound of formula

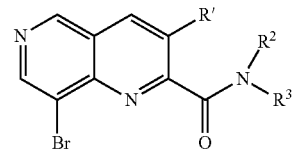

I-1 and, if desired, converting the compounds obtained into pharmaceutically acceptable acid addition salts, or b) reacting a compound of formula I-1

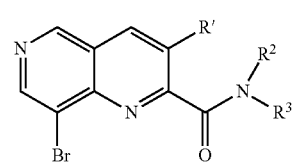

I-1 with a compound of formula

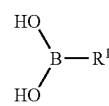

3 to a compound of formula

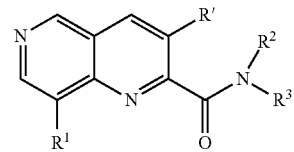

I and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

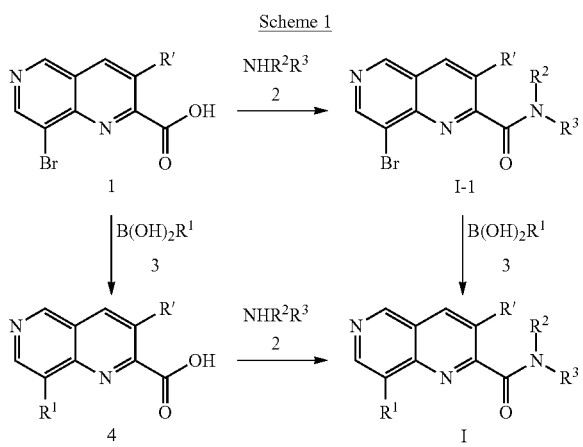

Scheme 1

A mixture of 8-bromo-1,6-naphthyridine-2-carboxylic acid of formula 1, N,N-diisopropylethylamine and O-(7-azabenzotriazol-1-yl)-N,N,N',N'-tetramethyluronium hexafluorophosphate (HATU) in dimethylformamide is stirred at room temperature for 10 minutes. The corresponding amine of formula 2 is added and stirring is continued over two day to yield a compound of formula I-1.

Furthermore, to a suspension of 8-bromo-N-(2-methoxyethyl)-1,6-naphthyridine-2-carboxamide of formula I-1 and a boronic acid of formula 3 and cesium carbonate in dioxane and water is added bis(diphenylphosphino)ferrocene-palladium(II)dichloride. The mixture is stirred at 80° C. for 3 hours. Removal of the solvent by distillation and chromatography yields the compound of formula I.

Amide bond formation reactions can be conducted using either batch or by employing continuous mode (flow) reaction protocols. Continuous mode synthesis is conducted using a custom-made, integrated flow synthesis and preparative HPLC purification system. A commercial R4 flow reactor module from Vapourtec is connected to a preparative HPLC purification system that is assembled from of a Gilson LH 215 auto-sampler, two Gilson 819 injection modules, two Agilent 1100 Series pumps, one Agilent 1200 series DADA detector, two Varian prep star pumps, one Dionex UV detector, one Polymer Laboratory light-scattering detector and one Dionex P-680 pump. Reagents and starting materials are injected via the LH 215 auto-sampler onto the flow reactor reagent loops (Gilson 819 injection modules) and from there onto the PFA (perfluoroalkoxy polymer) tube reactor coil (10 mL) fitted with a 100 psi back pressure regulator (BPR). In order to limit dispersion effects and to maintain a consistent concentration within the reaction zone as it progresses through the flow reactor, small air bubbles are injected before and after the reaction segment. After completion of the flow reaction, the crude reaction mixture is directly loaded onto the preparative HPLC injection loop to undergo HPLC purification. Purified compounds are collected via the LH 215 auto-sampler. The entire process is controlled using the chromatography management system software Chromeleon version 6.80 from Dionex.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27 (3): p. 275-80.)

Compounds respond is measured by the increase in cells based on ATP levels (Promega:CellTiterGlo®) after an incubation period of 4 days.

NSCs are thawed and expanded over 3 passages. On the 14$^{th}$ day, NSCs are seeded in Polyornithin/Laminin coated 384 well plates at a cell density of 21,000 cells/cm$^2$ in a media volume of 38 μl.

4 hours after cell seeding, compound solutions are added at a volume of 2 μl. Stock solutions of the compounds (water, 5% DMSO) are diluted to obtain a dose response (11 points, dilution factor is 2), ranging from 8 μM to 8 nM. Controls are run to consistently determine the neurogenic properties of the cells:

Negative (neutral) control is cell culture Media (final DMSO concentration: 0.25%).

Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)*100.

The values of $EC_{150}$ from the dose response curve are determined for each test compound. The $EC_{150}$ is the compound concentration at which 150% activity of control (100%) is reached. The preferred compounds show a $EC_{150}$ (μM) in the range of <7.0 μM as shown in Tables 1 and 2 below.

TABLE 1

List of examples and $EC_{150}$ data of novel compounds

| Example | Structure | Name | $EC_{150}$ (uM) |
| --- | --- | --- | --- |
| 1 | 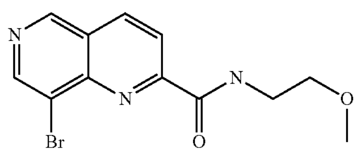 [SMILES: COCCNC(=O)c1ccc2cncc(Br)c2n1] | 8-Bromo-N-(2-methoxyethyl)-1,6-naphthyridine-2-carboxamide | 1.20 |
| 2 | 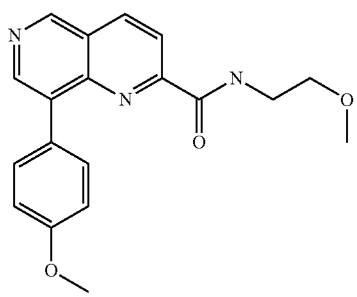 [SMILES: COCCNC(=O)c1ccc2cncc(-c3ccc(OC)cc3)c2n1] | N-(2-Methoxyethyl)-8-(4-methoxyphenyl)-1,6-naphthyridine-2-carboxamide | 0.03 |
| 3 | 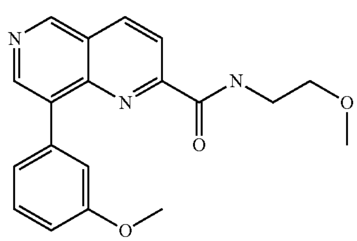 [SMILES: COCCNC(=O)c1ccc2cncc(-c3cccc(OC)c3)c2n1] | N-(2-Methoxyethyl)-8-(3-methoxyphenyl)-1,6-naphthyridine-2-carboxamide | 0.26 |
| 4 | 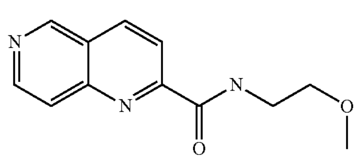 [SMILES: COCCNC(=O)c1ccc2cnccc2n1] | N-(2-Methoxyethyl)-1,6-naphthyridine-2-carboxamide | 0.5 |
| 5 | 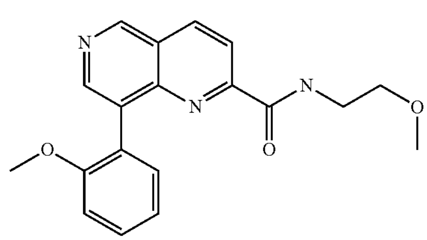 | N-(2-Methoxyethyl)-8-(2-methoxyphenyl)-1,6-naphthyridine-2-carboxamide | 0.26 |

TABLE 1-continued

List of examples and EC150 data of novel compounds

| Example | Structure | Name | EC150 (uM) |
|---|---|---|---|
| 6 | 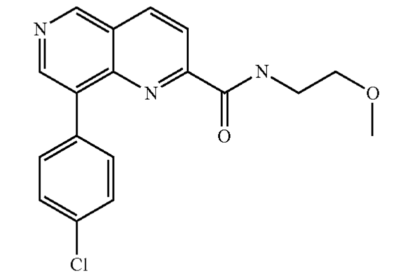 [SMILES: COCCNC(=O)c1ccc2cncc(-c3ccc(Cl)cc3)c2n1] | 8-(4-Chlorophenyl)-N-(2-methoxyethyl)-1,6-naphthyridine-2-carboxamide | 0.02 |
| 7 | 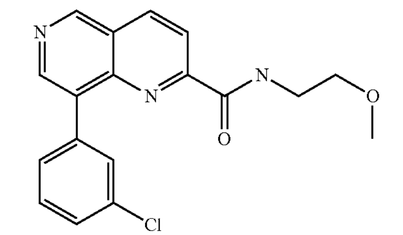 [SMILES: COCCNC(=O)c1ccc2cncc(-c3cccc(Cl)c3)c2n1] | 8-(3-Chlorophenyl)-N-(2-methoxyethyl)-1,6-naphthyridine-2-carboxamide | 0.32 |
| 8 | 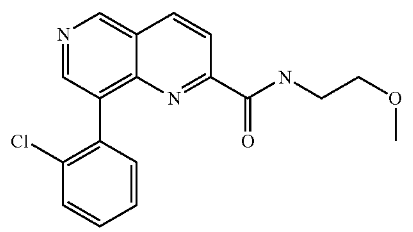 [SMILES: COCCNC(=O)c1ccc2cncc(-c3ccccc3Cl)c2n1] | 8-(2-Chlorophenyl)-N-(2-methoxyethyl)-1,6-naphthyridine-2-carboxamide | 0.33 |
| 9 | 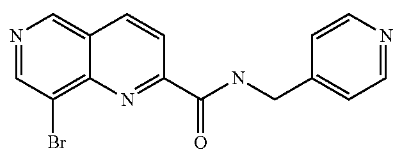 [SMILES: O=C(NCc1ccncc1)c1ccc2cncc(Br)c2n1] | 8-Bromo-[1,6]naphthyridine-2-carboxylic acid (pyridin-4-ylmethyl)-amide | 1.27 |
| 10 | 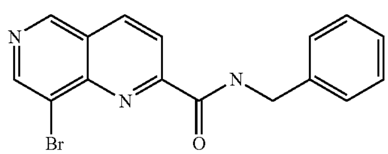 [SMILES: O=C(NCc1ccccc1)c1ccc2cncc(Br)c2n1] | N-Benzyl-8-bromo-1,6-naphthyridine-2-carboxamide | 0.76 |
| 11 | 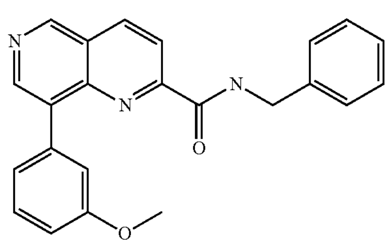 | N-Benzyl-8-(3-methoxyphenyl)-1,6-naphthyridine-2-carboxamide | 0.03 |
| 12 | 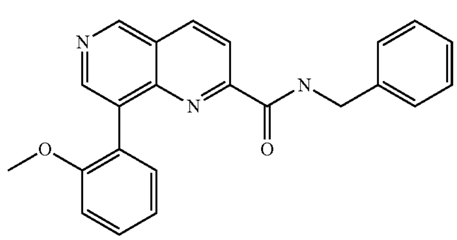 [SMILES: COc1ccccc1-c1cncc2ccc(C(=O)NCc3ccccc3)nc12] | N-Benzyl-8-(2-methoxyphenyl)-1,6-naphthyridine-2-carboxamide | 0.17 |

TABLE 1-continued

List of examples and EC$_{150}$ data of novel compounds

| Example | Structure | Name | EC$_{150}$ (uM) |
|---|---|---|---|
| 13 | 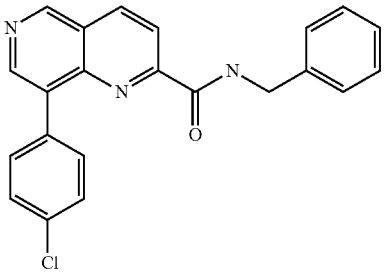 [SMILES: O=C(NCc1ccccc1)c1ccc2cncc(-c3ccc(Cl)cc3)c2n1] | N-Benzyl-8-(4-chlorophenyl)-1,6-naphthyridine-2-carboxamide | 0.05 |
| 14 | 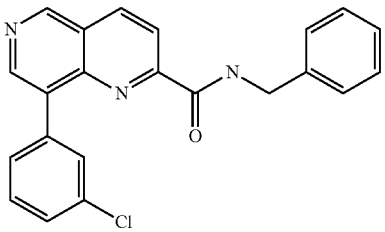 [SMILES: O=C(NCc1ccccc1)c1ccc2cncc(-c3cccc(Cl)c3)c2n1] | N-Benzyl-8-(3-chlorophenyl)-1,6-naphthyridine-2-carboxamide | 0.54 |
| 15 | 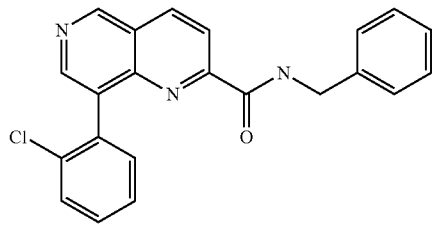 [SMILES: O=C(NCc1ccccc1)c1ccc2cncc(-c3ccccc3Cl)c2n1] | N-Benzyl-8-(2-chlorophenyl)-1,6-naphthyridine-2-carboxamide | 0.58 |
| 16 | 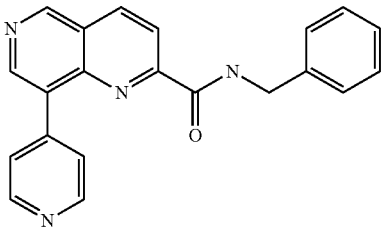 [SMILES: O=C(NCc1ccccc1)c1ccc2cncc(-c3ccncc3)c2n1] | N-Benzyl-8-(pyridin-4-yl)-1,6-naphthyridine-2-carboxamide | 0.04 |
| 17 | 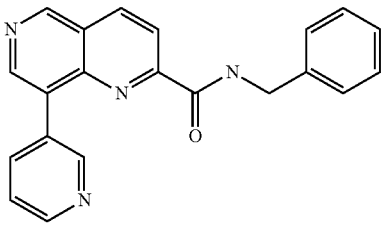 [SMILES: O=C(NCc1ccccc1)c1ccc2cncc(-c3cccnc3)c2n1] | N-Benzyl-8-(pyridin-3-yl)-1,6-naphthyridine-2-carboxamide | 0.11 |
| 18 | 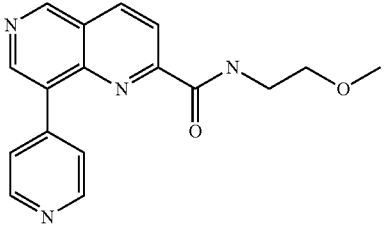 | N-(2-Methoxyethyl)-8-(pyridin-4-yl)-1,6-naphthyridine-2-carboxamide | 0.31 |

TABLE 1-continued

List of examples and EC$_{150}$ data of novel compounds

| Example | Structure | Name | EC$_{150}$ (uM) |
|---|---|---|---|
| 19 | 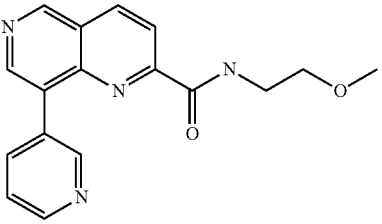 [SMILES: COCCNC(=O)c1ccc2cncc(-c3cccnc3)c2n1] | N-(2-methoxyethyl)-8-(pyridin-3-yl)-1,6-naphthyridine-2-carboxamide | 0.49 |
| 20 | 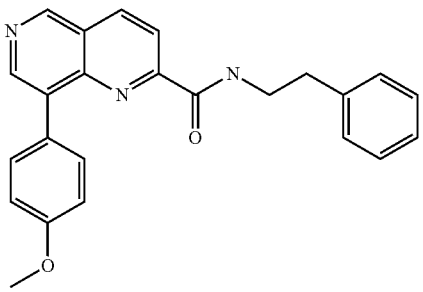 | 8-(4-Methoxyphenyl)-N-phenethyl-1,6-naphthyridine-2-carboxamide | 0.80 |
| 21 | 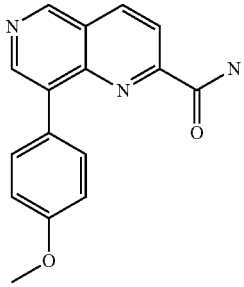 [SMILES: COc1ccc(-c2cncc3ccc(C(N)=O)nc23)cc1] | 8-(4-Methoxyphenyl)-1,6-naphthyridine-2-carboxamide | 0.01 |
| 22 | 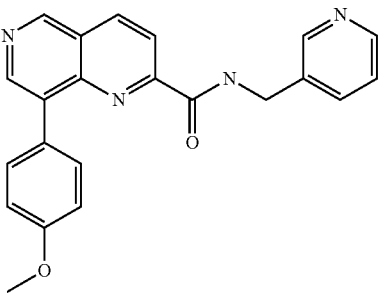 [SMILES: COc1ccc(-c2cncc3ccc(C(=O)NCc4cccnc4)nc23)cc1] | 8-(4-Methoxyphenyl)-N-(pyridin-3-ylmethyl)-1,6-naphthyridine-2-carboxamide | 0.03 |
| 23 | 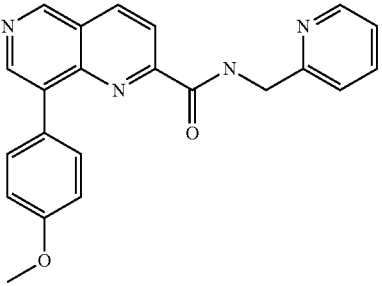 | 8-(4-Methoxyphenyl)-N-(pyridin-2-ylmethyl)-1,6-naphthyridine-2-carboxamide | 0.03 |

TABLE 1-continued

List of examples and EC$_{150}$ data of novel compounds

| Example | Structure | Name | EC$_{150}$ (uM) |
|---|---|---|---|
| 24 | 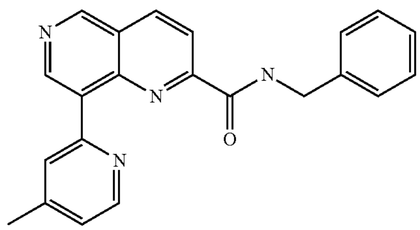 [SMILES: Cc1ccnc(-c2cncc3ccc(C(=O)NCc4ccccc4)nc23)c1] | N-Benzyl-8-(4-methylpyridin-2-yl)-1,6-naphthyridine-2-carboxamide | 0.94 |
| 25 | 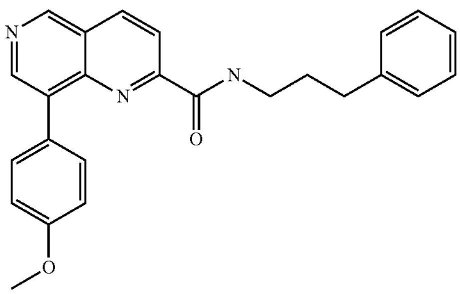 [SMILES: COc1ccc(-c2cncc3ccc(C(=O)NCCCc4ccccc4)nc23)cc1] | 8-(4-Methoxyphenyl)-N-(3-phenylpropyl)-1,6-naphthyridine-2-carboxamide | 0.67 |
| 26 | 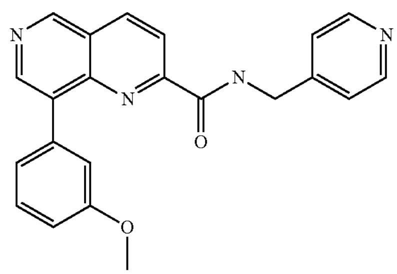 [SMILES: COc1cccc(-c2cncc3ccc(C(=O)NCc4ccncc4)nc23)c1] | 8-(3-Methoxyphenyl)-N-(pyridin-4-ylmethyl)-1,6-naphthyridine-2-carboxamide | 0.28 |
| 27 | 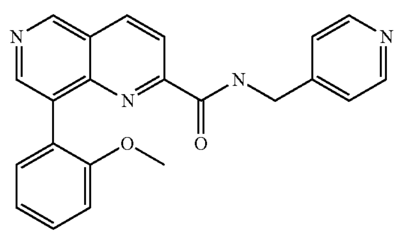 [SMILES: COc1ccccc1-c1cncc2ccc(C(=O)NCc3ccncc3)nc12] | 8-(2-Methoxyphenyl)-N-(pyridin-4-ylmethyl)-1,6-naphthyridine-2-carboxamide | 0.56 |
| 28 | 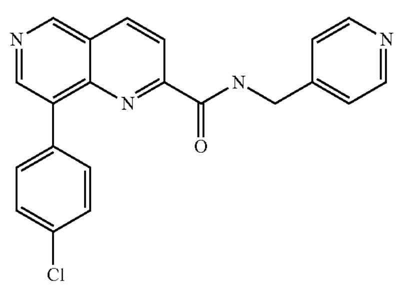 [SMILES: O=C(NCc1ccncc1)c1ccc2cncc(-c3ccc(Cl)cc3)c2n1] | 8-(4-Chlorophenyl)-N-(pyridin-4-ylmethyl)-1,6-naphthyridine-2-carboxamide | 0.10 |
| 29 | 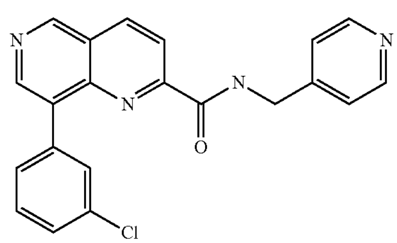 [SMILES: O=C(NCc1ccncc1)c1ccc2cncc(-c3cccc(Cl)c3)c2n1] | 8-(3-Chlorophenyl)-N-(pyridin-4-ylmethyl)-1,6-naphthyridine-2-carboxamide | 0.51 |

TABLE 1-continued

List of examples and EC$_{150}$ data of novel compounds

| Example | Structure | Name | EC$_{150}$ (uM) |
|---|---|---|---|
| 30 | 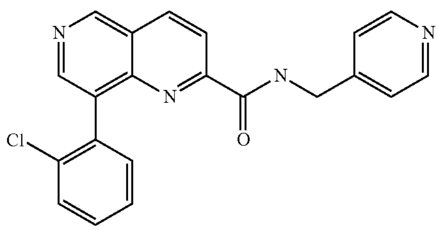 [SMILES: O=C(NCc1ccncc1)c1ccc2cncc(-c3ccccc3Cl)c2n1] | 8-(2-Chlorophenyl)-N-(pyridin-4-ylmethyl)-1,6-naphthyridine-2-carboxamide | 0.49 |
| 31 | 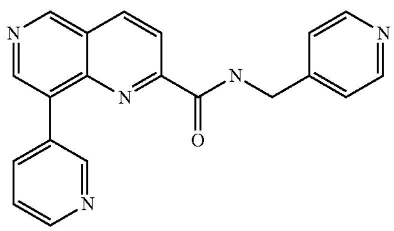 [SMILES: O=C(NCc1ccncc1)c1ccc2cncc(-c3cccnc3)c2n1] | 8-(Pyridin-3-yl)-N-(pyridin-4-ylmethyl)-1,6-naphthyridine-2-carboxamide | 0.54 |
| 32 | 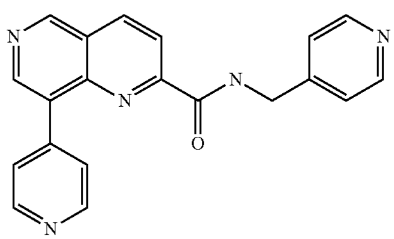 [SMILES: O=C(NCc1ccncc1)c1ccc2cncc(-c3ccncc3)c2n1] | 8-(Pyridin-4-yl)-N-(pyridin-4-ylmethyl)-1,6-naphthyridine-2-carboxamide | 0.29 |
| 33 | 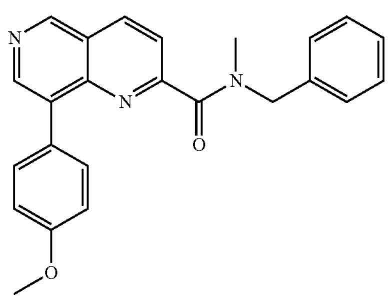 | N-Benzyl-8-(4-methoxyphenyl)-N-methyl-1,6-naphthyridine-2-carboxamide | 0.22 |
| 34 | 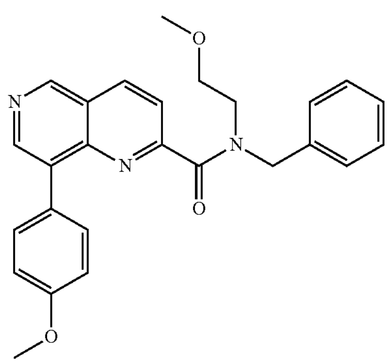 [SMILES: COCCN(Cc1ccccc1)C(=O)c1ccc2cncc(-c3ccc(OC)cc3)c2n1] | N-Benzyl-N-(2-methoxyethyl)-8-(4-methoxyphenyl)-1,6-naphthyridine-2-carboxamide | 0.21 |

TABLE 1-continued

List of examples and EC$_{150}$ data of novel compounds

| Example | Structure | Name | EC$_{150}$ (uM) |
|---|---|---|---|
| 35 | 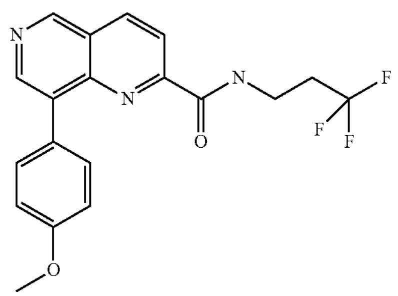 [SMILES: COc1ccc(-c2cncc3ccc(C(=O)NCCC(F)(F)F)nc23)cc1] | 8-(4-Methoxyphenyl)-N-(3,3,3-trifluoropropyl)-1,6-naphthyridine-2-carboxamide | 1.74 |
| 36 | 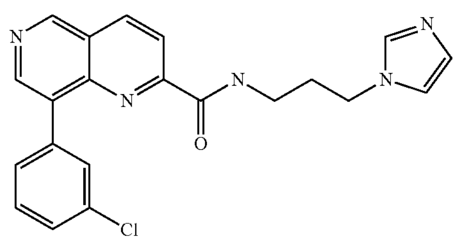 [SMILES: O=C(NCCCn1ccnc1)c1ccc2cncc(-c3cccc(Cl)c3)c2n1] | N-(3-(1H-Imidazol-1-yl)propyl)-8-(3-chlorophenyl)-1,6-naphthyridine-2-carboxamide | 1.04 |
| 37 | 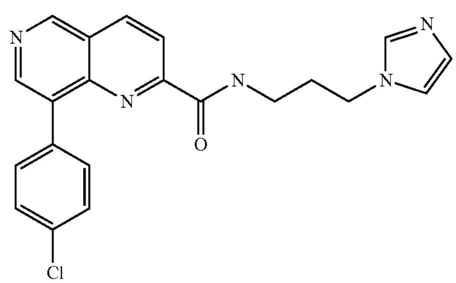 [SMILES: O=C(NCCCn1ccnc1)c1ccc2cncc(-c3ccc(Cl)cc3)c2n1] | N-(3-(1H-Imidazol-1-yl)propyl)-8-(4-chlorophenyl)-1,6-naphthyridine-2-carboxamide | 0.12 |
| 38 | 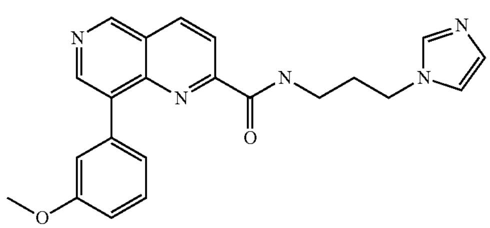 [SMILES: COc1cccc(-c2cncc3ccc(C(=O)NCCCn4ccnc4)nc23)c1] | N-(3-(1H-Imidazol-1-yl)propyl)-8-(3-methoxyphenyl)-1,6-naphthyridine-2-carboxamide | 1.95 |
| 39 | 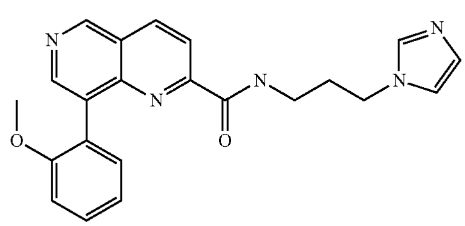 [SMILES: COc1ccccc1-c1cncc2ccc(C(=O)NCCCn3ccnc3)nc12] | N-(3-(1H-Imidazol-1-yl)propyl)-8-(2-methoxyphenyl)-1,6-naphthyridine-2-carboxamide | 0.74 |
| 40 | 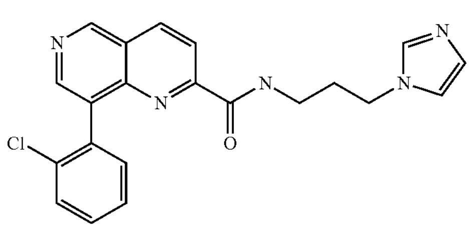 [SMILES: O=C(NCCCn1ccnc1)c1ccc2cncc(-c3ccccc3Cl)c2n1] | N-(3-(1H-Imidazol-1-yl)propyl)-8-(2-chlorophenyl)-1,6-naphthyridine-2-carboxamide | 0.69 |

TABLE 1-continued

List of examples and EC$_{150}$ data of novel compounds

| Example | Structure | Name | EC$_{150}$ (uM) |
|---|---|---|---|
| 41 | 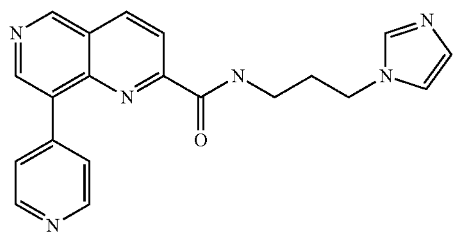 [SMILES: O=C(NCCCn1ccnc1)c1ccc2cncc(-c3ccncc3)c2n1] | N-(3-(1H-Imidazol-1-yl)propyl)-8-(pyridin-4-yl)-1,6-naphthyridine-2-carboxamide | 1.70 |
| 42 | 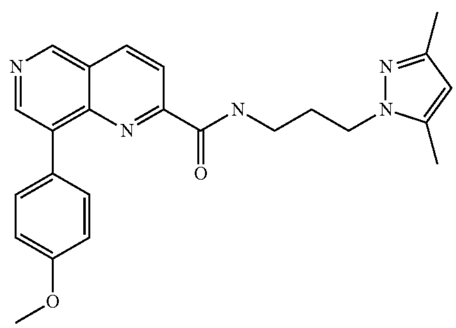 [SMILES: COc1ccc(-c2cncc3ccc(C(=O)NCCCn4nc(C)cc4C)nc23)cc1] | N-(3-(3,5-Dimethyl-1H-pyrazol-1-yl)propyl)-8-(4-methoxyphenyl)-1,6-naphthyridine-2-carboxamide | 0.25 |
| 43 | 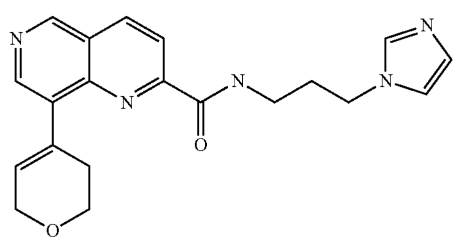 [SMILES: O=C(NCCCn1ccnc1)c1ccc2cncc(C3=CCOCC3)c2n1] | N-(3-(1H-Imidazol-1-yl)propyl)-8-(3,6-dihydro-2H-pyran-4-yl)-1,6-naphthyridine-2-carboxamide | 2.68 |
| 44 | 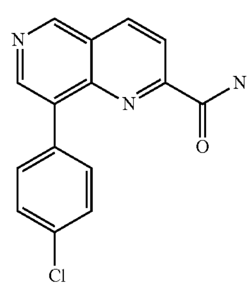 [SMILES: NC(=O)c1ccc2cncc(-c3ccc(Cl)cc3)c2n1] | 8-(4-Chlorophenyl)-1,6-naphthyridine-2-carboxamide | 0.03 |
| 45 | 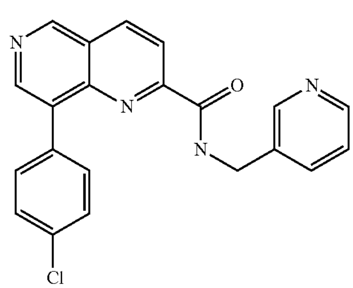 [SMILES: O=C(NCc1cccnc1)c1ccc2cncc(-c3ccc(Cl)cc3)c2n1] | 8-(4-Chlorophenyl)-N-(pyridin-3-ylmethyl)-1,6-naphthyridine-2-carboxamide | 0.02 |

TABLE 1-continued

List of examples and EC$_{150}$ data of novel compounds

| Example | Structure | Name | EC$_{150}$ (uM) |
|---|---|---|---|
| 46 | 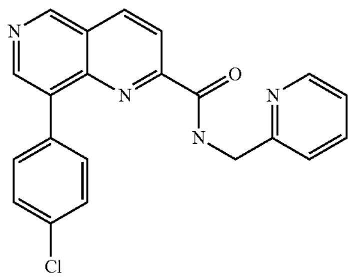 [SMILES: O=C(NCc1ccccn1)c1ccc2cncc(-c3ccc(Cl)cc3)c2n1] | 8-(4-Chlorophenyl)-N-(pyridin-2-ylmethyl)-1,6-naphthyridine-2-carboxamide | 0.51 |
| 47 | 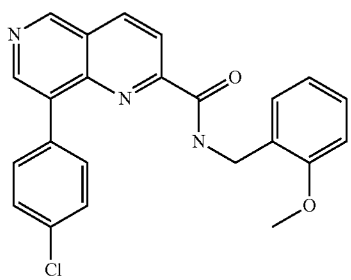 [SMILES: COc1ccccc1CNC(=O)c1ccc2cncc(-c3ccc(Cl)cc3)c2n1] | 8-(4-Chlorophenyl)-N-(2-methoxybenzyl)-1,6-naphthyridine-2-carboxamide | 0.13 |
| 48 | 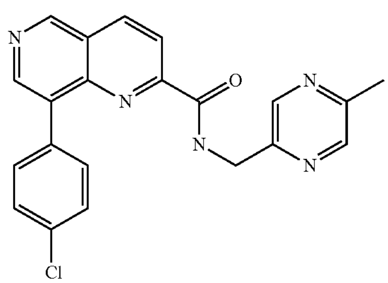 [SMILES: Cc1cnc(CNC(=O)c2ccc3cncc(-c4ccc(Cl)cc4)c3n2)cn1] | 8-(4-Chlorophenyl)-N-((5-methylpyrazin-2-yl)methyl)-1,6-naphthyridine-2-carboxamide | 0.88 |
| 49 | 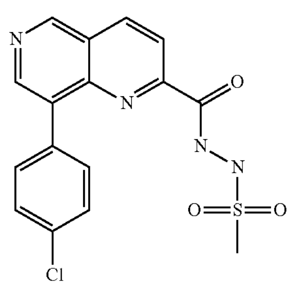 [SMILES: CS(=O)(=O)NNC(=O)c1ccc2cncc(-c3ccc(Cl)cc3)c2n1] | N'-(8-(4-Chlorophenyl)-1,6-naphthyridine-2-carbonyl)methanesulfonohydrazide | 0.07 |
| 50 | 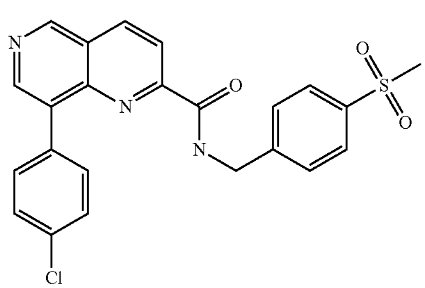 [SMILES: CS(=O)(=O)c1ccc(CNC(=O)c2ccc3cncc(-c4ccc(Cl)cc4)c3n2)cc1] | 8-(4-Chlorophenyl)-N-(4-(methylsulfonyl)benzyl)-1,6-naphthyridine-2-carboxamide | 0.32 |

TABLE 1-continued

List of examples and EC$_{150}$ data of novel compounds

| Example | Structure | Name | EC$_{150}$ (uM) |
|---|---|---|---|
| 51 | 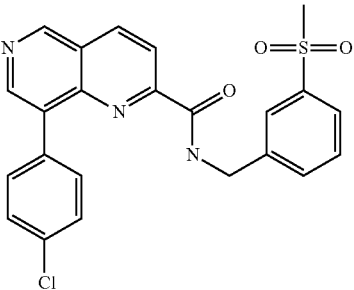 | 8-(4-Chlorophenyl)-N-(3-(methylsulfonyl)benzyl)-1,6-naphthyridine-2-carboxamide | 0.12 |
| 52 | 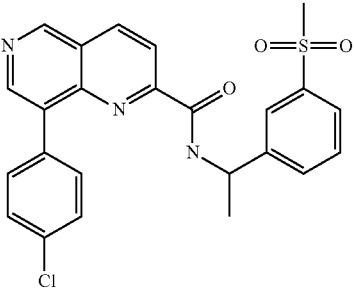 [SMILES: CC(NC(=O)c1ccc2cncc(-c3ccc(Cl)cc3)c2n1)c1cccc(S(C)(=O)=O)c1] | (−)-8-(4-Chloro-phenyl)-[1,6]naphthyridine-2-carboxylic acid [(S or R)-1-(3-methanesulfonyl-phenyl)-ethyl-amide | 0.80 |
| 53 | 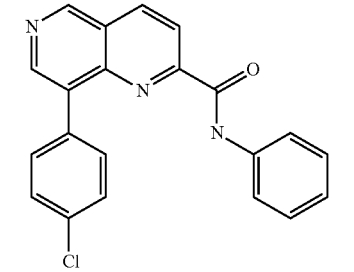 [SMILES: O=C(Nc1ccccc1)c1ccc2cncc(-c3ccc(Cl)cc3)c2n1] | 8-(4-Chlorophenyl)-N-phenyl-1,6-naphthyridine-2-carboxamide | 0.23 |
| 54 | 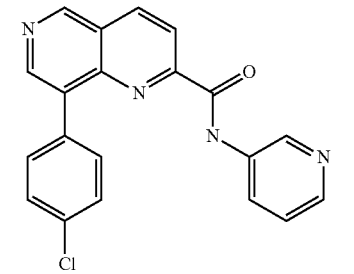 [SMILES: O=C(Nc1cccnc1)c1ccc2cncc(-c3ccc(Cl)cc3)c2n1] | 8-(4-Chlorophenyl)-N-(pyridin-3-yl)-1,6-naphthyridine-2-carboxamide | 0.8 |
| 55 | 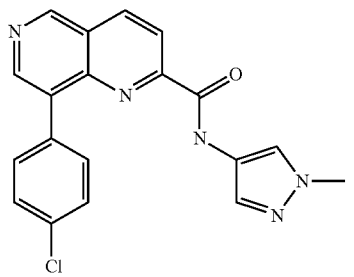 [SMILES: Cn1cc(NC(=O)c2ccc3cncc(-c4ccc(Cl)cc4)c3n2)cn1] | 8-(4-Chlorophenyl)-N-(1-methyl-1H-pyrazol-4-yl)-1,6-naphthyridine-2-carboxamide | 0.25 |

TABLE 1-continued

List of examples and EC$_{150}$ data of novel compounds

| Example | Structure | Name | EC$_{150}$ (uM) |
|---|---|---|---|
| 56 | 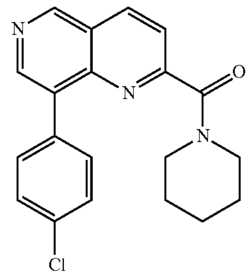 [SMILES: O=C(c1ccc2cncc(-c3ccc(Cl)cc3)c2n1)N1CCCCC1] | (8-(4-Chlorophenyl)-1,6-naphthyridin-2-yl)(piperidin-1-yl)methanone | 1.51 |
| 57 | 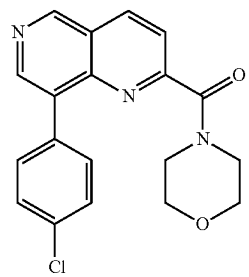 [SMILES: O=C(c1ccc2cncc(-c3ccc(Cl)cc3)c2n1)N1CCOCC1] | (8-(4-Chlorophenyl)-1,6-naphthyridin-2-yl)(morpholino)methanone | 0.17 |
| 58 | 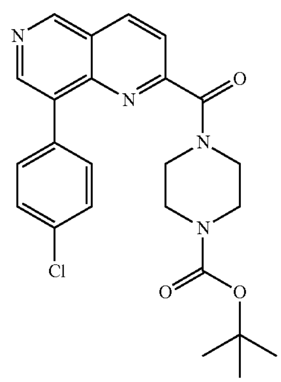 [SMILES: CC(C)(C)OC(=O)N1CCN(C(=O)c2ccc3cncc(-c4ccc(Cl)cc4)c3n2)CC1] | tert-Butyl 4-(8-(4-chlorophenyl)-1,6-naphthyridine-2-carbonyl)piperazine-1-carboxylate | 1.1 |
| 59 | 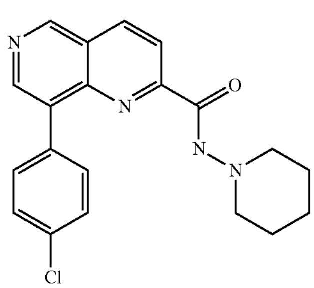 [SMILES: O=C(NN1CCCCC1)c1ccc2cncc(-c3ccc(Cl)cc3)c2n1] | 8-(4-Chlorophenyl)-N-(piperidin-1-yl)-1,6-naphthyridine-2-carboxamide | 1.48 |
| 60 | 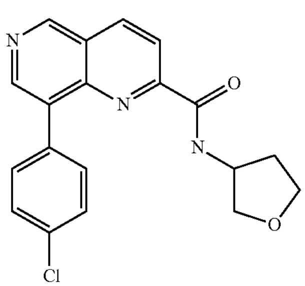 [SMILES: O=C(NC1CCOC1)c1ccc2cncc(-c3ccc(Cl)cc3)c2n1] | 8-(4-Chlorophenyl)-N-(tetrahydrofuran-3-yl)-1,6-naphthyridine-2-carboxamide | 0.15 |

TABLE 1-continued

List of examples and EC$_{150}$ data of novel compounds

| Example | Structure | Name | EC$_{150}$ (uM) |
|---|---|---|---|
| 61 | 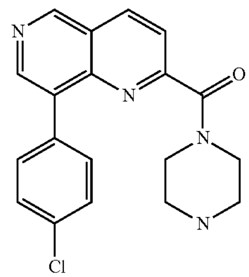 [SMILES: O=C(c1ccc2cncc(-c3ccc(Cl)cc3)c2n1)N1CCNCC1] | (8-(4-Chlorophenyl)-1,6-naphthyridin-2-yl)(piperazin-1-yl)methanone | 3.15 |
| 62 | 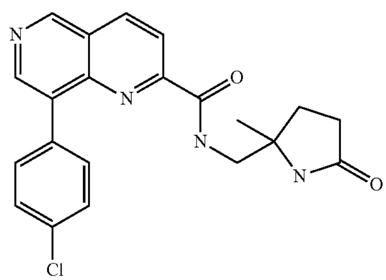 [SMILES: CC1(CNC(=O)c2ccc3cncc(-c4ccc(Cl)cc4)c3n2)CCC(=O)N1] | 8-(4-Chlorophenyl)-N-((2-methyl-5-oxopyrrolidin-2-yl)methyl)-1,6-naphthyridine-2-carboxamide | 0.01 |
| 63 | 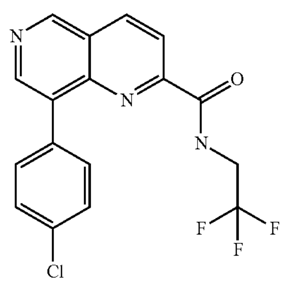 [SMILES: O=C(NCC(F)(F)F)c1ccc2cncc(-c3ccc(Cl)cc3)c2n1] | 8-(4-Chlorophenyl)-N-(2,2,2-trifluoroethyl)-1,6-naphthyridine-2-carboxamide | 0.23 |
| 64 | 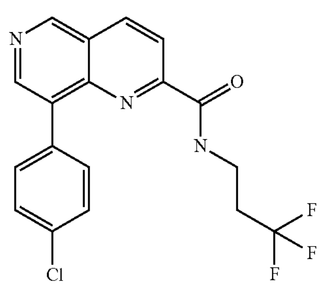 [SMILES: O=C(NCCC(F)(F)F)c1ccc2cncc(-c3ccc(Cl)cc3)c2n1] | 8-(4-Chlorophenyl)-N-(3,3,3-trifluoropropyl)-1,6-naphthyridine-2-carboxamide | 0.15 |
| 65 | 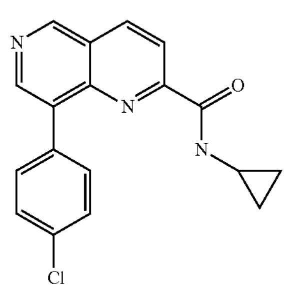 [SMILES: O=C(NC1CC1)c1ccc2cncc(-c3ccc(Cl)cc3)c2n1] | 8-(4-Chlorophenyl)-N-cyclopropyl-1,6-naphthyridine-2-carboxamide | 0.08 |

TABLE 1-continued

List of examples and EC$_{150}$ data of novel compounds

| Example | Structure | Name | EC$_{150}$ (uM) |
|---|---|---|---|
| 66 | 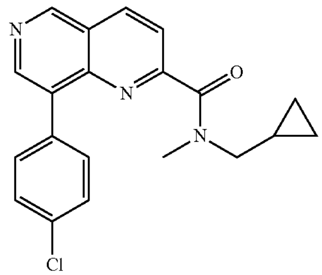 [SMILES: CN(CC1CC1)C(=O)c1ccc2cncc(-c3ccc(Cl)cc3)c2n1] | 8-(4-Chlorophenyl)-N-(cyclopropylmethyl)-N-methyl-1,6-naphthyridine-2-carboxamide | 0.7 |
| 67 | 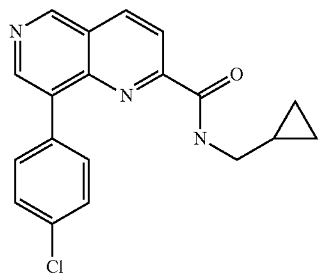 [SMILES: O=C(NCC1CC1)c1ccc2cncc(-c3ccc(Cl)cc3)c2n1] | 8-(4-Chlorophenyl)-N-(cyclopropylmethyl)-1,6-naphthyridine-2-carboxamide | 0.01 |
| 68 | 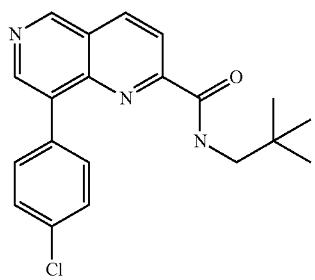 [SMILES: CC(C)(C)CNC(=O)c1ccc2cncc(-c3ccc(Cl)cc3)c2n1] | 8-(4-Chlorophenyl)-N-neopentyl-1,6-naphthyridine-2-carboxamide | 0.07 |
| 69 | 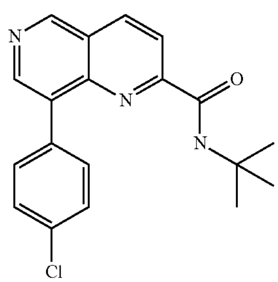 [SMILES: CC(C)(C)NC(=O)c1ccc2cncc(-c3ccc(Cl)cc3)c2n1] | N-tert-Butyl-8-(4-chlorophenyl)-1,6-naphthyridine-2-carboxamide | 0.32 |
| 70 | 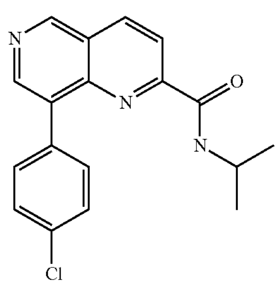 [SMILES: CC(C)NC(=O)c1ccc2cncc(-c3ccc(Cl)cc3)c2n1] | 8-(4-Chlorophenyl)-N-isopropyl-1,6-naphthyridine-2-carboxamide | 0.6 |

TABLE 1-continued

List of examples and EC$_{150}$ data of novel compounds

| Example | Structure | Name | EC$_{150}$ (uM) |
|---|---|---|---|
| 71 | 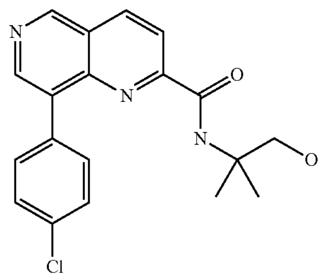 [SMILES: CC(C)(CO)NC(=O)c1ccc2cncc(-c3ccc(Cl)cc3)c2n1] | 8-(4-Chlorophenyl)-N-(1-hydroxy-2-methylpropan-2-yl)-1,6-naphthyridine-2-carboxamide | 1.06 |
| 72 | 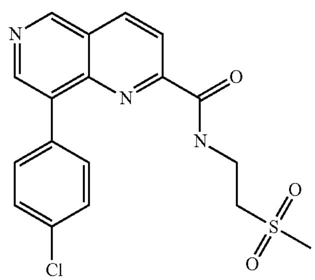 [SMILES: CS(=O)(=O)CCNC(=O)c1ccc2cncc(-c3ccc(Cl)cc3)c2n1] | 8-(4-Chlorophenyl)-N-(2-(methylsulfonyl)ethyl)-1,6-naphthyridine-2-carboxamide | 0.10 |
| 73 | 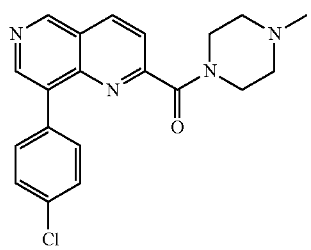 [SMILES: CN1CCN(C(=O)c2ccc3cncc(-c4ccc(Cl)cc4)c3n2)CC1] | (8-(4-Chlorophenyl)-1,6-naphthyridin-2-yl)(4-methylpiperazin-1-yl)methanone | 0.64 |
| 74 | 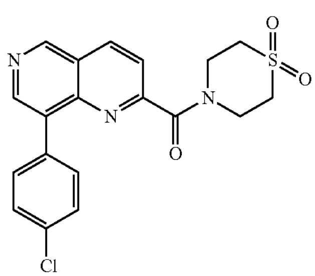 [SMILES: O=C(c1ccc2cncc(-c3ccc(Cl)cc3)c2n1)N1CCS(=O)(=O)CC1] | [8-(4-Chloro-phenyl)-[1,6]naphthyridin-2-yl]-(1,1-dioxo-thiomorpholin-4-yl)-methanone | 1.68 |
| 75 | 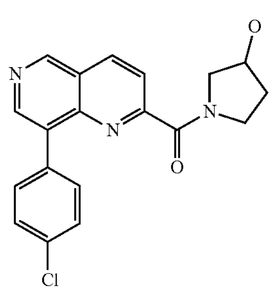 [SMILES: O=C(c1ccc2cncc(-c3ccc(Cl)cc3)c2n1)N1CCC(O)C1] | (8-(4-Chlorophenyl)-1,6-naphthyridin-2-yl)(3-hydroxypyrrolidin-1-yl)methanone | 0.40 |

TABLE 1-continued

List of examples and EC$_{150}$ data of novel compounds

| Example | Structure | Name | EC$_{150}$ (uM) |
|---|---|---|---|
| 76 | 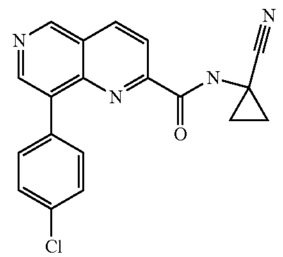 [SMILES: N#CC1(NC(=O)c2ccc3cncc(-c4ccc(Cl)cc4)c3n2)CC1] | 8-(4-Chlorophenyl)-N-(1-cyanocyclopropyl)-1,6-naphthyridine-2-carboxamide | 1.84 |
| 77 | 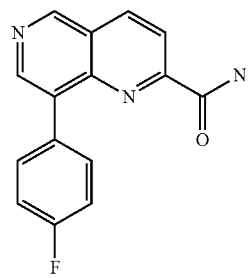 [SMILES: NC(=O)c1ccc2cncc(-c3ccc(F)cc3)c2n1] | 8-(4-Fluorophenyl)-1,6-naphthyridine-2-carboxamide | 0.09 |
| 78 | 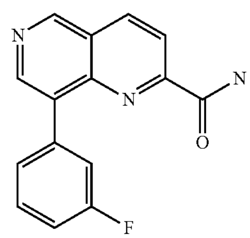 [SMILES: NC(=O)c1ccc2cncc(-c3cccc(F)c3)c2n1] | 8-(3-Fluorophenyl)-1,6-naphthyridine-2-carboxamide | 0.05 |
| 79 | 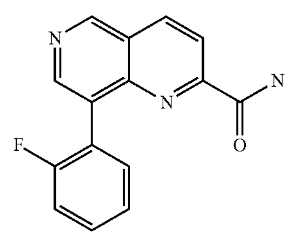 [SMILES: NC(=O)c1ccc2cncc(-c3ccccc3F)c2n1] | 8-(2-Fluorophenyl)-1,6-naphthyridine-2-carboxamide | 0.03 |
| 80 | 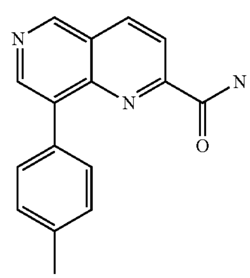 [SMILES: Cc1ccc(-c2cncc3ccc(C(N)=O)nc23)cc1] | 8-Tolyl-1,6-naphthyridine-2-carboxamide | 0.03 |
| 81 | 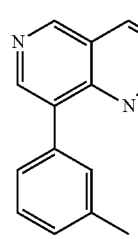 | 8-m-Tolyl-1,6-naphthyridine-2-carboxamide | 0.05 |

TABLE 1-continued

List of examples and EC$_{150}$ data of novel compounds

| Example | Structure | Name | EC$_{150}$ (uM) |
|---|---|---|---|
| 82 | 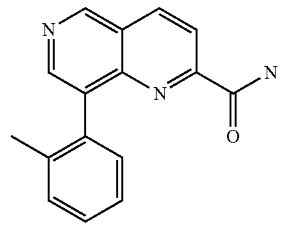 [SMILES: Cc1ccccc1-c1cncc2ccc(C(N)=O)nc12] | 8-o-Tolyl-1,6-naphthyridine-2-carboxamide | 2.05 |
| 83 | 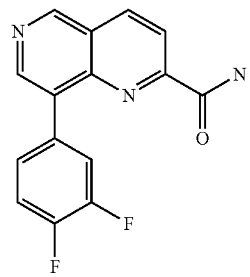 [SMILES: NC(=O)c1ccc2cncc(-c3ccc(F)c(F)c3)c2n1] | 8-(3,4-Difluorophenyl)-1,6-naphthyridine-2-carboxamide | 0.10 |
| 84 | 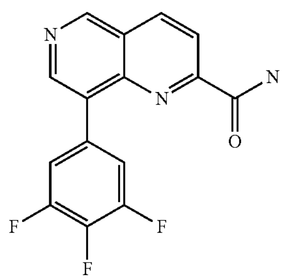 [SMILES: NC(=O)c1ccc2cncc(-c3cc(F)c(F)c(F)c3)c2n1] | 8-(3,4,5-Trifluorophenyl)-1,6-naphthyridine-2-carboxamide | 0.25 |
| 85 | 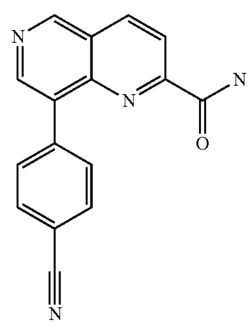 [SMILES: N#Cc1ccc(-c2cncc3ccc(C(N)=O)nc23)cc1] | 8-(4-Cyanophenyl)-1,6-naphthyridine-2-carboxamide | 0.05 |
| 86 | 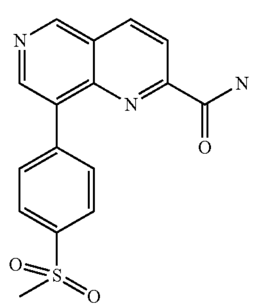 [SMILES: CS(=O)(=O)c1ccc(-c2cncc3ccc(C(N)=O)nc23)cc1] | 8-(4-(Methylsulfonyl)phenyl)-1,6-naphthyridine-2-carboxamide | 0.03 |

TABLE 1-continued

List of examples and EC$_{150}$ data of novel compounds

| Example | Structure | Name | EC$_{150}$ (uM) |
|---|---|---|---|
| 87 | 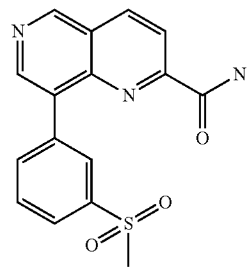 [SMILES: CS(=O)(=O)c1cccc(-c2cncc3ccc(C(N)=O)nc23)c1] | 8-(3-(Methylsulfonyl)phenyl)-1,6-naphthyridine-2-carboxamide | 0.79 |
| 88 | 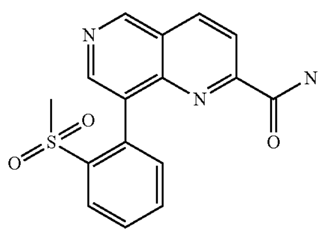 [SMILES: CS(=O)(=O)c1ccccc1-c1cncc2ccc(C(N)=O)nc12] | 8-(2-(Methylsulfonyl)phenyl)-1,6-naphthyridine-2-carboxamide | 0.5 |
| 89 | 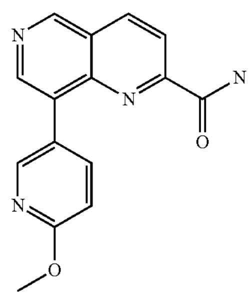 [SMILES: COc1ccc(-c2cncc3ccc(C(N)=O)nc23)cn1] | 8-(6-Methoxypyridin-3-yl)-1,6-naphthyridine-2-carboxamide | 0.09 |
| 90 | 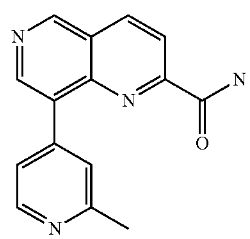 [SMILES: Cc1cc(-c2cncc3ccc(C(N)=O)nc23)ccn1] | 8-(2-Methylpyridin-4-yl)-1,6-naphthyridine-2-carboxamide | 0.17 |
| 91 | 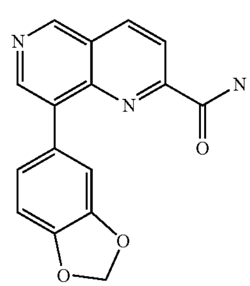 [SMILES: NC(=O)c1ccc2cncc(-c3ccc4c(c3)OCO4)c2n1] | 8-(Benzo[d][1,3]dioxol-5-yl)-1,6-naphthyridine-2-carboxamide | 0.03 |

TABLE 1-continued

List of examples and EC$_{150}$ data of novel compounds

| Example | Structure | Name | EC$_{150}$ (uM) |
|---|---|---|---|
| 92 | 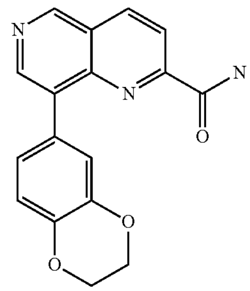 [SMILES: NC(=O)c1ccc2cncc(-c3ccc4c(c3)OCCO4)c2n1] | 8-(2,3-Dihydrobenzo[b][1,4]dioxin-6-yl)-1,6-naphthyridine-2-carboxamide | 0.03 |
| 93 | 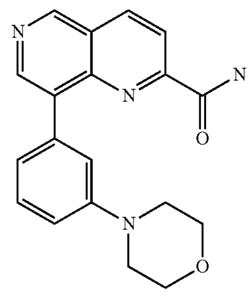 [SMILES: NC(=O)c1ccc2cncc(-c3cccc(N4CCOCC4)c3)c2n1] | 8-(3-Morpholinophenyl)-1,6-naphthyridine-2-carboxamide | 0.21 |
| 94 | 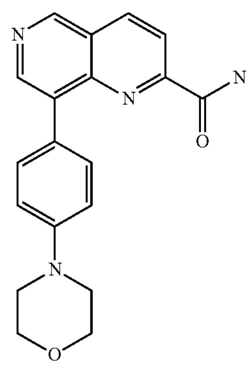 [SMILES: NC(=O)c1ccc2cncc(-c3ccc(N4CCOCC4)cc3)c2n1] | 8-(4-Morpholinophenyl)-1,6-naphthyridine-2-carboxamide | 0.01 |
| 95 | 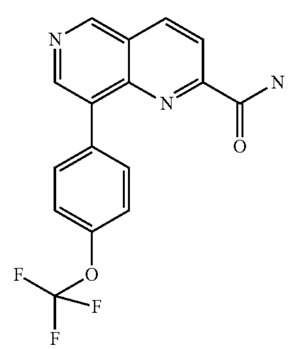 [SMILES: NC(=O)c1ccc2cncc(-c3ccc(OC(F)(F)F)cc3)c2n1] | 8-(4-(Trifluoromethoxy)phenyl)-1,6-naphthyridine-2-carboxamide | 0.05 |
| 96 | 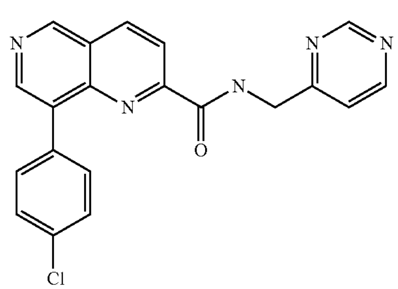 [SMILES: O=C(NCc1ccncn1)c1ccc2cncc(-c3ccc(Cl)cc3)c2n1] | 8-(4-Chlorophenyl)-N-(pyrimidin-4-ylmethyl)-1,6-naphthyridine-2-carboxamide | 0.17 |

TABLE 1-continued

List of examples and EC$_{150}$ data of novel compounds

| Example | Structure | Name | EC$_{150}$ (uM) |
|---|---|---|---|
| 97 | 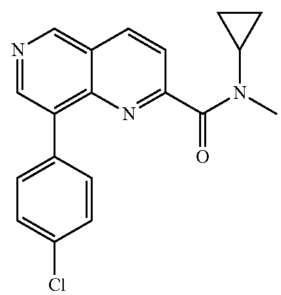 [SMILES: CN(C(=O)c1ccc2cncc(-c3ccc(Cl)cc3)c2n1)C1CC1] | 8-(4-Chlorophenyl)-N-cyclopropyl-N-methyl-1,6-naphthyridine-2-carboxamide | 0.26 |
| 98 | 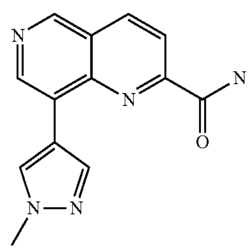 [SMILES: Cn1cc(-c2cncc3ccc(C(N)=O)nc23)cn1] | 8-(1-Methyl-1H-pyrazol-4-yl)-1,6-naphthyridine-2-carboxamide | 0.14 |
| 99 | 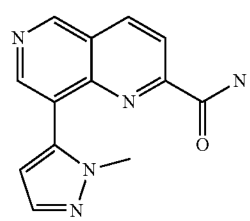 [SMILES: Cn1nccc1-c1cncc2ccc(C(N)=O)nc12] | 8-(1-Methyl-1H-pyrazol-5-yl)-1,6-naphthyridine-2-carboxamide | 2.20 |
| 100 | 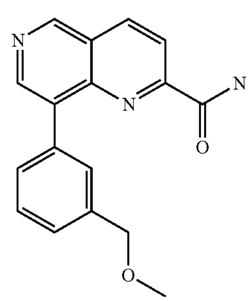 [SMILES: COCc1cccc(-c2cncc3ccc(C(N)=O)nc23)c1] | 8-(3-(Methoxymethyl)phenyl)-1,6-naphthyridine-2-carboxamide | 0.02 |
| 101 | 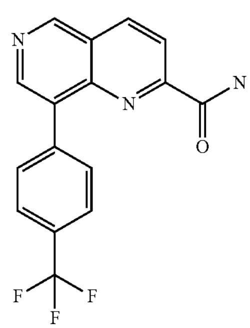 [SMILES: NC(=O)c1ccc2cncc(-c3ccc(C(F)(F)F)cc3)c2n1] | 8-(4-(Trifluoromethyl)phenyl)-1,6-naphthyridine-2-carboxamide | 0.02 |

TABLE 1-continued

List of examples and EC$_{150}$ data of novel compounds

| Example | Structure | Name | EC$_{150}$ (uM) |
|---|---|---|---|
| 102 | 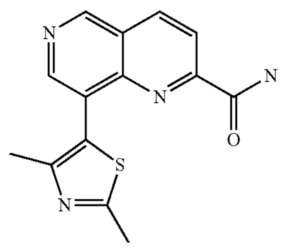 [SMILES: Cc1nc(C)c(-c2cncc3ccc(C(N)=O)nc23)s1] | 8-(2,4-Dimethylthiazol-5-yl)-1,6-naphthyridine-2-carboxamide | 0.14 |
| 103 | 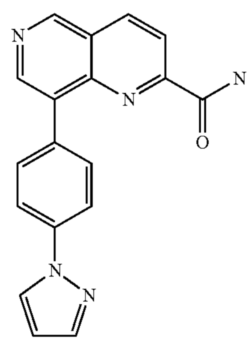 [SMILES: NC(=O)c1ccc2cncc(-c3ccc(-n4cccn4)cc3)c2n1] | 8-(4-(1H-Pyrazol-1-yl)phenyl)-1,6-naphthyridine-2-carboxamide | 0.01 |
| 104 | 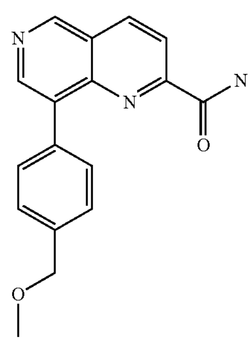 [SMILES: COCc1ccc(-c2cncc3ccc(C(N)=O)nc23)cc1] | 8-(4-(Methoxymethyl)phenyl)-1,6-naphthyridine-2-carboxamide | 0.02 |
| 105 | 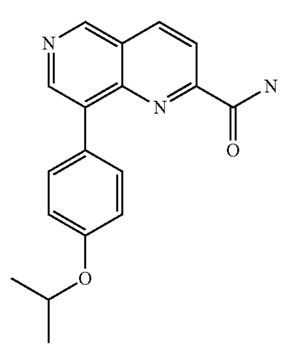 [SMILES: CC(C)Oc1ccc(-c2cncc3ccc(C(N)=O)nc23)cc1] | 8-(4-Isopropoxyphenyl)-1,6-naphthyridine-2-carboxamide | 0.01 |

TABLE 1-continued

List of examples and EC150 data of novel compounds

| Example | Structure | Name | EC150 (uM) |
|---|---|---|---|
| 106 | 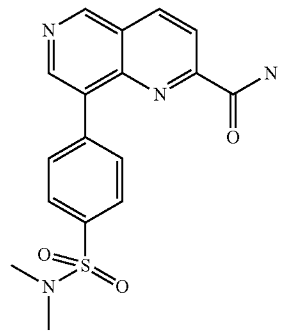 [SMILES: CN(C)S(=O)(=O)c1ccc(-c2cncc3ccc(C(N)=O)nc23)cc1] | 8-(4-(N,N-Dimethylsulfamoyl)phenyl)-1,6-naphthyridine-2-carboxamide | 0.19 |
| 107 | 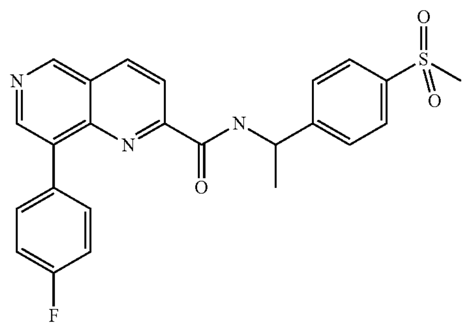 [SMILES: CC(NC(=O)c1ccc2cncc(-c3ccc(F)cc3)c2n1)c1ccc(S(C)(=O)=O)cc1] | 8-(4-Fluorophenyl)-N-(1-(4-(methylsulfonyl)phenyl)ethyl)-1,6-naphthyridine-2-carboxamide | 0.1 |
| 108 | 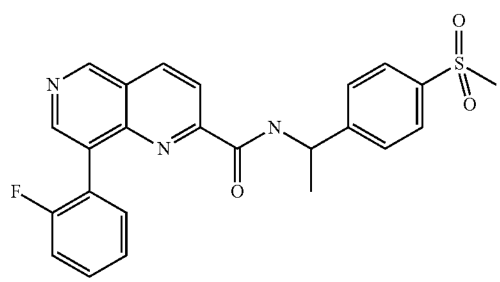 [SMILES: CC(NC(=O)c1ccc2cncc(-c3ccccc3F)c2n1)c1ccc(S(C)(=O)=O)cc1] | 8-(2-Fluorophenyl)-N-(1-(4-(methylsulfonyl)phenyl)ethyl)-1,6-naphthyridine-2-carboxamide | 0.50 |
| 109 | 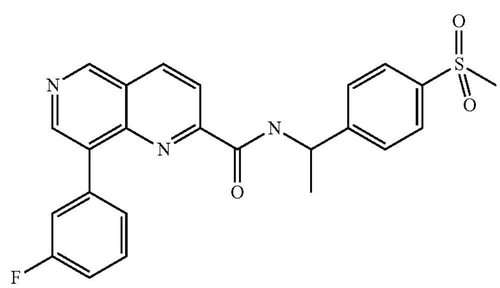 [SMILES: CC(NC(=O)c1ccc2cncc(-c3cccc(F)c3)c2n1)c1ccc(S(C)(=O)=O)cc1] | 8-(3-Fluorophenyl)-N-(1-(4-(methylsulfonyl)phenyl)ethyl)-1,6-naphthyridine-2-carboxamide | 4.2 |
| 110 | 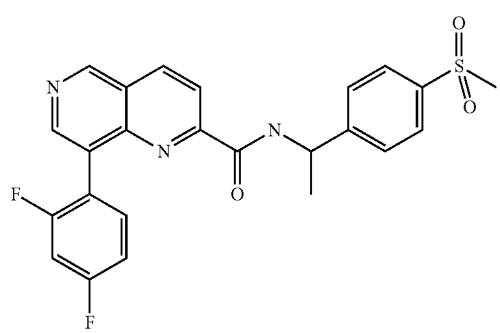 [SMILES: CC(NC(=O)c1ccc2cncc(-c3ccc(F)cc3F)c2n1)c1ccc(S(C)(=O)=O)cc1] | 8-(2,4-Difluorophenyl)-N-(1-(4-(methylsulfonyl)phenyl)ethyl)-1,6-naphthyridine-2-carboxamide | 0.49 |

TABLE 1-continued

List of examples and EC$_{150}$ data of novel compounds

| Example | Structure | Name | EC$_{150}$ (uM) |
|---|---|---|---|
| 111 | 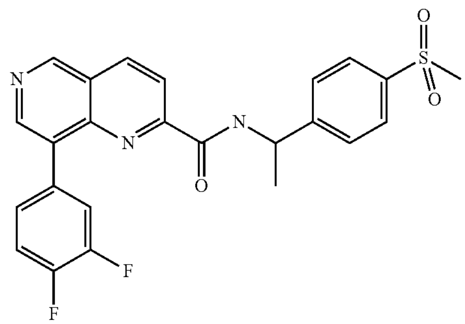 [SMILES: CC(NC(=O)c1ccc2cncc(-c3ccc(F)c(F)c3)c2n1)c1ccc(S(C)(=O)=O)cc1] | 8-(3,4-Difluorophenyl)-N-(1-(4-(methylsulfonyl)phenyl)ethyl)-1,6-naphthyridine-2-carboxamide | 0.3 |
| 112 | 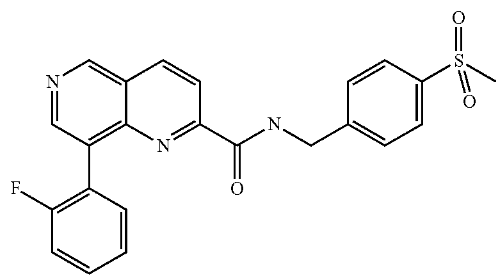 [SMILES: CS(=O)(=O)c1ccc(CNC(=O)c2ccc3cncc(-c4ccccc4F)c3n2)cc1] | 8-(2-Fluorophenyl)-N-(4-(methylsulfonyl)benzyl)-1,6-naphthyridine-2-carboxamide | 0.25 |
| 113 | 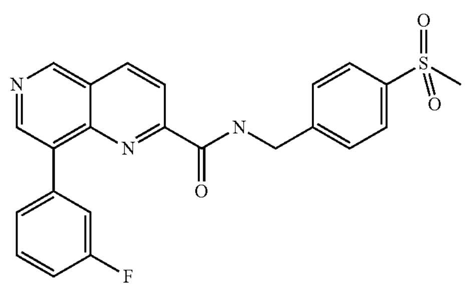 [SMILES: CS(=O)(=O)c1ccc(CNC(=O)c2ccc3cncc(-c4cccc(F)c4)c3n2)cc1] | 8-(3-Fluorophenyl)-N-(4-(methylsulfonyl)benzyl)-1,6-naphthyridine-2-carboxamide | 0.17 |
| 114 | 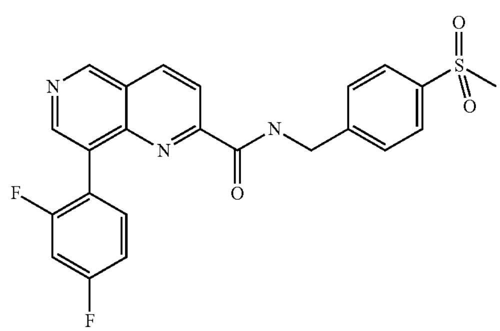 [SMILES: CS(=O)(=O)c1ccc(CNC(=O)c2ccc3cncc(-c4ccc(F)cc4F)c3n2)cc1] | 8-(2,4-Difluorophenyl)-N-(4-(methylsulfonyl)benzyl)-1,6-naphthyridine-2-carboxamide | 0.51 |
| 115 | 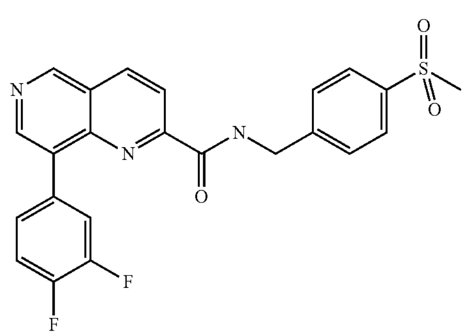 [SMILES: CS(=O)(=O)c1ccc(CNC(=O)c2ccc3cncc(-c4ccc(F)c(F)c4)c3n2)cc1] | 8-(3,4-Difluorophenyl)-N-(4-(methylsulfonyl)benzyl)-1,6-naphthyridine-2-carboxamide | 1.95 |

TABLE 1-continued

List of examples and EC$_{150}$ data of novel compounds

| Example | Structure | Name | EC$_{150}$ (uM) |
| --- | --- | --- | --- |
| 116 | 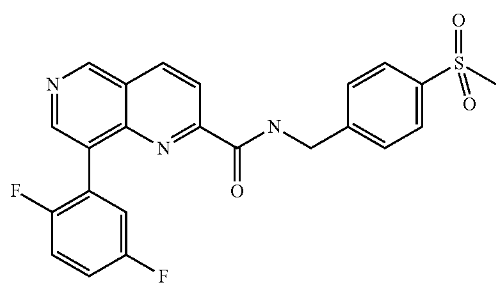 [SMILES: CS(=O)(=O)c1ccc(CNC(=O)c2ccc3cncc(-c4cc(F)ccc4F)c3n2)cc1] | 8-(2,5-Difluorophenyl)-N-(4-(methylsulfonyl)benzyl)-1,6-naphthyridine-2-carboxamide | 1.65 |
| 117 | 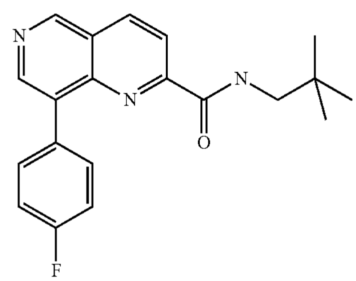 [SMILES: CC(C)(C)CNC(=O)c1ccc2cncc(-c3ccc(F)cc3)c2n1] | 8-(4-Fluorophenyl)-N-neopentyl-1,6-naphthyridine-2-carboxamide | 0.07 |
| 118 | 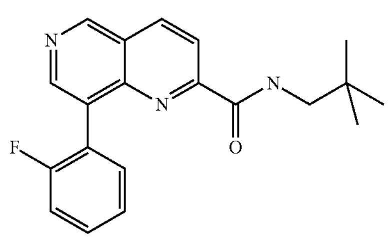 [SMILES: CC(C)(C)CNC(=O)c1ccc2cncc(-c3ccccc3F)c2n1] | 8-(2-Fluorophenyl)-N-neopentyl-1,6-naphthyridine-2-carboxamide | 0.04 |
| 119 | 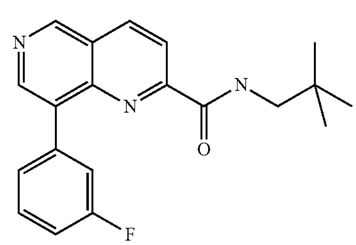 [SMILES: CC(C)(C)CNC(=O)c1ccc2cncc(-c3cccc(F)c3)c2n1] | 8-(3-Fluorophenyl)-N-neopentyl-1,6-naphthyridine-2-carboxamide | 0.27 |
| 120 | 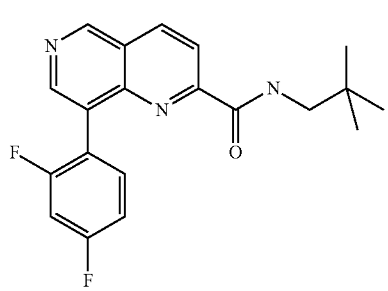 [SMILES: CC(C)(C)CNC(=O)c1ccc2cncc(-c3ccc(F)cc3F)c2n1] | 8-(2,4-Difluorophenyl)-N-neopentyl-1,6-naphthyridine-2-carboxamide | 0.08 |

TABLE 1-continued

List of examples and EC150 data of novel compounds

| Example | Structure | Name | EC150 (uM) |
|---|---|---|---|
| 121 | 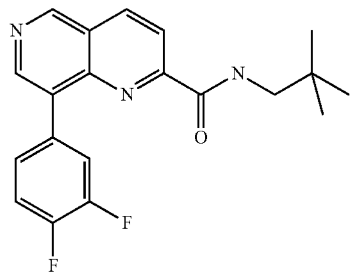 [SMILES: CC(C)(C)CNC(=O)c1ccc2cncc(-c3ccc(F)c(F)c3)c2n1] | 8-(3,4-Difluorophenyl)-N-neopentyl-1,6-naphthyridine-2-carboxamide | 0.26 |
| 122 | 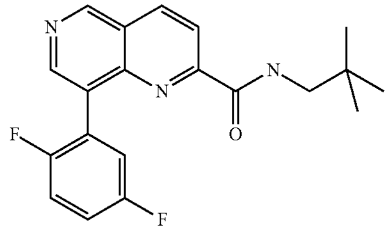 [SMILES: CC(C)(C)CNC(=O)c1ccc2cncc(-c3cc(F)ccc3F)c2n1] | 8-(2,5-Difluorophenyl)-N-neopentyl-1,6-naphthyridine-2-carboxamide | 0.12 |
| 123 | 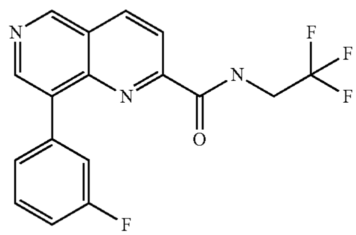 [SMILES: O=C(NCC(F)(F)F)c1ccc2cncc(-c3cccc(F)c3)c2n1] | 8-(3-Fluorophenyl)-N-(2,2,2-trifluoroethyl)-1,6-naphthyridine-2-carboxamide | 0.38 |
| 124 | 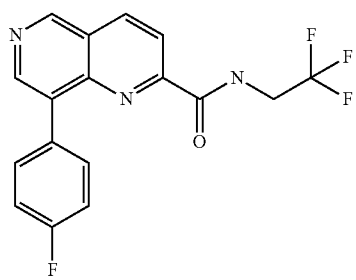 [SMILES: O=C(NCC(F)(F)F)c1ccc2cncc(-c3ccc(F)cc3)c2n1] | 8-(4-Fluorophenyl)-N-(2,2,2-trifluoroethyl)-1,6-naphthyridine-2-carboxamide | 0.07 |
| 125 | 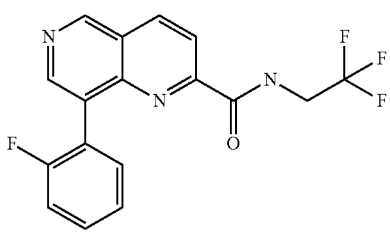 [SMILES: O=C(NCC(F)(F)F)c1ccc2cncc(-c3ccccc3F)c2n1] | 8-(2-Fluorophenyl)-N-(2,2,2-trifluoroethyl)-1,6-naphthyridine-2-carboxamide | 0.04 |
| 126 | 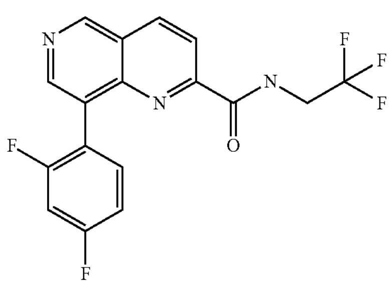 [SMILES: O=C(NCC(F)(F)F)c1ccc2cncc(-c3ccc(F)cc3F)c2n1] | 8-(2,4-Difluorophenyl)-N-(2,2,2-trifluoroethyl)-1,6-naphthyridine-2-carboxamide | 0.06 |

TABLE 1-continued

List of examples and EC$_{150}$ data of novel compounds

| Example | Structure | Name | EC$_{150}$ (uM) |
|---|---|---|---|
| 127 | 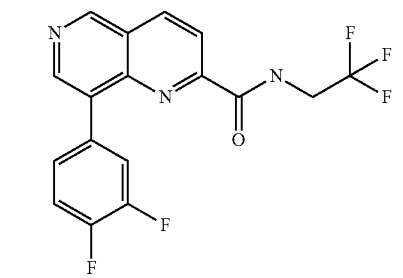 [SMILES: O=C(NCC(F)(F)F)c1ccc2cncc(-c3ccc(F)c(F)c3)c2n1] | 8-(3,4-Difluorophenyl)-N-(2,2,2-trifluoroethyl)-1,6-naphthyridine-2-carboxamide | 0.23 |
| 128 | 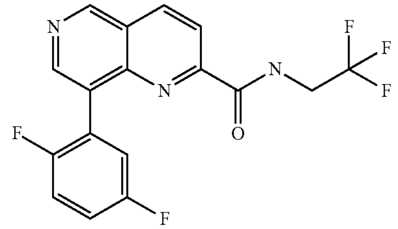 [SMILES: O=C(NCC(F)(F)F)c1ccc2cncc(-c3cc(F)ccc3F)c2n1] | 8-(2,5-Difluorophenyl)-N-(2,2,2-trifluoroethyl)-1,6-naphthyridine-2-carboxamide | 0.13 |
| 129 | 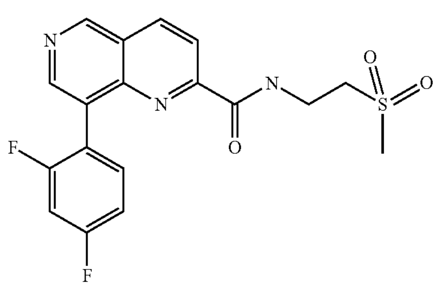 [SMILES: CS(=O)(=O)CCNC(=O)c1ccc2cncc(-c3ccc(F)cc3F)c2n1] | 8-(2,4-Difluorophenyl)-N-(2-(methylsulfonyl)ethyl)-1,6-naphthyridine-2-carboxamide | 0.06 |
| 130 | 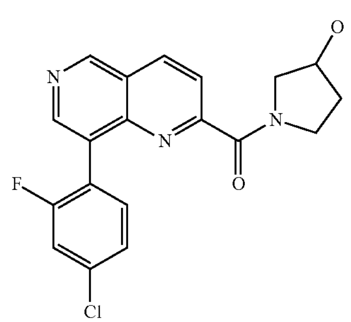 [SMILES: O=C(c1ccc2cncc(-c3ccc(Cl)cc3F)c2n1)N1CCC(O)C1] | (8-(4-Chloro-2-fluorophenyl)-1,6-naphthyridin-2-yl)(3-hydroxypyrrolidin-1-yl)methanone | 0.13 |
| 131 | 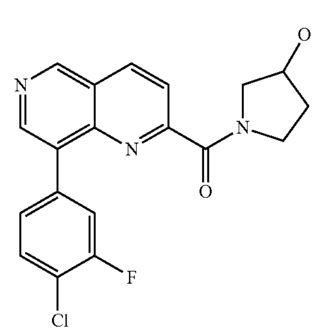 [SMILES: O=C(c1ccc2cncc(-c3ccc(Cl)c(F)c3)c2n1)N1CCC(O)C1] | (8-(4-Chloro-3-fluorophenyl)-1,6-naphthyridin-2-yl)(3-hydroxypyrrolidin-1-yl)methanone | 0.07 |

TABLE 1-continued

List of examples and EC₁₅₀ data of novel compounds

| Example | Structure | Name | EC$_{150}$ (uM) |
|---|---|---|---|
| 132 | 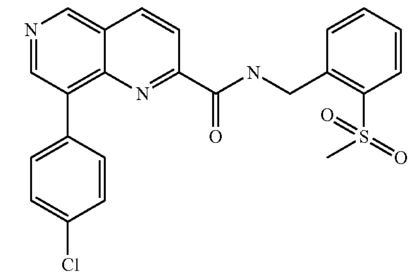 [SMILES: CS(=O)(=O)c1ccccc1CNC(=O)c1ccc2cncc(-c3ccc(Cl)cc3)c2n1] | 8-(4-Chlorophenyl)-N-(2-(methylsulfonyl)benzyl)-1,6-naphthyridine-2-carboxamide | 0.03 |
| 133 | 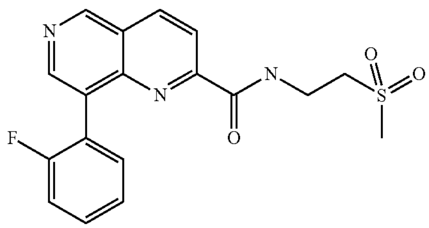 [SMILES: CS(=O)(=O)CCNC(=O)c1ccc2cncc(-c3ccccc3F)c2n1] | 8-(2-Fluorophenyl)-N-(2-(methylsulfonyl)ethyl)-1,6-naphthyridine-2-carboxamide | 0.23 |
| 134 | 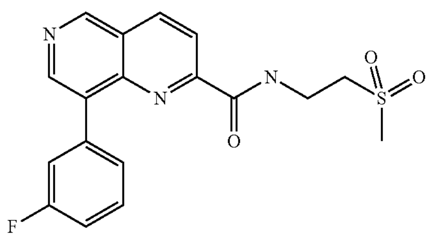 [SMILES: CS(=O)(=O)CCNC(=O)c1ccc2cncc(-c3cccc(F)c3)c2n1] | 8-(3-Fluorophenyl)-N-(2-(methylsulfonyl)ethyl)-1,6-naphthyridine-2-carboxamide | 0.22 |
| 135 | 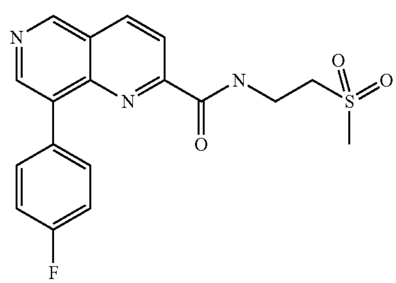 [SMILES: CS(=O)(=O)CCNC(=O)c1ccc2cncc(-c3ccc(F)cc3)c2n1] | 8-(4-Fluorophenyl)-N-(2-(methylsulfonyl)ethyl)-1,6-naphthyridine-2-carboxamide | 0.08 |
| 136 | 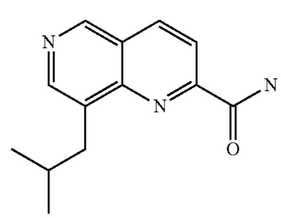 [SMILES: CC(C)Cc1cncc2ccc(C(N)=O)nc12] | 8-Isobutyl-1,6-naphthyridine-2-carboxamide | 0.04 |
| 137 | 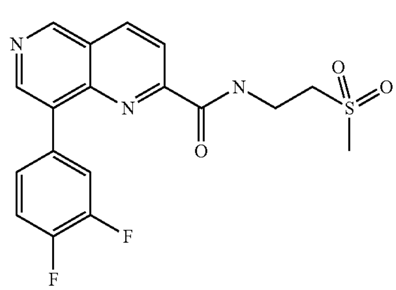 [SMILES: CS(=O)(=O)CCNC(=O)c1ccc2cncc(-c3ccc(F)c(F)c3)c2n1] | 8-(3,4-Difluorophenyl)-N-(2-(methylsulfonyl)ethyl)-1,6-naphthyridine-2-carboxamide | 0.35 |

TABLE 1-continued

List of examples and EC$_{150}$ data of novel compounds

| Example | Structure | Name | EC$_{150}$ (uM) |
|---|---|---|---|
| 138 | 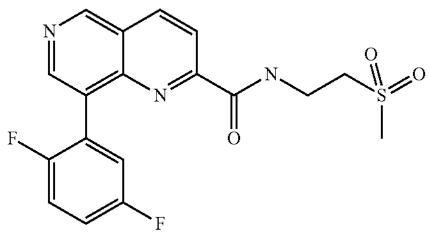 [SMILES: CS(=O)(=O)CCNC(=O)c1ccc2cncc(-c3cc(F)ccc3F)c2n1] | 8-(2,5-Difluorophenyl)-N-(2-(methylsulfonyl)ethyl)-1,6-naphthyridine-2-carboxamide | 0.26 |
| 139 | 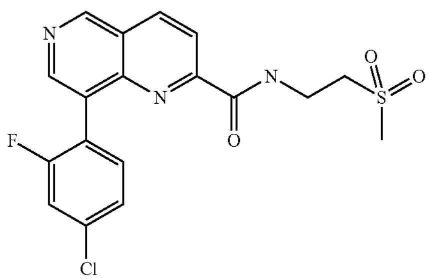 | 8-(4-Chloro-2-fluorophenyl)-N-(2-(methylsulfonyl)ethyl)-1,6-naphthyridine-2-carboxamide | 0.06 |
| 140 | 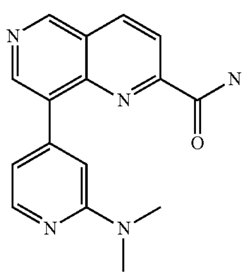 [SMILES: CN(C)c1cc(-c2cncc3ccc(C(N)=O)nc23)ccn1] | 8-(2-(Dimethylamino)pyridin-4-yl)-1,6-naphthyridine-2-carboxamide | 0.147 |
| 141 | 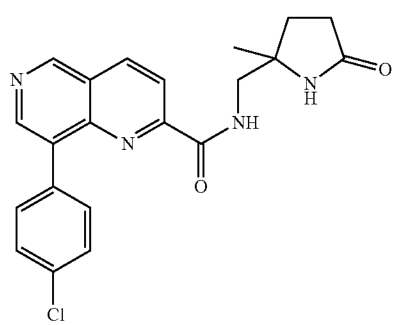 [SMILES: CC1(CNC(=O)c2ccc3cncc(-c4ccc(Cl)cc4)c3n2)CCC(=O)N1] | 8-(4-Chlorophenyl)-N-((2-methyl-5-oxopyrrolidin-2-yl)methyl)-1,6-naphthyridine-2-carboxamide | 0.01 |
| 142 | 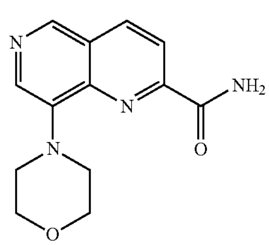 [SMILES: NC(=O)c1ccc2cncc(N3CCOCC3)c2n1] | 8-Morpholino-1,6-naphthyridine-2-carboxamide | 0.94 |

TABLE 1-continued

List of examples and EC$_{150}$ data of novel compounds

| Example | Structure | Name | EC$_{150}$ (uM) |
|---|---|---|---|
| 143 | 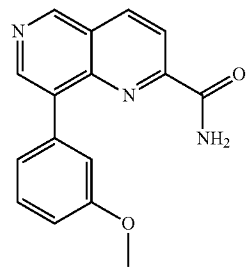 [SMILES: COc1cccc(-c2cncc3ccc(C(N)=O)nc23)c1] | 8-(3-Methoxyphenyl)-1,6-naphthyridine-2-carboxamide | 0.24 |
| 144 | 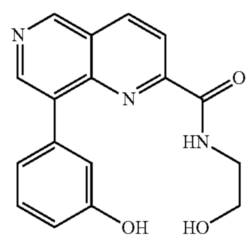 [SMILES: O=C(NCCO)c1ccc2cncc(-c3cccc(O)c3)c2n1] | N-(2-Hydroxyethyl)-8-(3-hydroxyphenyl)-1,6-naphthyridine-2-carboxamide | 0.16 |
| 145 | 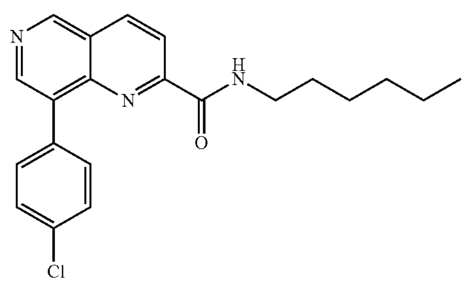 [SMILES: CCCCCCNC(=O)c1ccc2cncc(-c3ccc(Cl)cc3)c2n1] | 8-(4-Chlorophenyl)-N-hexyl-1,6-naphthyridine-2-carboxamide | 0.21 |
| 146 | 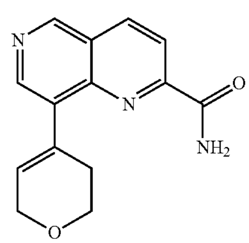 [SMILES: NC(=O)c1ccc2cncc(C3=CCOCC3)c2n1] | 8-(3,6-Dihydro-2H-pyran-4-yl)-1,6-naphthyridine-2-carboxamide | 0.21 |
| 147 | 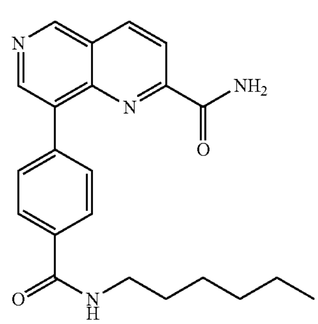 [SMILES: CCCCCCNC(=O)c1ccc(-c2cncc3ccc(C(N)=O)nc23)cc1] | 8-(4-(Hexylcarbamoyl)phenyl)-1,6-naphthyridine-2-carboxamide | 0.09 |

TABLE 1-continued

List of examples and EC$_{150}$ data of novel compounds

| Example | Structure | Name | EC$_{150}$ (uM) |
|---|---|---|---|
| 148 | 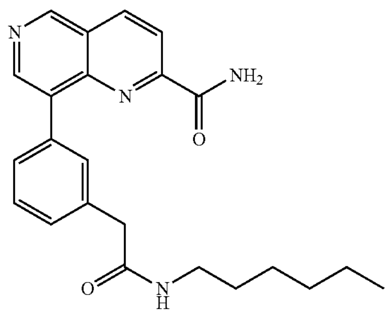 [SMILES: CCCCCCNC(=O)Cc1cccc(-c2cncc3ccc(C(N)=O)nc23)c1] | 8-(3-(2-(Hexylamino)-2-oxoethyl)phenyl)-1,6-naphthyridine-2-carboxamide | 0.18 |
| 149 | 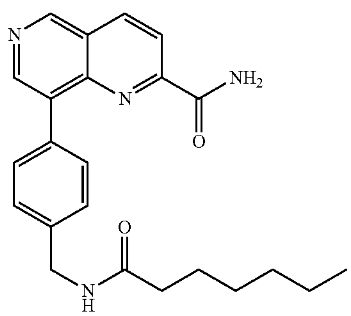 [SMILES: CCCCCCC(=O)NCc1ccc(-c2cncc3ccc(C(N)=O)nc23)cc1] | 8-(4-(Heptanamidomethyl)phenyl)-1,6-naphthyridine-2-carboxamide | 0.07 |
| 150 | 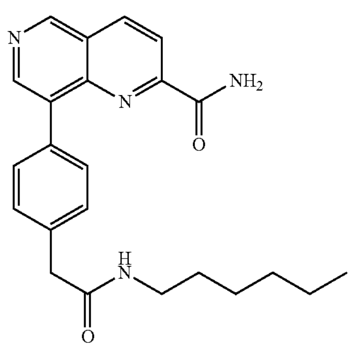 [SMILES: CCCCCCNC(=O)Cc1ccc(-c2cncc3ccc(C(N)=O)nc23)cc1] | 8-(4-(2-(Hexylamino)-2-oxoethyl)phenyl)-1,6-naphthyridine-2-carboxamide | 0.04 |
| 151 | 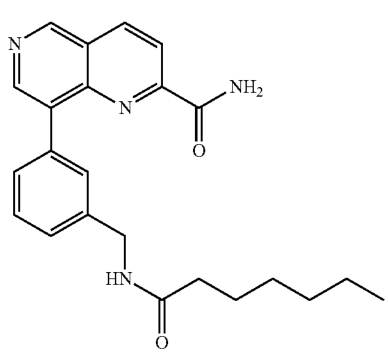 [SMILES: CCCCCCC(=O)NCc1cccc(-c2cncc3ccc(C(N)=O)nc23)c1] | 8-(3-(Heptanamidomethyl)phenyl)-1,6-naphthyridine-2-carboxamide | 0.03 |

TABLE 1-continued

List of examples and EC$_{150}$ data of novel compounds

| Example | Structure | Name | EC$_{150}$ (uM) |
|---|---|---|---|
| 152 | 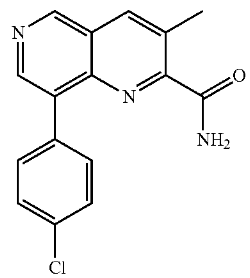 [SMILES: Cc1cc2cncc(-c3ccc(Cl)cc3)c2nc1C(N)=O] | 8-(4-Chlorophenyl)-3-methyl-1,6-naphthyridine-2-carboxamide | 0.34 |
| 153 | 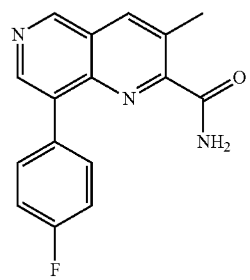 [SMILES: Cc1cc2cncc(-c3ccc(F)cc3)c2nc1C(N)=O] | 8-(4-Fluorophenyl)-3-methyl-1,6-naphthyridine-2-carboxamide | 0.79 |
| 154 | 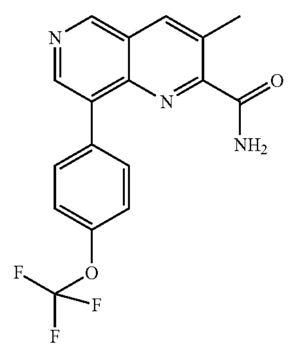 [SMILES: Cc1cc2cncc(-c3ccc(OC(F)(F)F)cc3)c2nc1C(N)=O] | 3-Methyl-8-(4-(trifluoromethoxy)phenyl)-1,6-naphthyridine-2-carboxamide | 2.19 |
| 155 | 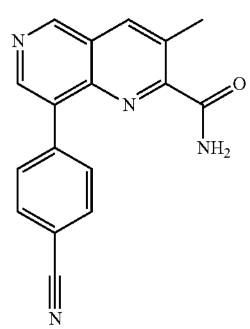 [SMILES: Cc1cc2cncc(-c3ccc(C#N)cc3)c2nc1C(N)=O] | 8-(4-Cyanophenyl)-3-methyl-1,6-naphthyridine-2-carboxamide | 0.7 |
| 156 | 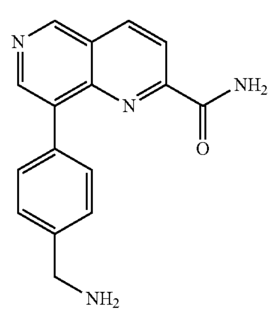 [SMILES: NCc1ccc(-c2cncc3ccc(C(N)=O)nc23)cc1] | 8-(4-(Aminomethyl)phenyl)-1,6-naphthyridine-2-carboxamide | 0.31 |

TABLE 1-continued

List of examples and EC$_{150}$ data of novel compounds

| Example | Structure | Name | EC$_{150}$ (uM) |
|---|---|---|---|
| 157 | 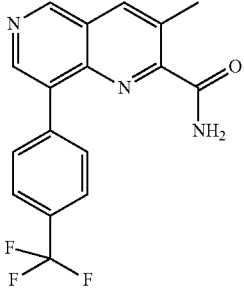 [SMILES: Cc1cc2cncc(-c3ccc(C(F)(F)F)cc3)c2nc1C(N)=O] | 3-Methyl-8-[4-(trifluoromethyl)phenyl]-1,6-naphthyridine-2-carboxamide | 0.88 |
| 158 | 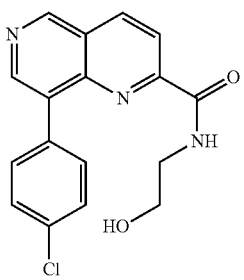 | 8-(4-Chlorophenyl)-N-(2-hydroxyethyl)-1,6-naphthyridine-2-carboxamide | 0.09 |
| 159 | 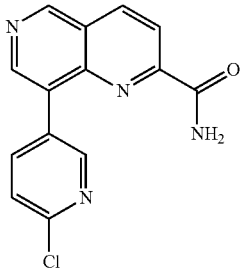 [SMILES: NC(=O)c1ccc2cncc(-c3ccc(Cl)nc3)c2n1] | 8-(6-Chloropyridin-3-yl)-1,6-naphthyridine-2-carboxamide | 0.18 |
| 160 | 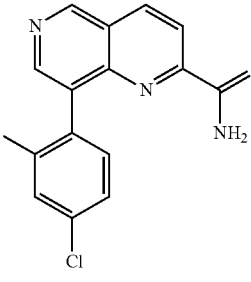 | 8-(2,4-Dichlorophenyl)-1,6-naphthyridine-2-carboxamide | 0.1 |
| 161 | 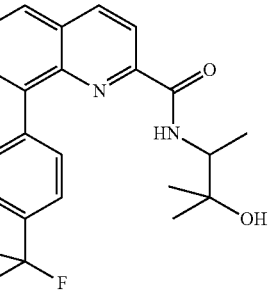 | N-(3-Hydroxy-3-methylbutan-2-yl)-8-(4-(trifluoromethyl)phenyl)-1,6-naphthyridine-2-carboxamide | 0.06 |

TABLE 1-continued

List of examples and EC$_{150}$ data of novel compounds

| Example | Structure | Name | EC$_{150}$ (uM) |
| --- | --- | --- | --- |
| 162 | 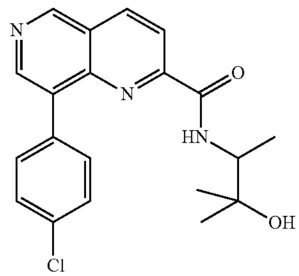 [SMILES: CC(NC(=O)c1ccc2cncc(-c3ccc(Cl)cc3)c2n1)C(C)(C)O] | 8-(4-Chlorophenyl)-N-(3-hydroxy-3-methylbutan-2-yl)-1,6-naphthyridine-2-carboxamide | 0.06 |
| 163 | 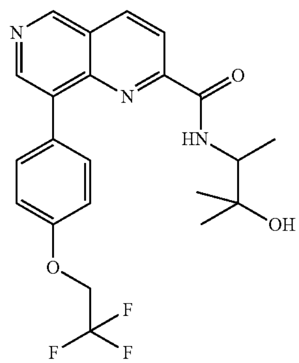 [SMILES: CC(NC(=O)c1ccc2cncc(-c3ccc(OCC(F)(F)F)cc3)c2n1)C(C)(C)O] | N-(3-Hydroxy-3-methylbutan-2-yl)-8-(4-(2,2,2-trifluoroethoxy)phenyl)-1,6-naphthyridine-2-carboxamide | 0.07 |
| 164 | 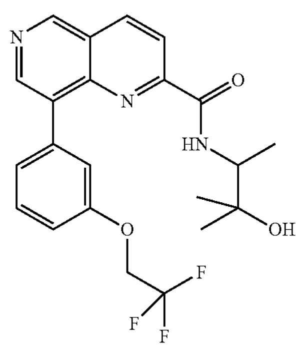 [SMILES: CC(NC(=O)c1ccc2cncc(-c3cccc(OCC(F)(F)F)c3)c2n1)C(C)(C)O] | N-(3-Hydroxy-3-methylbutan-2-yl)-8-(3-(2,2,2-trifluoroethoxy)phenyl)-1,6-naphthyridine-2-carboxamide | 0.76 |
| 165 | 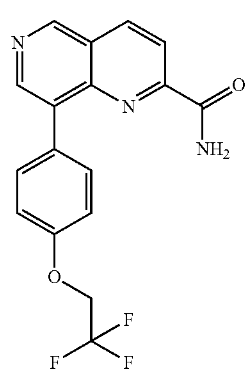 [SMILES: NC(=O)c1ccc2cncc(-c3ccc(OCC(F)(F)F)cc3)c2n1] | 8-(4-(2,2,2-Trifluoroethoxy)phenyl)-1,6-naphthyridine-2-carboxamide | 0.01 |

TABLE 1-continued

List of examples and EC$_{150}$ data of novel compounds

| Example | Structure | Name | EC$_{150}$ (uM) |
| --- | --- | --- | --- |
| 166 | 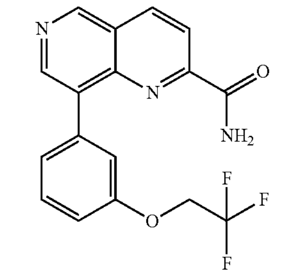 [SMILES: NC(=O)c1ccc2cncc(-c3cccc(OCC(F)(F)F)c3)c2n1] | 8-(3-(2,2,2-Trifluoroethoxy)phenyl)-1,6-naphthyridine-2-carboxamide | 0.06 |
| 167 | 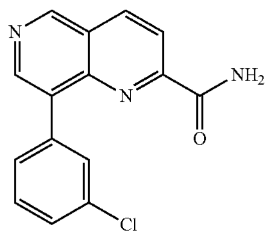 [SMILES: NC(=O)c1ccc2cncc(-c3cccc(Cl)c3)c2n1] | 8-(3-Chlorophenyl)-1,6-naphthyridine-2-carboxamide | 0.09 |
| 168 | 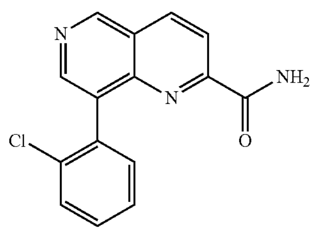 [SMILES: NC(=O)c1ccc2cncc(-c3ccccc3Cl)c2n1] | 8-(2-Chlorophenyl)-1,6-naphthyridine-2-carboxamide | 0.15 |
| 169 | 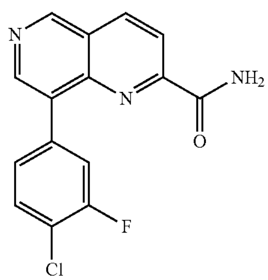 [SMILES: NC(=O)c1ccc2cncc(-c3ccc(Cl)c(F)c3)c2n1] | 8-(4-Chloro-3-fluorophenyl)-1,6-naphthyridine-2-carboxamide | 0.03 |
| 170 | 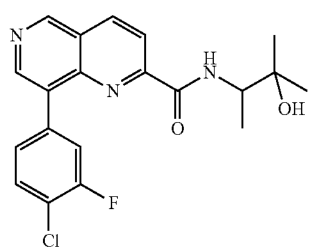 [SMILES: CC(NC(=O)c1ccc2cncc(-c3ccc(Cl)c(F)c3)c2n1)C(C)(C)O] | 8-(4-Chloro-3-fluorophenyl)-N-(3-hydroxy-3-methylbutan-2-yl)-1,6-naphthyridine-2-carboxamide | 0.25 |
| 171 | 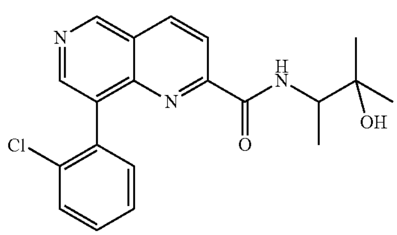 [SMILES: CC(NC(=O)c1ccc2cncc(-c3ccccc3Cl)c2n1)C(C)(C)O] | 8-(2-Chlorophenyl)-N-(3-hydroxy-3-methylbutan-2-yl)-1,6-naphthyridine-2-carboxamide | 0.12 |

TABLE 1-continued

List of examples and EC$_{150}$ data of novel compounds

| Example | Structure | Name | EC$_{150}$ (uM) |
|---|---|---|---|
| 172 | 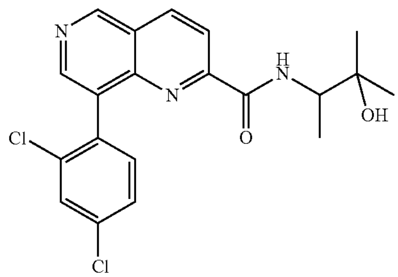 [SMILES: CC(NC(=O)c1ccc2cncc(-c3ccc(Cl)cc3Cl)c2n1)C(C)(C)O] | 8-(2,4-Dichlorophenyl)-N-(3-hydroxy-3-methylbutan-2-yl)-1,6-naphthyridine-2-carboxamide | 0.5 |
| 173 | 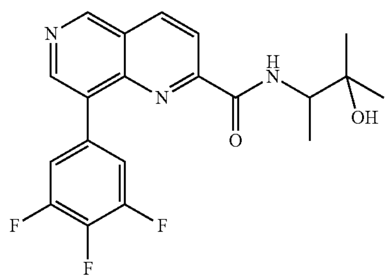 [SMILES: CC(NC(=O)c1ccc2cncc(-c3cc(F)c(F)c(F)c3)c2n1)C(C)(C)O] | N-(3-Hydroxy-3-methylbutan-2-yl)-8-(3,4,5-trifluorophenyl)-1,6-naphthyridine-2-carboxamide | 0.9 |
| 174 | 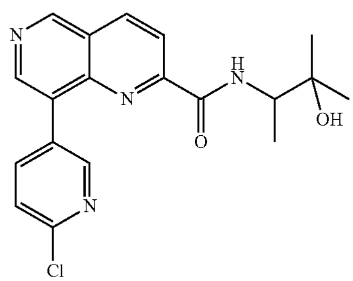 [SMILES: CC(NC(=O)c1ccc2cncc(-c3ccc(Cl)nc3)c2n1)C(C)(C)O] | 8-(6-Chloropyridin-3-yl)-N-(3-hydroxy-3-methylbutan-2-yl)-1,6-naphthyridine-2-carboxamide | 0.61 |
| 175 | 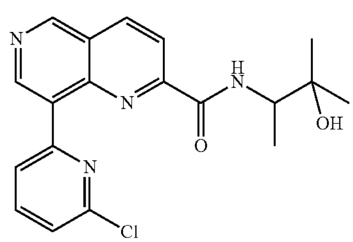 [SMILES: CC(NC(=O)c1ccc2cncc(-c3cccc(Cl)n3)c2n1)C(C)(C)O] | 8-(6-Chloropyridin-2-yl)-N-(3-hydroxy-3-methylbutan-2-yl)-1,6-naphthyridine-2-carboxamide | 1.03 |
| 176 | 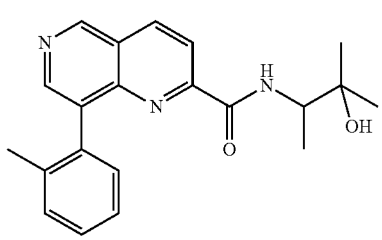 [SMILES: Cc1ccccc1-c1cncc2ccc(C(=O)NC(C)C(C)(C)O)nc12] | N-(3-Hydroxy-3-methylbutan-2-yl)-8-o-tolyl-1,6-naphthyridine-2-carboxamide | 0.28 |

TABLE 1-continued

List of examples and EC150 data of novel compounds

| Example | Structure | Name | EC150 (uM) |
|---|---|---|---|
| 177 | 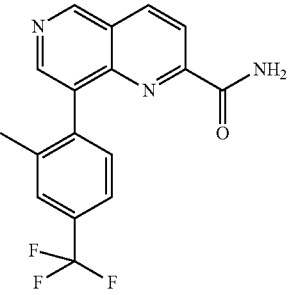 [SMILES: Cc1cc(C(F)(F)F)ccc1-c1cncc2ccc(C(N)=O)nc12] | 8-(2-Methyl-4-(trifluoromethyl)phenyl)-1,6-naphthyridine-2-carboxamide | — |

TABLE 2

List of examples and EC150 data of known compounds

| Example | Structure | Name | EC150 (uM) |
|---|---|---|---|
| 178 | 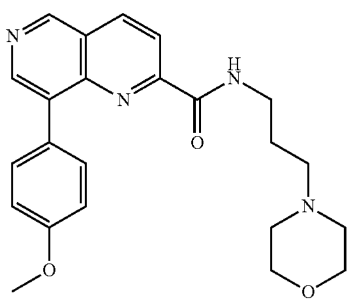 [SMILES: COc1ccc(-c2cncc3ccc(C(=O)NCCCN4CCOCC4)nc23)cc1] | 8-(4-Methoxy-phenyl)-[1,6]naphthyridine-2-carboxylic acid (3-imidazol-1-yl-propyl)-amide | 2.5 |
| 179 | 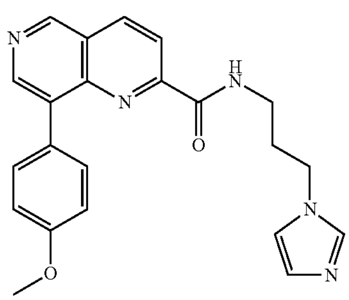 [SMILES: COc1ccc(-c2cncc3ccc(C(=O)NCCCn4ccnc4)nc23)cc1] | 8-(4-Methoxy-phenyl)-[1,6]naphthyridine-2-carboxylic acid (3-imidazol-1-yl-propyl)-amide | 0.7 |
| 180 | 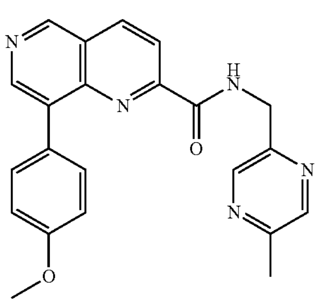 [SMILES: COc1ccc(-c2cncc3ccc(C(=O)NCc4cnc(C)cn4)nc23)cc1] | 8-(4-Methoxy-phenyl)-[1,6]naphthyridine-2-carboxylic acid (5-methyl-pyrazin-2-ylmethyl)-amide | 1.26 |

TABLE 2-continued

List of examples and EC$_{150}$ data of known compounds

| Example | Structure | Name | EC$_{150}$ (uM) |
|---|---|---|---|
| 181 | 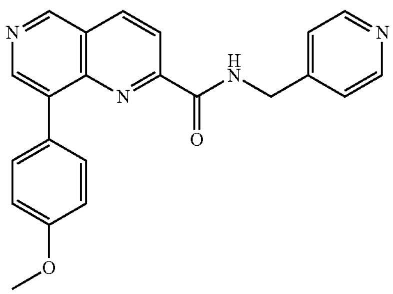 [SMILES: COc1ccc(-c2cncc3ccc(C(=O)NCc4ccncc4)nc23)cc1] | 8-(4-Methoxy-phenyl)-[1,6]naphthyridine-2-carboxylic acid (pyridin-4-ylmethyl)-amide | 0.04 |
| 182 | 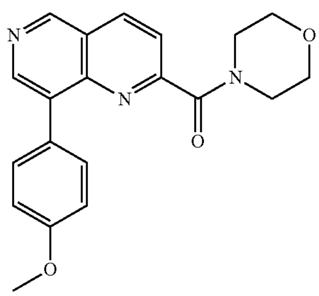 [SMILES: COc1ccc(-c2cncc3ccc(C(=O)N4CCOCC4)nc23)cc1] | [8-(4-Methoxy-phenyl)-[1,6]naphthyridin-2-yl]-morpholin-4-yl-methanone | 5.4 |
| 183 | 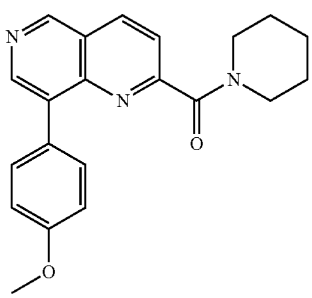 [SMILES: COc1ccc(-c2cncc3ccc(C(=O)N4CCCCC4)nc23)cc1] | [8-(4-Methoxy-phenyl)-[1,6]naphthyridin-2-yl]-piperidin-1-yl-methanone | 1.25 |
| 184 | 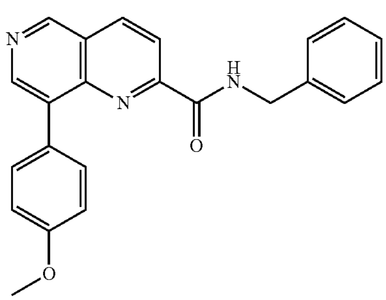 [SMILES: COc1ccc(-c2cncc3ccc(C(=O)NCc4ccccc4)nc23)cc1] | 8-(4-Methoxy-phenyl)-[1,6]naphthyridine-2-carboxylic acid benzylamide | 0.16 |
| 185 | 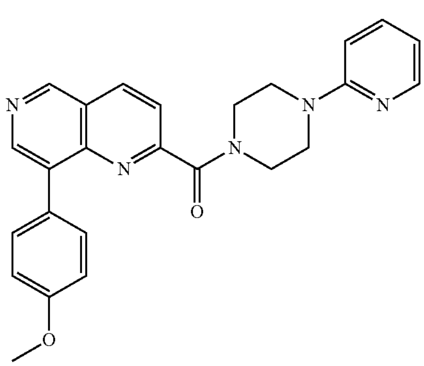 [SMILES: COc1ccc(-c2cncc3ccc(C(=O)N4CCN(c5ccccn5)CC4)nc23)cc1] | [8-(4-Methoxy-phenyl)-[1,6]naphthyridin-2-yl]-(4-pyridin-2-yl-piperazin-1-yl)-methanone | 0.8 |

TABLE 2-continued

List of examples and EC$_{150}$ data of known compounds

| Example | Structure | Name | EC$_{150}$ (uM) |
|---|---|---|---|
| 186 | 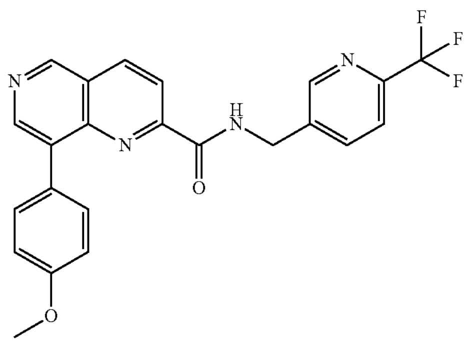 [SMILES: COc1ccc(-c2cncc3ccc(C(=O)NCc4ccc(C(F)(F)F)nc4)nc23)cc1] | 8-(4-Methoxy-phenyl)-[1,6]naphthyridine-2-carboxylic acid (6-trifluoromethyl-pyridin-3-ylmethyl)-amide | 0.67 |
| 187 | 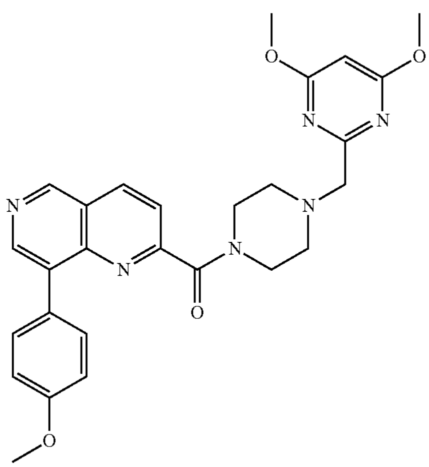 [SMILES: COc1ccc(-c2cncc3ccc(C(=O)N4CCN(Cc5nc(OC)cc(OC)n5)CC4)nc23)cc1] | [4-(4,6-Dimethoxy-pyrimidin-2-ylmethyl)-piperazin-1-yl]-[8-(4-methoxy-phenyl)-[1,6]naphthyridin-2-yl]-methanone | 0.71 |
| 188 | 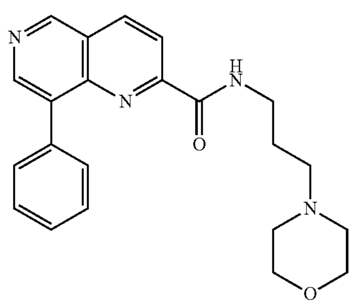 [SMILES: O=C(NCCCN1CCOCC1)c1ccc2cncc(-c3ccccc3)c2n1] | 8-Phenyl-[1,6]naphthyridine-2-carboxylic acid (3-morpholin-4-yl-propyl)-amide | 6.8 |
| 189 | 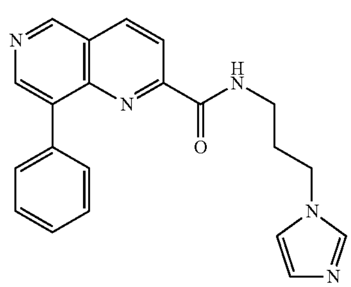 [SMILES: O=C(NCCCn1ccnc1)c1ccc2cncc(-c3ccccc3)c2n1] | 8-Phenyl-[1,6]naphthyridine-2-carboxylic acid (3-imidazol-1-yl-propyl)-amide | 1.2 |

TABLE 2-continued

List of examples and EC$_{150}$ data of known compounds

| Example | Structure | Name | EC$_{150}$ (uM) |
|---|---|---|---|
| 190 | 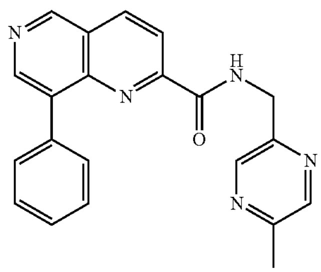 [SMILES: Cc1cnc(CNC(=O)c2ccc3cncc(-c4ccccc4)c3n2)cn1] | 8-Phenyl-[1,6]naphthyridine-2-carboxylic acid (5-methyl-pyrazin-2-ylmethyl)-amide | 0.5 |
| 191 | 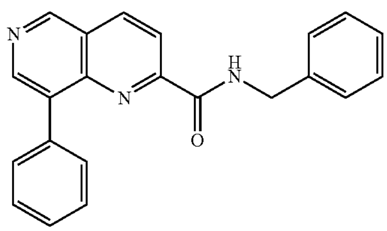 [SMILES: O=C(NCc1ccccc1)c1ccc2cncc(-c3ccccc3)c2n1] | 8-Phenyl-[1,6]naphthyridine-2-carboxylic acid benzylamide | 0.44 |
| 192 | 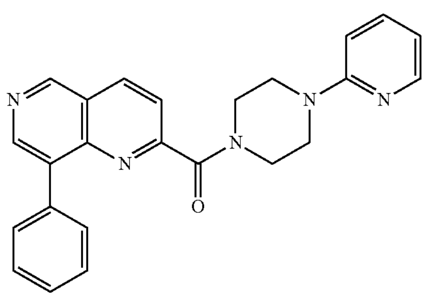 [SMILES: O=C(c1ccc2cncc(-c3ccccc3)c2n1)N1CCN(c2ccccn2)CC1] | (8-Phenyl-[1,6]naphthyridin-2-yl)-(4-pyridin-2-yl-piperazin-1-yl)-methanone | 1.4 |
| 193 | 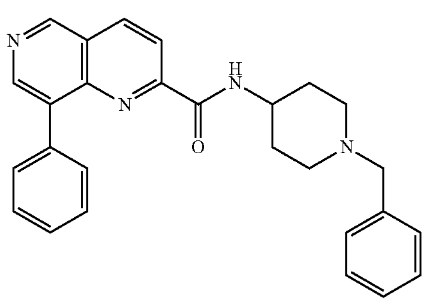 [SMILES: O=C(NC1CCN(Cc2ccccc2)CC1)c1ccc2cncc(-c3ccccc3)c2n1] | 8-Phenyl-[1,6]naphthyridine-2-carboxylic acid (1-benzyl-piperidin-4-yl)-amide | 1.9 |
| 194 | 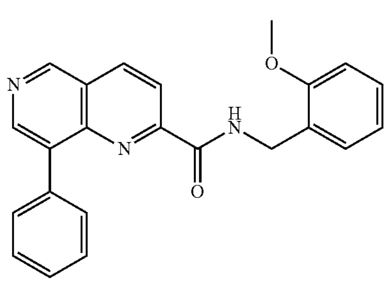 [SMILES: COc1ccccc1CNC(=O)c1ccc2cncc(-c3ccccc3)c2n1] | 8-Phenyl-[1,6]naphthyridine-2-carboxylic acid 2-methoxy-benzylamide | 0.73 |

TABLE 2-continued

List of examples and EC$_{150}$ data of known compounds

| Example | Structure | Name | EC$_{150}$ (uM) |
|---|---|---|---|
| 195 | 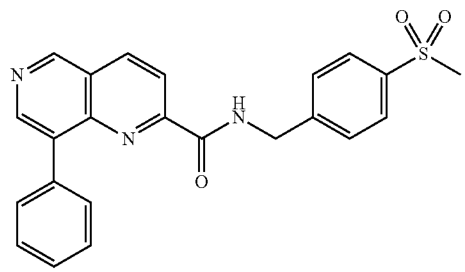 [SMILES: CS(=O)(=O)c1ccc(CNC(=O)c2ccc3cncc(-c4ccccc4)c3n2)cc1] | 8-Phenyl-[1,6]naphthyridine-2-carboxylic acid 4-methanesulfonyl-benzylamide | 4.0 |
| 196 | 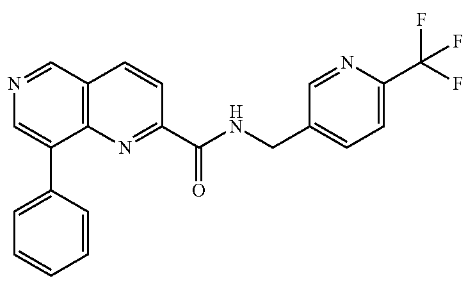 [SMILES: O=C(NCc1ccc(C(F)(F)F)nc1)c1ccc2cncc(-c3ccccc3)c2n1] | 8-Phenyl-[1,6]naphthyridine-2-carboxylic acid (6-trifluoromethyl-pyridin-3-ylmethyl)-amide | 3.7 |
| 197 | 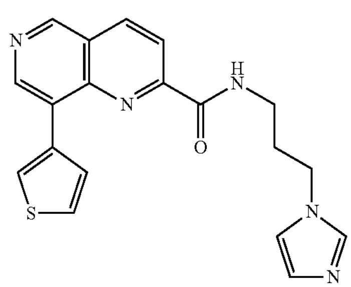 [SMILES: O=C(NCCCn1ccnc1)c1ccc2cncc(-c3ccsc3)c2n1] | 8-Thiophen-3-yl-[1,6]naphthyridine-2-carboxylic acid (3-imidazol-1-yl-propyl)-amide | 1.98 |
| 198 | 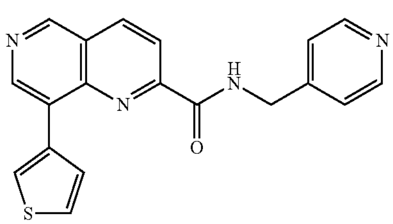 [SMILES: O=C(NCc1ccncc1)c1ccc2cncc(-c3ccsc3)c2n1] | 8-Thiophen-3-yl-[1,6]naphthyridine-2-carboxylic acid (pyridin-4-ylmethyl)-amide | 0.12 |
| 199 | 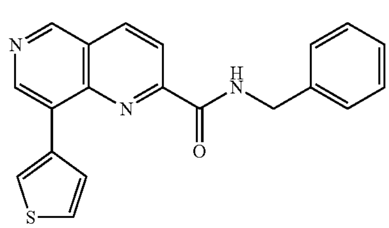 [SMILES: O=C(NCc1ccccc1)c1ccc2cncc(-c3ccsc3)c2n1] | 8-Thiophen-3-yl-[1,6]naphthyridine-2-carboxylic acid benzylamide | 0.1 |

TABLE 2-continued

List of examples and $EC_{150}$ data of known compounds

| Example | Structure | Name | $EC_{150}$ (uM) |
|---|---|---|---|
| 200 | 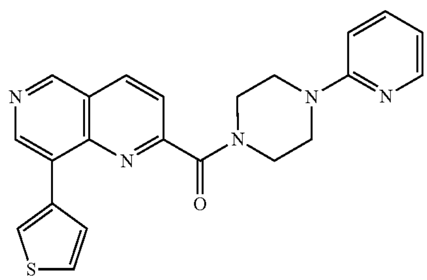 [SMILES: O=C(c1ccc2cncc(-c3ccsc3)c2n1)N1CCN(c2ccccn2)CC1] | (4-Pyridin-2-yl-piperazin-1-yl)-(8-thiophen-3-yl-[1,6]naphthyridin-2-yl)-methanone | 0.8 |
| 201 | 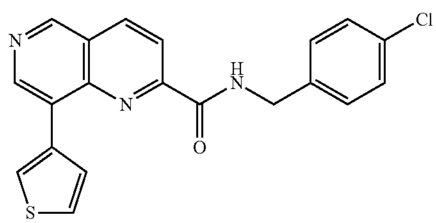 [SMILES: O=C(NCc1ccc(Cl)cc1)c1ccc2cncc(-c3ccsc3)c2n1] | 8-Thiophen-3-yl-[1,6]naphthyridine-2-carboxylic acid 4-chloro-benzylamide | 0.8 |
| 202 | 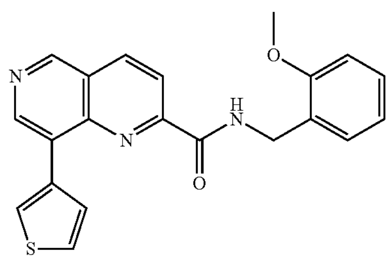 [SMILES: COc1ccccc1CNC(=O)c1ccc2cncc(-c3ccsc3)c2n1] | 8-Thiophen-3-yl-[1,6]naphthyridine-2-carboxylic acid 2-methoxy-benzylamide | 0.15 |
| 203 | 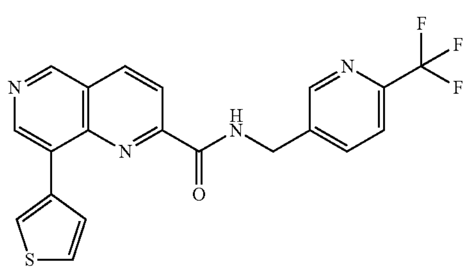 [SMILES: O=C(NCc1ccc(C(F)(F)F)nc1)c1ccc2cncc(-c3ccsc3)c2n1] | 8-Thiophen-3-yl-[1,6]naphthyridine-2-carboxylic acid (6-trifluoromethyl-pyridin-3-ylmethyl)-amide | 1.5 |
| 204 | 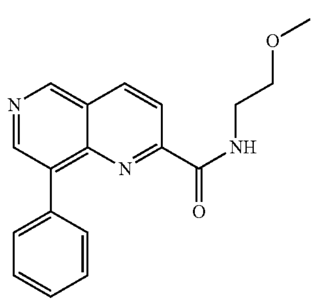 [SMILES: COCCNC(=O)c1ccc2cncc(-c3ccccc3)c2n1] | 8-Phenyl-[1,6]naphthyridine-2-carboxylic acid (2-methoxy-ethyl)-amide | 0.2 |

TABLE 2-continued

List of examples and EC$_{150}$ data of known compounds

| Example | Structure | Name | EC$_{150}$ (uM) |
|---|---|---|---|
| 205 | 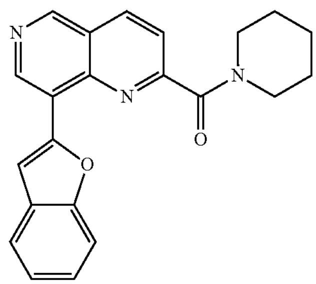 [SMILES: O=C(c1ccc2cncc(-c3cc4ccccc4o3)c2n1)N1CCCCC1] | (8-Benzofuran-2-yl-[1,6]naphthyridin-2-yl)-piperidin-1-yl-methanone | 3.5 |
| 206 | 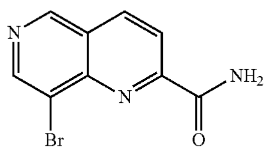 [SMILES: NC(=O)c1ccc2cncc(Br)c2n1] | 8-Bromo-1,6-naphthyridine-2-carboxamide | 0.8 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

8-Bromo-N-(2-methoxyethyl)-1,6-naphthyridine-2-carboxamide

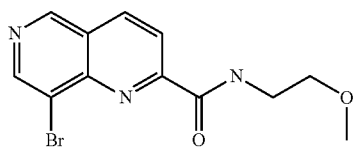 [SMILES: COCCNC(=O)c1ccc2cncc(Br)c2n1]

A mixture of 8-bromo-1,6-naphthyridine-2-carboxylic acid (CAS 197507-55-4, 0.30 g, 1.19 mmol), N,N-diisopropylethylamine (0.19 g, 0.25 ml, 1.45 mmol) and O-(7-azabenzotriazol-1-yl)-N,N,N',N'-tetramethyluronium hexafluorophosphate (HATU, 0.55 g, 1.45 mmol) in dimethylformamide (5.0 ml) was stirred at room temperature for 10 minutes. 2-Methoxyethanamine (0.09 g, 102 µl, 1.19 mmol) was added and stirring was continued over the weekend. Extraction with water/ethyl acetate and chromatography (silica gel, ethyl acetate/heptane=50:50 to 100:0) yielded the title compound as yellow solid (0.36 g, 98%). MS: m/e=310.3, 312.3 [M+H]$^+$.

EXAMPLE 2

N-(2-Methoxyethyl)-8-(4-methoxyphenyl)-1,6-naphthyridine-2-carboxamide

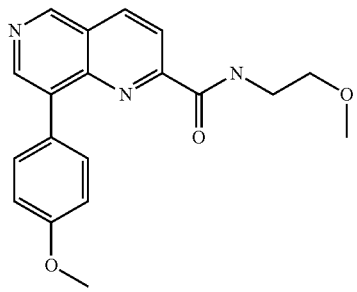 [SMILES: COCCNC(=O)c1ccc2cncc(-c3ccc(OC)cc3)c2n1]

To a suspension of 8-bromo-N-(2-methoxyethyl)-1,6-naphthyridine-2-carboxamide (0.10 g, 0.32 mmol) and 4-methoxyphenylboronic acid (0.05 g, 0.32 mmol) and cesium carbonate (0.12 g, 0.36 mmol) in dioxane (10 ml) and water (1 ml) was added bis(diphenylphosphino)ferrocene-palladium(II)dichloride (0.01 g, 0.02 mmol). The mixture was stirred at 80° C. for 3 hours. Removal of the solvent by distillation and chromatography (silica gel, ethyl acetate/heptane=0:100 to 100:0) and trituration with diethyl ether/pentane (1:1) yielded the title compound as light brown solid (0.09 g, 84%). MS: m/e=338.3 [M+H]$^+$.

EXAMPLE 3

N-(2-Methoxyethyl)-8-(3-methoxyphenyl)-1,6-naphthyridine-2-carboxamide

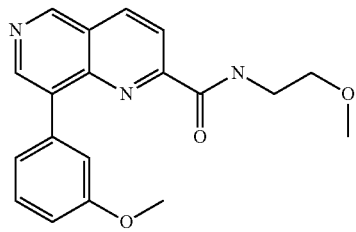 [SMILES: COCCNC(=O)c1ccc2cncc(-c3cccc(OC)c3)c2n1]

To a suspension of 8-bromo-N-(2-methoxyethyl)-1,6-naphthyridine-2-carboxamide (0.04 g, 0.13 mmol) and 3-methoxyphenylboronic acid (0.02 g, 0.13 mmol) and cesium carbonate (0.05 g, 0.14 mmol) in dioxane (7 ml) and water (1 ml) was added bis(diphenylphosphino)ferrocene-palladium(II)dichloride (0.005 g, 0.01 mmol). The mixture was stirred at 80° C. for 3 hours. Removal of the solvent by distillation and chromatography (silica gel, ethyl acetate/heptane=0:100 to 100:0) and trituration with diethyl ether yielded the title compound as light brown solid (0.03 g, 67%). MS: m/e=338.5 [M+H]$^+$.

EXAMPLE 4

N-(2-Methoxyethyl)-1,6-naphthyridine-2-carboxamide

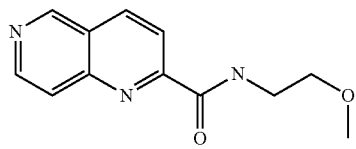 [SMILES: COCCNC(=O)c1ccc2cnccc2n1]

A mixture of 1,6-naphthyridine-2-carboxylic acid (CAS197507-59-8, 0.10 g, 0.57 mmol), N,N-diisopropylethylamine (0.09 g, 0.12 ml, 0.70 mmol) and O-(7-azabenzotriazol-1-yl)-N,N,N',N'-tetramethyluronium hexafluorophosphate (HATU, 0.27 g, 0.70 mmol) in dimethylformamide (1.4 ml) was stirred at room temperature for 2 minutes. 2-Methoxyethanamine (0.04 g, 0.05 ml, 0.57 mmol) was added and stirring was continued for 2 hours. Extraction with water/ethyl acetate and chromatography (silica gel, ethyl acetate/heptane=50:50 to 100:0) yielded the title compound as light yellow solid (0.09 g, 69%). MS: m/e=232.4 [M+H]$^+$.

EXAMPLE 5

N-(2-Methoxyethyl)-8-(2-methoxyphenyl)-1,6-naphthyridine-2-carboxamide

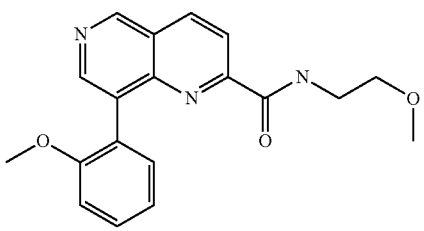

To a suspension of 8-bromo-N-(2-methoxyethyl)-1,6-naphthyridine-2-carboxamide (0.04 g, 0.13 mmol) and 2-methoxyphenylboronic acid (0.02 g, 0.13 mmol) and cesium carbonate (0.05 g, 0.14 mmol) in dioxane (7 ml) and water (1 ml) was added bis(diphenylphosphino)ferrocene-palladium(II)dichloride (0.005 g, 0.01 mmol). The mixture was stirred at 80° C. for 3 hours. Removal of the solvent by distillation and chromatography (silica gel, ethyl acetate/heptane=0:100 to 100:0) and trituration with diethyl ether/pentane yielded the title compound as light brown oil (0.03 g, 76%). MS: m/e=338.7 [M+H]$^+$.

EXAMPLE 6

8-(4-Chlorophenyl)-N-(2-methoxyethyl)-1,6-naphthyridine-2-carboxamide

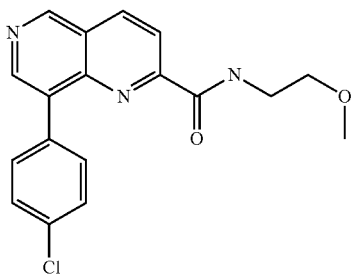

To a suspension of 8-bromo-N-(2-methoxyethyl)-1,6-naphthyridine-2-carboxamide (0.07 g, 0.23 mmol) and 4-chlorophenylboronic acid (0.04 g, 0.23 mmol) and cesium carbonate (0.08 g, 0.25 mmol) in dioxane (7 ml) and water (1 ml) was added bis(diphenylphosphino)ferrocene-palladium(II)dichloride (0.01 g, 0.01 mmol). The mixture was stirred at 80° C. for 15 hours. Removal of the solvent by distillation and chromatography (silica gel, ethyl acetate/heptane=50:50 to 100:0) and trituration with diethyl ether yielded the title compound as light brown solid (0.05 g, 70%). MS: m/e=342.2 [M+H]$^+$.

EXAMPLE 7

8-(3-Chlorophenyl)-N-(2-methoxyethyl)-1,6-naphthyridine-2-carboxamide

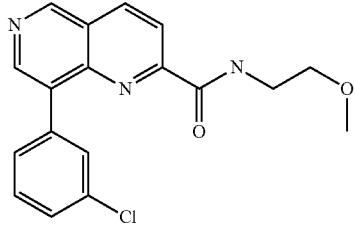 [SMILES: COCCNC(=O)c1ccc2cncc(-c3cccc(Cl)c3)c2n1]

To a suspension of 8-bromo-N-(2-methoxyethyl)-1,6-naphthyridine-2-carboxamide (0.07 g, 0.23 mmol) and 3-chlorophenylboronic acid (0.04 g, 0.23 mmol) and cesium carbonate (0.08 g, 0.25 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=50:50 to 100:0) and trituration with diethyl ether yielded the title compound as off-white solid (0.03 g, 44%). MS: m/e=342.4 [M+H]$^+$.

EXAMPLE 8

8-(2-Chlorophenyl)-N-(2-methoxyethyl)-1,6-naphthyridine-2-carboxamide

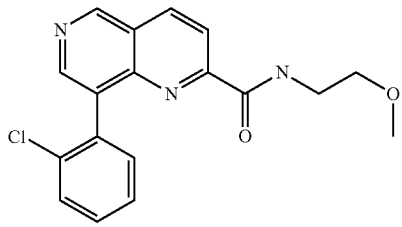 [SMILES: COCCNC(=O)c1ccc2cncc(-c3ccccc3Cl)c2n1]

To a suspension of 8-bromo-N-(2-methoxyethyl)-1,6-naphthyridine-2-carboxamide (0.07 g, 0.23 mmol) and 2-chlorophenylboronic acid (0.04 g, 0.23 mmol) and cesium carbonate (0.08 g, 0.25 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=50:50 to 100:0) and trituration with diethyl ether/pentane yielded the title compound as light brown solid (0.04 g, 56%). MS: m/e=342.3 [M+H]$^+$.

EXAMPLE 9

8-Bromo-[1,6]naphthyridine-2-carboxylic acid (pyridin-4-ylmethyl)-amide

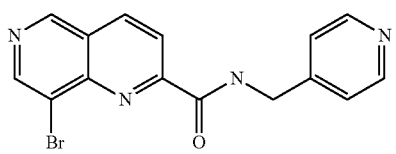 [SMILES: O=C(NCc1ccncc1)c1ccc2cncc(Br)c2n1]

A mixture of 8-bromo-1,6-naphthyridine-2-carboxylic acid (0.50 g, 1.98 mmol), N,N-diisopropylethylamine (0.31 g, 0.42 ml, 2.41 mmol) and O-(7-azabenzotriazol-1-yl)-N,N,N',N'-tetramethyluronium hexafluorophosphate (HATU, 0.92 g, 2.41 mmol) in dimethylformamide (5.0 ml) was stirred at room temperature for 2 minutes. Pyridin-4-ylmethanamine (0.21 g, 0.20 ml, 1.98 mmol) was added and stirring was continued over the weekend. Extraction with water/ethyl acetate and chromatography (silica gel, ethyl acetate/heptane=50:50 to 100:0) yielded the title compound as yellow solid (0.43 g, 63%). MS: m/e=343.4, 345.3 [M+H]$^+$.

EXAMPLE 10

N-Benzyl-8-bromo-1,6-naphthyridine-2-carboxamide

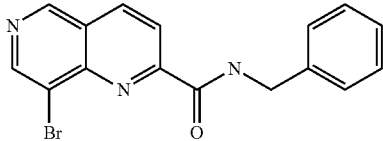 [SMILES: O=C(NCc1ccccc1)c1ccc2cncc(Br)c2n1]

A mixture of 8-bromo-1,6-naphthyridine-2-carboxylic acid (0.50 g, 1.98 mmol), N,N-diisopropylethylamine (0.31 g, 0.42 ml, 2.41 mmol) and O-(7-azabenzotriazol-1-yl)-N,N,N',N'-tetramethyluronium hexafluorophosphate (HATU, 0.92 g, 2.41 mmol) in dimethylformamide (5.0 ml) was stirred at room temperature for 2 minutes. Phenylmethanamine (0.21 g, 0.22 ml, 1.98 mmol) was added and stirring was continued over the weekend. Extraction with water/ethyl acetate and chromatography (silica gel, ethyl acetate/heptane=50:50 to 100:0) yielded the title compound as light brown solid (0.75 g, 99%). MS: m/e=342.3, 344.3 [M+H]$^+$.

EXAMPLE 11

N-Benzyl-8-(3-methoxyphenyl)-1,6-naphthyridine-2-carboxamide

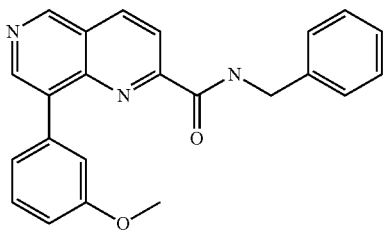 [SMILES: COc1cccc(-c2cncc3ccc(C(=O)NCc4ccccc4)nc23)c1]

To a suspension of N-benzyl-8-bromo-1,6-naphthyridine-2-carboxamide (0.07 g, 0.21 mmol) and 3-methoxyphenylboronic acid (0.03 g, 0.21 mmol) and cesium carbonate (0.07 g, 0.23 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=0:100 to 100:0) and trituration with diethyl ether/pentane yielded the title compound as light yellow solid (0.05 g, 70%). MS: m/e=370.5 [M+H]$^+$.

EXAMPLE 12

N-Benzyl-8-(2-methoxyphenyl)-1,6-naphthyridine-2-carboxamide

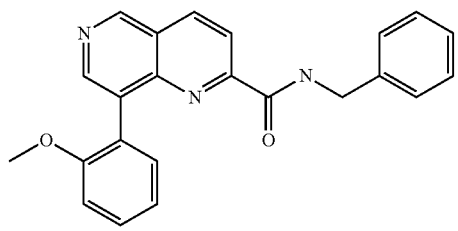 [SMILES: COc1ccccc1-c1cncc2ccc(C(=O)NCc3ccccc3)nc12]

To a suspension of N-benzyl-8-bromo-1,6-naphthyridine-2-carboxamide (0.07 g, 0.21 mmol) and 2-methoxyphenylboronic acid (0.03 g, 0.21 mmol) and cesium carbonate (0.07 g, 0.23 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=0:100 to 100:0) and trituration with diethyl ether/pentane yielded the title compound as light brown solid (0.04 g, 46%). MS: m/e=370.3 [M+H]$^+$.

EXAMPLE 13

N-Benzyl-8-(4-chlorophenyl)-1,6-naphthyridine-2-carboxamide

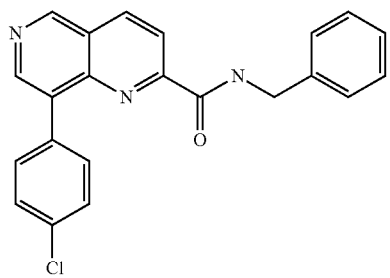 [SMILES: O=C(NCc1ccccc1)c1ccc2cncc(-c3ccc(Cl)cc3)c2n1]

To a suspension of N-benzyl-8-bromo-1,6-naphthyridine-2-carboxamide (0.07 g, 0.21 mmol) and 4-chlorophenylboronic acid (0.03 g, 0.21 mmol) and cesium carbonate (0.07 g, 0.23 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=0:100 to 100:0) and trituration with diethyl ether/pentane yielded the title compound as light brown solid (0.05 g, 67%). MS: m/e=374.4 [M+H]$^+$.

EXAMPLE 14

N-Benzyl-8-(3-chlorophenyl)-1,6-naphthyridine-2-carboxamide

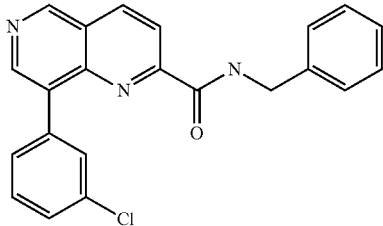 [SMILES: O=C(NCc1ccccc1)c1ccc2cncc(-c3cccc(Cl)c3)c2n1]

To a suspension of N-benzyl-8-bromo-1,6-naphthyridine-2-carboxamide (0.07 g, 0.21 mmol) and 3-chlorophenylboronic acid (0.03 g, 0.21 mmol) and cesium carbonate (0.07 g, 0.23 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=0:100 to 100:0) and trituration with diethyl ether/pentane yielded the title compound as light brown solid (0.04 g, 50%). MS: m/e=374.4 [M+H]$^+$.

EXAMPLE 15

N-Benzyl-8-(2-chlorophenyl)-1,6-naphthyridine-2-carboxamide

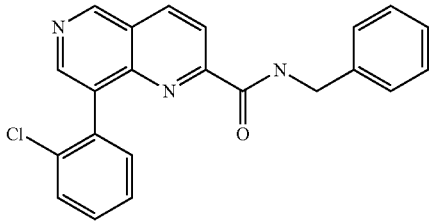 [SMILES: O=C(NCc1ccccc1)c1ccc2cncc(-c3ccccc3Cl)c2n1]

To a suspension of N-benzyl-8-bromo-1,6-naphthyridine-2-carboxamide (0.07 g, 0.21 mmol) and 2-chlorophenylboronic acid (0.03 g, 0.21 mmol) and cesium carbonate (0.07 g, 0.23 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=0:100 to 100:0) and trituration with diethyl ether/pentane yielded the title compound as light brown solid (0.04 g, 57%). MS: m/e=374.4 [M+H]$^+$.

EXAMPLE 16

N-Benzyl-8-(pyridin-4-yl)-1,6-naphthyridine-2-carboxamide

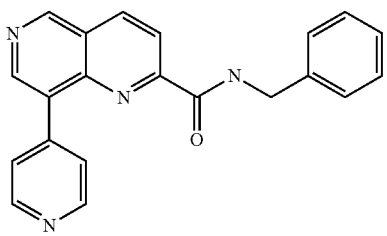 [SMILES: O=C(NCc1ccccc1)c1ccc2cncc(-c3ccncc3)c2n1]

To a suspension of N-benzyl-8-bromo-1,6-naphthyridine-2-carboxamide (0.07 g, 0.21 mmol) and pyridin-4-ylboronic acid (0.03 g, 0.21 mmol) and cesium carbonate (0.07 g, 0.23 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=0:100 to 100:0) and trituration with diethyl ether/pentane yielded the title compound as light brown solid (0.03 g, 47%). MS: m/e=341.4 [M+H]$^+$.

EXAMPLE 17

N-Benzyl-8-(pyridin-3-yl)-1,6-naphthyridine-2-carboxamide

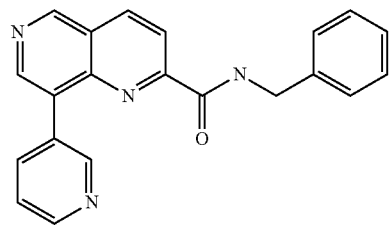 [SMILES: O=C(NCc1ccccc1)c1ccc2cncc(-c3cccnc3)c2n1]

To a suspension of N-benzyl-8-bromo-1,6-naphthyridine-2-carboxamide (0.07 g, 0.21 mmol) and pyridin-3-ylboronic acid (0.03 g, 0.21 mmol) and cesium carbonate (0.07 g, 0.23 mmol) in dioxane (7 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=0:100 to 100:0) and trituration with diethyl ether/pentane yielded the title compound as light brown solid (0.05 g, 70%). MS: m/e=341.7 [M+H]$^+$.

EXAMPLE 18

N-(2-Methoxyethyl)-8-(pyridin-4-yl)-1,6-naphthyridine-2-carboxamide

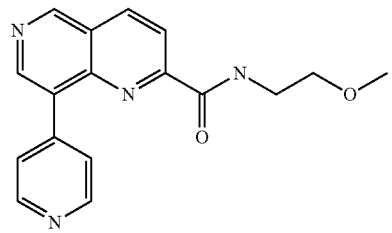 [SMILES: COCCNC(=O)c1ccc2cncc(-c3ccncc3)c2n1]

To a suspension of 8-bromo-N-(2-methoxyethyl)-1,6-naphthyridine-2-carboxamide (0.08 g, 0.26 mmol) and pyridin-4-ylboronic acid (0.03 g, 0.26 mmol) and cesium carbonate (0.09 g, 0.28 mmol) in dioxane (10 ml) and water (1 ml) was added bis(diphenylphosphino)ferrocene-palladium (II)dichloride (0.01 g, 0.01 mmol). The mixture was stirred at 80° C. for 3 hours. Removal of the solvent by distillation and chromatography (silica gel, methanol/dichloromethane=0:100 to 20:80) and trituration with diethyl ether yielded the title compound as light brown solid (0.06 g, 72%). MS: m/e=309.7 [M+H]⁺.

EXAMPLE 19

N-(2-methoxyethyl)-8-(pyridin-3-yl)-1,6-naphthyridine-2-carboxamide

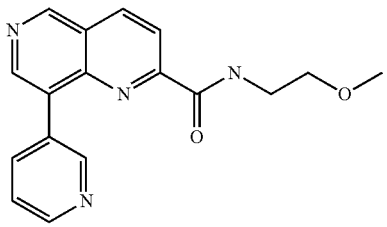 [SMILES: COCCNC(=O)c1ccc2cncc(-c3cccnc3)c2n1]

To a suspension of 8-bromo-N-(2-methoxyethyl)-1,6-naphthyridine-2-carboxamide (0.08 g, 0.26 mmol) and pyridin-3-ylboronic acid (0.03 g, 0.26 mmol) and cesium carbonate (0.09 g, 0.28 mmol) in dioxane (10 ml) and water (1 ml) was added bis(diphenylphosphino)ferrocene-palladium (II)dichloride (0.01 g, 0.01 mmol). The mixture was stirred at 80° C. for 3 hours. Removal of the solvent by distillation and chromatography (silica gel, methanol/dichloromethane=0:100 to 20:80) and trituration with diethyl ether yielded the title compound as light brown solid (0.03 g, 34%). MS: m/e=309.2 [M+H]⁺.

EXAMPLE 20

8-(4-Methoxyphenyl)-N-phenethyl-1,6-naphthyridine-2-carboxamide

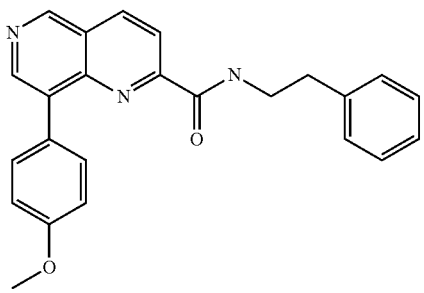 [SMILES: COc1ccc(-c2cncc3ccc(C(=O)NCCc4ccccc4)nc23)cc1]

a) 8-(4-Methoxyphenyl)-1,6-naphthyridine-2-carboxylic acid

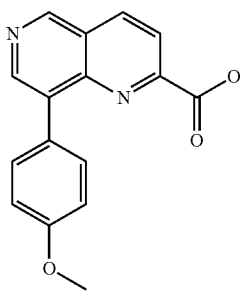 [SMILES: COc1ccc(-c2cncc3ccc(C(=O)O)nc23)cc1]

To a suspension of methyl-8-bromo-1,6-naphthyridine-2-carboxylate (CAS 875514-20-8, 0.74 g, 0.2.77 mmol) and 4-methoxyphenylboronic acid (0.42 g, 2.77 mmol) and cesium carbonate (0.99 g, 3.05 mmol) in dioxane (50 ml) and water (5 ml) was added bis(diphenylphosphino)ferrocene-palladium(II)dichloride (0.10 g, 0.14 mmol). The mixture was stirred at 80° C. for 15 hours. Removal of the solvent by distillation and chromatography (silica gel, ethyl acetate/heptane=40:60 to 100:0) yielded the title compound as brown solid (1.16, quant.). MS: m/e=281.1 [M+H]⁺.

b) 8-(4-Methoxyphenyl)-N-phenethyl-1,6-naphthyridine-2-carboxamide

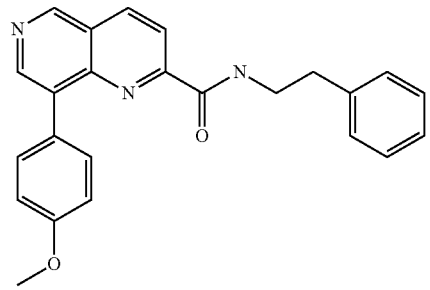 [SMILES: COc1ccc(-c2cncc3ccc(C(=O)NCCc4ccccc4)nc23)cc1]

A mixture of 8-(4-methoxyphenyl)-1,6-naphthyridine-2-carboxylic acid (0.10 g, 0.29 mmol), N, N-diisopropylethylamine (0.05 g, 0.06 ml, 0.35 mmol) and O-(7-azabenzotriazol-1-yl)-N,N,N',N'-tetramethyluronium hexafluorophosphate (HATU, 0.13 g, 0.35 mmol) in dimethylformamide (2 ml) was stirred at room temperature for 10 minutes. 2-Phenylethanamine (0.04 g, 0.04 ml, 0.29 mmol) was added and stirring was continued overnight. Extraction with water/ethyl acetate and chromatography (silica gel, ethyl acetate/heptane=50:50 to 100:0) and trituration with diethyl ether/pentane yielded the title compound as yellow solid (0.09 g, 83%). MS: m/e=384.4 [M+H]⁺.

EXAMPLE 21

8-(4-Methoxyphenyl)-1,6-naphthyridine-2-carboxamide

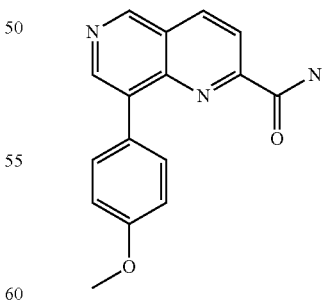

A mixture of 8-(4-methoxyphenyl)-1,6-naphthyridine-2-carboxylic acid (0.10 g, 0.29 mmol), 1,1'-carbonyldiimidazole (0.05 g, 0.31 mmol) in dichloromethane (5 ml) was stirred at room temperature for 30 minutes. A solution of ammonia in methanol (0.05 ml, 0.32 mmol) was added and stirring was continued overnight. Extraction with water/ ethyl acetate and chromatography (silica gel, ethyl acetate/heptane=50:50 to 100:0) and trituration with diethyl ether/pentane yielded the title compound as yellow solid (0.01 g, 15%). MS: m/e=280.4 [M+H]$^+$.

EXAMPLE 22

8-(4-Methoxyphenyl)-N-(pyridin-3-ylmethyl)-1,6-naphthyridine-2-carboxamide

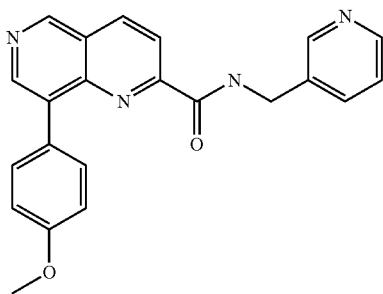 [SMILES: COc1ccc(-c2cncc3ccc(C(=O)NCc4cccnc4)nc23)cc1]

A mixture of 8-(4-methoxyphenyl)-1,6-naphthyridine-2-carboxylic acid (0.10 g, 0.29 mmol), N, N-diisopropylethylamine (0.05 g, 0.06 ml, 0.35 mmol) and O-(7-azabenzotriazol-1-yl)-N,N,N',N'-tetramethyluronium hexafluorophosphate (HATU, 0.13 g, 0.35 mmol) in dimethylformamide (3 ml) was stirred at room temperature for 10 minutes. Pyridin-3-ylmethanamine (0.03 g, 0.03 ml, 0.29 mmol) was added and stirring was continued overnight. Extraction with water/ethyl acetate and chromatography (silica gel, ethyl acetate/heptane=50:50 to 100:0) and trituration with diethyl ether yielded the title compound as yellow solid (0.06 g, 59%). MS: m/e=371.5 [M+H]$^+$.

EXAMPLE 23

8-(4-Methoxyphenyl)-N-(pyridin-2-ylmethyl)-1,6-naphthyridine-2-carboxamide

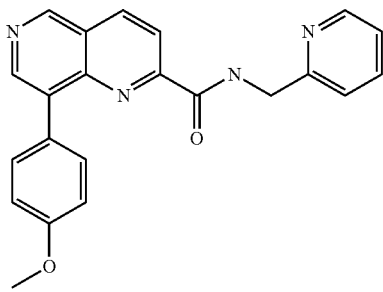 [SMILES: COc1ccc(-c2cncc3ccc(C(=O)NCc4ccccn4)nc23)cc1]

A mixture of 8-(4-methoxyphenyl)-1,6-naphthyridine-2-carboxylic acid (0.10 g, 0.29 mmol), N,N-diisopropylethylamine (0.05 g, 0.06 ml, 0.35 mmol) and O-(7-azabenzotriazol-1-yl)-N,N,N',N'-tetramethyluronium hexafluorophosphate (HATU, 0.13 g, 0.35 mmol) in dimethylformamide (3 ml) was stirred at room temperature for 10 minutes. Pyridin-2-ylmethanamine (0.03 g, 0.03 ml, 0.29 mmol) was added and stirring was continued overnight. Extraction with water/ethyl acetate and chromatography (silica gel, ethyl acetate/heptane=50:50 to 100:0) and trituration with diethyl ether yielded the title compound as yellow solid (0.07 g, 69%). MS: m/e=371.5 [M+H]$^+$.

EXAMPLE 24

N-Benzyl-8-(4-methylpyridin-2-yl)-1,6-naphthyridine-2-carboxamide

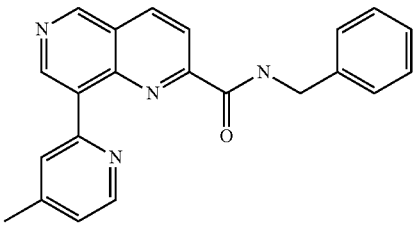 [SMILES: Cc1ccnc(-c2cncc3ccc(C(=O)NCc4ccccc4)nc23)c1]

To a suspension of N-benzyl-8-bromo-1,6-naphthyridine-2-carboxamide (0.10 g, 0.29 mmol) and 4-methyl-2-(4,4,5,5-tetramethyl-1,3,2-dioxaborolan-2-yl)pyridine (0.06 g, 0.29 mmol) and cesium carbonate (0.11 g, 0.32 mmol) in dioxane (10 ml) and water (1 ml) was added bis(diphenylphosphino)ferrocene-palladium(II)dichloride (0.01 g, 0.01 mmol). The mixture was stirred at 80° C. for 15 hours. Removal of the solvent by distillation and chromatography (silica gel, methanol/dichloromethane=0:100 to 30:70) and trituration with diethyl ether/pentane yielded the title compound as light black solid (0.03 g, 32%). MS: m/e=355.4 [M+H]$^+$.

EXAMPLE 25

8-(4-Methoxyphenyl)-N-(3-phenylpropyl)-1,6-naphthyridine-2-carboxamide

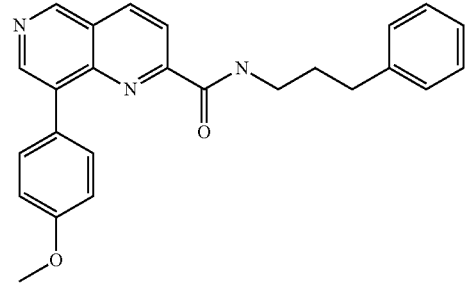

A mixture of 8-(4-methoxyphenyl)-1,6-naphthyridine-2-carboxylic acid (0.10 g, 0.29 mmol), N, N-diisopropylethylamine (0.05 g, 0.06 ml, 0.35 mmol) and O-(7-azabenzotriazol-1-yl)-N,N,N',N'-tetramethyluronium hexafluorophosphate (HATU, 0.13 g, 0.35 mmol) in dimethylformamide (2 ml) was stirred at room temperature for 10 minutes. 3-Phenylpropan-1-amine (0.04 g, 0.04 ml, 0.29 mmol) was added and stirring was continued for 5 hours. Extraction with water/ethyl acetate and chromatography (silica gel, ethyl acetate/heptane=50:50 to 100:0) and trituration with diethyl ether/pentane yielded the title compound as yellow solid (0.09 g, 78%). MS: m/e=398.5 [M+H]$^+$.

EXAMPLE 26

8-(3-Methoxyphenyl)-N-(pyridin-4-ylmethyl)-1,6-naphthyridine-2-carboxamide

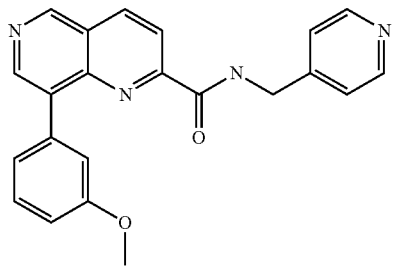 [SMILES: COc1cccc(-c2cncc3ccc(C(=O)NCc4ccncc4)nc23)c1]

To a suspension of 8-bromo-N-(pyridin-4-ylmethyl)-1,6-naphthyridine-2-carboxamide (0.10 g, 0.29 mmol) and 3-methoxyphenylboronic acid (0.04 g, 0.29 mmol) and cesium carbonate (0.11 g, 0.32 mmol) in dioxane (10 ml) and water (1 ml) was added bis(diphenylphosphino)ferrocene-palladium(II)dichloride (0.01 g, 0.01 mmol). The mixture was stirred at 80° C. for 15 hours. Removal of the solvent by distillation and chromatography (silica gel, ethyl acetate/heptane=70:30 to 100:0) and trituration with diethyl ether/pentane yielded the title compound as light black solid (0.08 g, 72%). MS: m/e=371.4 [M+H]$^+$.

EXAMPLE 27

8-(2-Methoxyphenyl)-N-(pyridin-4-ylmethyl)-1,6-naphthyridine-2-carboxamide

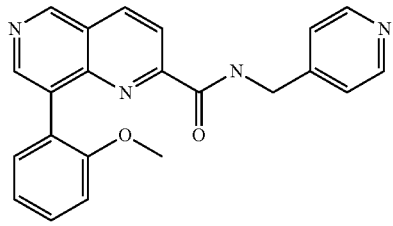 [SMILES: COc1ccccc1-c1cncc2ccc(C(=O)NCc3ccncc3)nc12]

To a suspension of 8-bromo-N-(pyridin-4-ylmethyl)-1,6-naphthyridine-2-carboxamide (0.10 g, 0.29 mmol) and 2-methoxyphenylboronic acid (0.04 g, 0.29 mmol) and cesium carbonate (0.11 g, 0.32 mmol) in dioxane (10 ml) and water (1 ml) was added bis(diphenylphosphino)ferrocene-palladium(II)dichloride (0.01 g, 0.01 mmol). The mixture was stirred at 80° C. for 15 hours. Removal of the solvent by distillation and chromatography (silica gel, ethyl acetate/heptane=70:30 to 100:0) and trituration with diethyl ether/pentane yielded the title compound as light brown solid (0.09 g, 85%). MS: m/e=371.4 [M+H]$^+$.

EXAMPLE 28

8-(4-Chlorophenyl)-N-(pyridin-4-ylmethyl)-1,6-naphthyridine-2-carboxamide

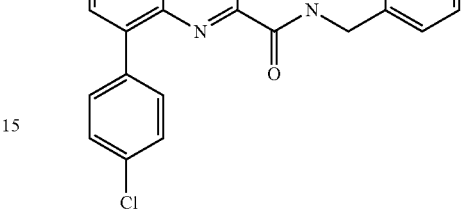

To a suspension of 8-bromo-N-(pyridin-4-ylmethyl)-1,6-naphthyridine-2-carboxamide (0.10 g, 0.29 mmol) and 4-chlorophenylboronic acid (0.05 g, 0.29 mmol) and cesium carbonate (0.11 g, 0.32 mmol) in dioxane (10 ml) and water (1 ml) was added bis(diphenylphosphino)ferrocene-palladium(II)dichloride (0.01 g, 0.01 mmol). The mixture was stirred at 80° C. for 15 hours. Removal of the solvent by distillation and chromatography (silica gel, ethyl acetate/heptane=70:30 to 100:0) and trituration with diethyl ether/pentane yielded the title compound as light brown solid (0.09 g, 78%). MS: m/e=375.4 [M+H]$^+$.

EXAMPLE 29

8-(3-Chlorophenyl)-N-(pyridin-4-ylmethyl)-1,6-naphthyridine-2-carboxamide

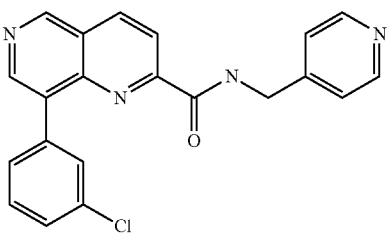 [SMILES: O=C(NCc1ccncc1)c1ccc2cncc(-c3cccc(Cl)c3)c2n1]

To a suspension of 8-bromo-N-(pyridin-4-ylmethyl)-1,6-naphthyridine-2-carboxamide (0.10 g, 0.29 mmol) and 3-chlorophenylboronic acid (0.05 g, 0.29 mmol) and cesium carbonate (0.11 g, 0.32 mmol) in dioxane (10 ml) and water (1 ml) was added bis(diphenylphosphino)ferrocene-palladium(II)dichloride (0.01 g, 0.01 mmol). The mixture was stirred at 80° C. for 15 hours. Removal of the solvent by distillation and chromatography (silica gel, ethyl acetate/heptane=70:30 to 100:0) and trituration with diethyl ether/pentane yielded the title compound as light brown solid (0.09 g, 79%). MS: m/e=375.4 [M+H]$^+$.

EXAMPLE 30

8-(2-Chlorophenyl)-N-(pyridin-4-ylmethyl)-1,6-naphthyridine-2-carboxamide

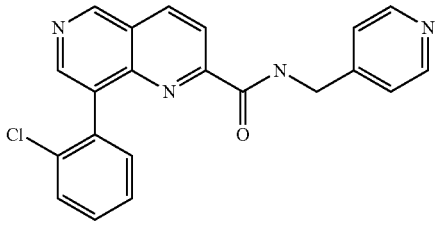 [SMILES: O=C(NCc1ccncc1)c1ccc2cncc(-c3ccccc3Cl)c2n1]

To a suspension of 8-bromo-N-(pyridin-4-ylmethyl)-1,6-naphthyridine-2-carboxamide (0.10 g, 0.29 mmol) and 2-chlorophenylboronic acid (0.05 g, 0.29 mmol) and cesium carbonate (0.11 g, 0.32 mmol) in dioxane (10 ml) and water (1 ml) was added bis(diphenylphosphino)ferrocene-palladium(II)dichloride (0.01 g, 0.01 mmol). The mixture was stirred at 80° C. for 15 hours. Removal of the solvent by distillation and chromatography (silica gel, ethyl acetate/heptane=70:30 to 100:0) and trituration with diethyl ether/pentane yielded the title compound as light brown solid (0.05 g, 41%). MS: m/e=375.4 [M+H]$^+$.

EXAMPLE 31

8-(Pyridin-3-yl)-N-(pyridin-4-ylmethyl)-1,6-naphthyridine-2-carboxamide

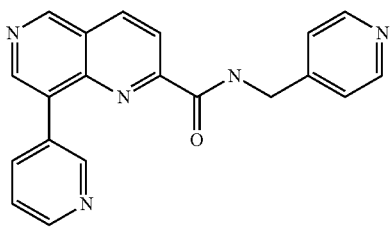 [SMILES: O=C(NCc1ccncc1)c1ccc2cncc(-c3cccnc3)c2n1]

To a suspension of 8-bromo-N-(pyridin-4-ylmethyl)-1,6-naphthyridine-2-carboxamide (0.10 g, 0.29 mmol) and pyridin-3-ylboronic acid (0.04 g, 0.29 mmol) and cesium carbonate (0.11 g, 0.32 mmol) in dioxane (10 ml) and water (1 ml) was added bis(diphenylphosphino)ferrocene-palladium(II)dichloride (0.01 g, 0.01 mmol). The mixture was stirred at 80° C. for 15 hours. Removal of the solvent by distillation and chromatography (silica gel, methanol/dichloromethane=0:100 to 10:90) and trituration with diethyl ether/pentane yielded the title compound as light brown solid (0.07 g, 65%). MS: m/e=342.2 [M+H]$^+$.

EXAMPLE 32

8-(Pyridin-4-yl)-N-(pyridin-4-ylmethyl)-1,6-naphthyridine-2-carboxamide

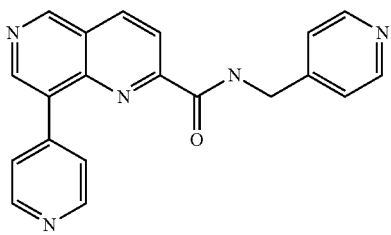 [SMILES: O=C(NCc1ccncc1)c1ccc2cncc(-c3ccncc3)c2n1]

To a suspension of 8-bromo-N-(pyridin-4-ylmethyl)-1,6-naphthyridine-2-carboxamide (0.10 g, 0.29 mmol) and pyridin-4-ylboronic acid (0.04 g, 0.29 mmol) and cesium carbonate (0.11 g, 0.32 mmol) in dioxane (10 ml) and water (1 ml) was added bis(diphenylphosphino)ferrocene-palladium (II)dichloride (0.01 g, 0.01 mmol). The mixture was stirred at 80° C. for 15 hours. Removal of the solvent by distillation and chromatography (silica gel, methanol/dichloromethane=0:100 to 20:80) and trituration with diethyl ether/pentane yielded the title compound as light brown solid (0.04 g, 44%). MS: m/e=342.4 [M+H]$^+$.

EXAMPLE 33

N-Benzyl-8-(4-methoxyphenyl)-N-methyl-1,6-naphthyridine-2-carboxamide

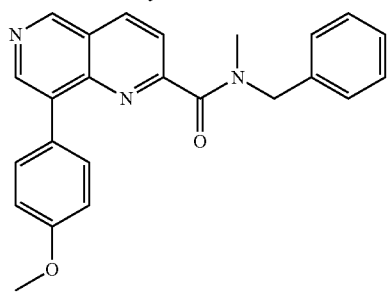

A suspension of 8-(4-methoxyphenyl)-1,6-naphthyridine-2-carboxylic acid (0.10 g, 0.29 mmol) and N-methyl-1-phenylmethanamine (0.04 g, 0.29 mmol) in dichloromethane (10 ml) was cooled to 0° C. and 1-hydroxybenzotriazole hydrate (0.04 g, 0.29 mmol) was added. After stirring for 20 minutes N-(3-dimethylaminopropyl)-N'-ethylcarbodiimide hydrochloride (0.06 g, 0.31 mmol) was added and stirring was continued at room temperature for 3 hours. Removal of the solvent by distillation and chromatography (silica gel, ethyl acetate/heptane=50:50 to 100:0) yielded the title compound as brown oil (0.03 g, 27%). MS: m/e=384.4 [M+H]$^+$.

EXAMPLE 34

N-Benzyl-N-(2-methoxyethyl)-8-(4-methoxyphenyl)-1,6-naphthyridine-2-carboxamide

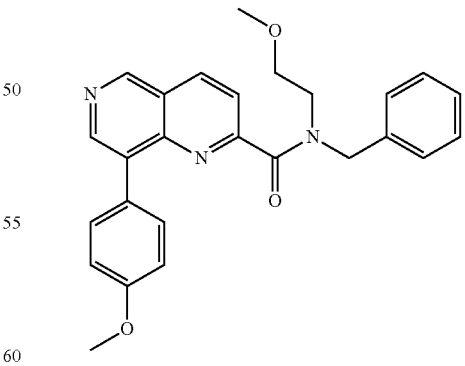

A suspension of 8-(4-methoxyphenyl)-1,6-naphthyridine-2-carboxylic acid (0.10 g, 0.29 mmol) and N-benzyl-2-methoxyethanamine (0.05 g, 0.29 mmol) in dichloromethane (10 ml) was cooled to 0° C. and 1-hydroxybenzotriazole hydrate (0.04 g, 0.29 mmol) was added. After stirring for 20 minutes N-(3-dimethylaminopropyl)-N'-ethylcarbodiimide hydrochloride (0.06 g, 0.31 mmol) was added and stirring was continued at room temperature during the weekend. Removal of the solvent by distillation and chromatography (silica gel, ethyl acetate/heptane=50:50 to 100:0) yielded the title compound as yellow oil (0.06 g, 52%). MS: m/e=428.5 [M+H]+.

EXAMPLE 35

8-(4-Methoxyphenyl)-N-(3,3,3-trifluoropropyl)-1,6-naphthyridine-2-carboxamide

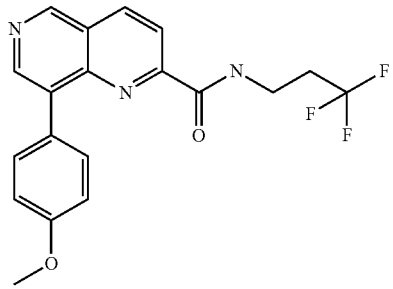 [SMILES: COc1ccc(-c2cncc3ccc(C(=O)NCCC(F)(F)F)nc23)cc1]

A mixture of 8-(4-methoxyphenyl)-1,6-naphthyridine-2-carboxylic acid (0.10 g, 0.29 mmol), N, N-diisopropylethylamine (0.05 g, 61 µl, 0.35 mmol) and O-(7-azabenzotriazol-1-yl)-N,N,N',N'-tetramethyluronium hexafluorophosphate (HATU, 0.13 g, 0.35 mmol) in dimethylformamide (2 ml) was stirred at room temperature for 10 minutes. 3,3,3-Trifluoropropan-1-amine (0.03 g, 0.29 mmol) was added and stirring was continued overnight. Extraction with water/ethyl acetate and chromatography (silica gel, ethyl acetate/heptane=50:50 to 100:0) yielded the title compound as yellow oil (0.08 g, 71%). MS: m/e=376.4 [M+H]+.

EXAMPLE 36

N-(3-(1H-Imidazol-1-yl)propyl)-8-(3-chlorophenyl)-1,6-naphthyridine-2-carboxamide

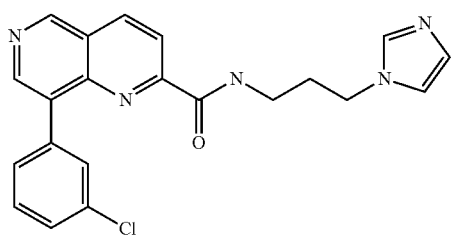 [SMILES: O=C(NCCCn1ccnc1)c1ccc2cncc(-c3cccc(Cl)c3)c2n1]

a) N-(3-(1H-imidazol-1-yl)propyl)-8-bromo-1,6-naphthyridine-2-carboxamide

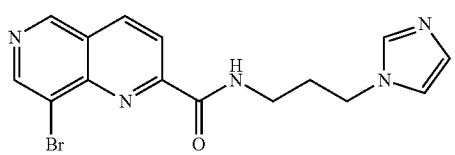 [SMILES: O=C(NCCCn1ccnc1)c1ccc2cncc(Br)c2n1]

A mixture of 8-bromo-1,6-naphthyridine-2-carboxylic acid (0.50 g, 1.98 mmol), N,N-diisopropylethylamine (0.31 g, 0.42 ml, 2.41 mmol) and O-(7-azabenzotriazol-1-yl)-N,N,N',N'-tetramethyluronium hexafluorophosphate (HATU, 0.92 g, 2.41 mmol) in dimethylformamide (5 ml) was stirred at room temperature for 10 minutes. 3-(1H-Imidazol-1-yl)propan-1-amine (0.25 g, 0.24 ml, 1.98 mmol) was added and stirring was continued during the weekend. Extraction with water/ethyl acetate and chromatography (silica gel, methanol/dichloromethane=0:100 to 30:70) yielded the title compound as yellow oil (0.42 g, 59%). MS: m/e=360.4, 362.3 [M+H]+.

b) N-(3-(1H-Imidazol-1-yl)propyl)-8-(3-chlorophenyl)-1,6-naphthyridine-2-carboxamide

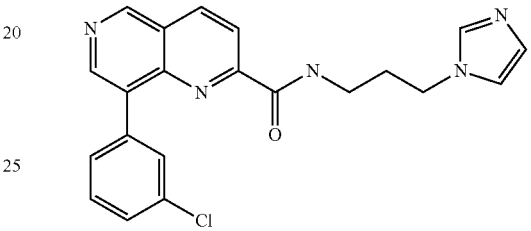

To a suspension of N-(3-(1H-imidazol-1-yl)propyl)-8-bromo-1,6-naphthyridine-2-carboxamide (0.08 g, 0.21 mmol) and 3-chlorophenylboronic acid (0.03 g, 0.21 mmol) and cesium carbonate (0.08 g, 0.23 mmol) in dioxane (7.5 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, methanol/dichloromethane=0:100 to 20:80) and trituration with diethyl ether/pentane yielded the title compound as brown solid (0.07 g, 77%). MS: m/e=392.4 [M+H]+.

EXAMPLE 37

N-(3-(1H-Imidazol-1-yl)propyl)-8-(4-chlorophenyl)-1,6-naphthyridine-2-carboxamide

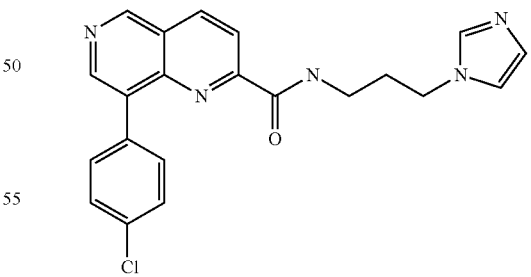

To a suspension of N-(3-(1H-imidazol-1-yl)propyl)-8-bromo-1,6-naphthyridine-2-carboxamide (0.08 g, 0.21 mmol) and 4-chlorophenylboronic acid (0.03 g, 0.21 mmol) and cesium carbonate (0.08 g, 0.23 mmol) in dioxane (7.5 ml) and water (1 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel,

EXAMPLE 38

N-(3-(1H-Imidazol-1-yl)propyl)-8-(3-methoxyphenyl)-1,6-naphthyridine-2-carboxamide

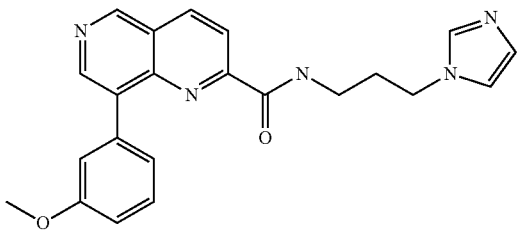 [SMILES: COc1cccc(-c2cncc3ccc(C(=O)NCCCn4ccnc4)nc23)c1]

To a suspension of N-(3-(1H-imidazol-1-yl)propyl)-8-bromo-1,6-naphthyridine-2-carboxamide (0.08 g, 0.22 mmol) and 3-methoxyphenylboronic acid (0.03 g, 0.22 mmol) and cesium carbonate (0.08 g, 0.24 mmol) in dioxane (14 ml) and water (1.4 ml) was added bis(diphenylphosphino)ferrocene-palladium(II)dichloride (0.01 g, 0.01 mmol). The mixture was stirred at 80° C. for 16 hours. Again cesium carbonate (0.08 g, 0.24 mmol) and bis(diphenylphosphino)ferrocene-palladium(II)dichloride (0.01 g, 0.01 mmol) were added and the mixture was stirred at 80° C. for 2 hours. Removal of the solvent by distillation and chromatography (silica gel, methanol/dichloromethane=2:98 to 5:95) and trituration with diethyl ether/pentane yielded the title compound as light red solid (0.05 g, 52%). MS: m/e=388.4 [M+H]$^+$.

EXAMPLE 39

N-(3-(1H-Imidazol-1-yl)propyl)-8-(2-methoxyphenyl)-1,6-naphthyridine-2-carboxamide

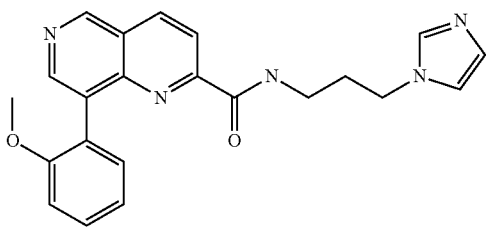 [SMILES: COc1ccccc1-c1cncc2ccc(C(=O)NCCCn3ccnc3)nc12]

To a suspension of N-(3-(1H-imidazol-1-yl)propyl)-8-bromo-1,6-naphthyridine-2-carboxamide (0.08 g, 0.22 mmol) and 2-methoxyphenylboronic acid (0.03 g, 0.22 mmol) and cesium carbonate (0.08 g, 0.24 mmol) in dioxane (14 ml) and water (1.4 ml) was added bis(diphenylphosphino)ferrocene-palladium(II)dichloride (0.01 g, 0.01 mmol). The mixture was stirred at 80° C. for 16 hours. Removal of the solvent by distillation and chromatography (silica gel, methanol/dichloromethane=2:98 to 5:95) and trituration with diethyl ether/pentane yielded the title compound as grey solid (0.02 g, 26%). MS: m/e=388.5 [M+H]$^+$.

methanol/dichloromethane=0:100 to 20:80) and trituration with diethyl ether/pentane yielded the title compound as brown solid (0.05 g, 52%). MS: m/e=392.4 [M+H]$^+$.

EXAMPLE 40

N-(3-(1H-Imidazol-1-yl)propyl)-8-(2-chlorophenyl)-1,6-naphthyridine-2-carboxamide

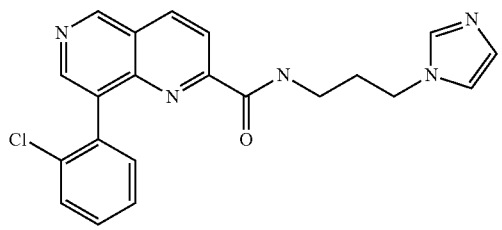 [SMILES: O=C(NCCCn1ccnc1)c1ccc2cncc(-c3ccccc3Cl)c2n1]

To a suspension of N-(3-(1H-imidazol-1-yl)propyl)-8-bromo-1,6-naphthyridine-2-carboxamide (0.13 g, 0.35 mmol) and 2-chlorophenylboronic acid (0.05 g, 0.35 mmol) and cesium carbonate (0.12 g, 0.38 mmol) in dioxane (12.5 ml) and water (1 ml) was added bis(diphenylphosphino)ferrocene-palladium(II)dichloride (0.01 g, 0.02 mmol). The mixture was stirred at 80° C. for 15 hours. Removal of the solvent by distillation and chromatography (silica gel, methanol/dichloromethane=0:100 to 30:70) and trituration with diethyl ether/pentane yielded the title compound as brown solid (0.09 g, 67%). MS: m/e=392.4 [M+H]$^+$.

EXAMPLE 41

N-(3-(1H-Imidazol-1-yl)propyl)-8-(pyridin-4-yl)-1,6-naphthyridine-2-carboxamide

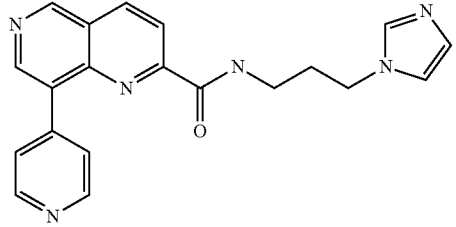 [SMILES: O=C(NCCCn1ccnc1)c1ccc2cncc(-c3ccncc3)c2n1]

To a suspension of N-(3-(1H-imidazol-1-yl)propyl)-8-bromo-1,6-naphthyridine-2-carboxamide (0.13 g, 0.35 mmol) and pyridin-4-ylboronic acid (0.04 g, 0.35 mmol) and cesium carbonate (0.12 g, 0.38 mmol) in dioxane (12.5 ml) and water (1 ml) was added bis(diphenylphosphino)ferrocene-palladium(II)dichloride (0.01 g, 0.02 mmol). The mixture was stirred at 80° C. for 15 hours. Removal of the solvent by distillation and chromatography (silica gel, methanol/dichloromethane=0:100 to 20:80) and trituration with diethyl ether/pentane yielded the title compound as brown solid (0.08 g, 60%). MS: m/e=359.4 [M+H]$^+$.

EXAMPLE 42

N-(3-(3,5-Dimethyl-1H-pyrazol-1-yl)propyl)-8-(4-methoxyphenyl)-1,6-naphthyridine-2-carboxamide

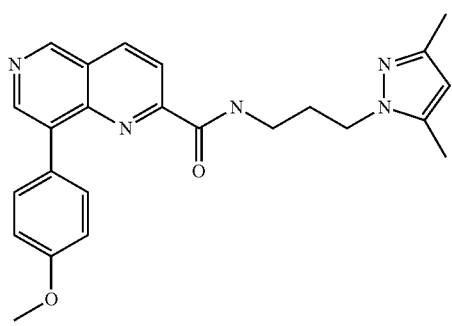 [SMILES: COc1ccc(-c2cncc3ccc(C(=O)NCCCn4nc(C)cc4C)nc23)cc1]

A mixture of 8-(4-methoxyphenyl)-1,6-naphthyridine-2-carboxylic acid (0.10 g, 0.29 mmol), N, N-diisopropylethylamine (0.05 g, 0.06 ml, 0.35 mmol) and O-(7-azabenzotriazol-1-yl)-N,N,N',N'-tetramethyluronium hexafluorophosphate (HATU, 0.13 g, 0.35 mmol) in dimethylformamide (5 ml) was stirred at room temperature for 10 minutes. 3-(3,5-Dimethyl-1H-pyrazol-1-yl)propan-1-amine (0.04 g, 0.29 mmol) was added and stirring was continued overnight. Removal of the solvent by distillation and chromatography (silica gel, ethyl acetate/heptane=50:50 to 100:0) yielded the title compound as yellow oil (0.02 g, 14%). MS: m/e=416.5 [M+H]$^+$.

EXAMPLE 43

N-(3-(1H-Imidazol-1-yl)propyl)-8-(3,6-dihydro-2H-pyran-4-yl)-1,6-naphthyridine-2-carboxamide

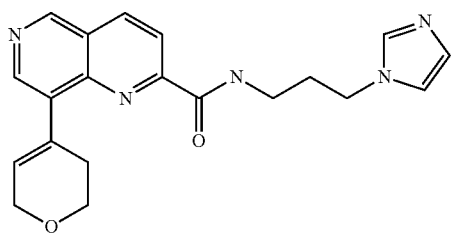 [SMILES: O=C(NCCCn1ccnc1)c1ccc2cncc(C3=CCOCC3)c2n1]

To a suspension of N-(3-(1H-imidazol-1-yl)propyl)-8-bromo-1,6-naphthyridine-2-carboxamide (0.20 g, 0.56 mmol) and 2-(3,6-dihydro-2H-pyran-4-yl)-4,4,5,5-tetramethyl-1,3,2-dioxaborolane (0.12 g, 0.56 mmol) and cesium carbonate (0.20 g, 0.61 mmol) in dioxane (14 ml) and water (1.4 ml) was added bis(diphenylphosphino)ferrocene-palladium(II)dichloride (0.02 g, 0.03 mmol). The mixture was stirred at 80° C. for 20 hours. Removal of the solvent by distillation and chromatography (silica gel, methanol/dichloromethane=2:98 to 5:95) yielded the title compound as brown solid (0.11 g, 56%). MS: m/e=364.4 [M+H]$^+$.

EXAMPLE 44

8-(4-Chlorophenyl)-1,6-naphthyridine-2-carboxamide

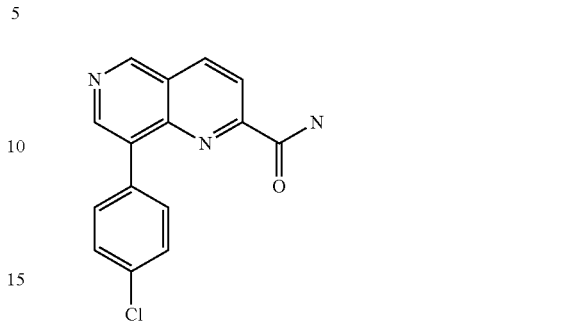

a)
8-(4-Chlorophenyl)-1,6-naphthyridine-2-carboxylic acid

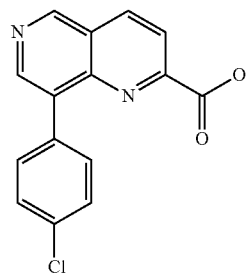 [SMILES: NC(=O)c1ccc2cncc(-c3ccc(Cl)cc3)c2n1]

To a suspension of 8-bromo-1,6-naphthyridine-2-carboxylic acid (1.20 g, 4.74 mmol) and 4-chlorophenylboronic acid (0.74 g, 4.74 mmol) and cesium carbonate (1.70 g, 5.22 mmol) in dioxane (40 ml) and water (10 ml) was added bis(diphenylphosphino)ferrocene-palladium(II)dichloride (0.17 g, 0.24 mmol). The mixture was stirred at 80° C. for 4 hours. Removal of the solvent by distillation and extraction with water (acidified with 0.1 N aqueous hydrochloric acid to pH=3-4)/ethyl acetate yielded the title compound as light brown solid (1.27 g, 94%). MS: m/e=283.2 [M−H]$^+$.

b)
8-(4-Chlorophenyl)-1,6-naphthyridine-2-carboxamide

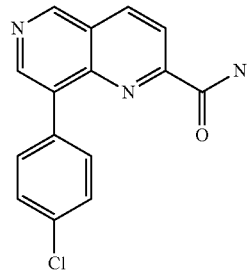

A mixture of 8-(4-chlorophenyl)-1,6-naphthyridine-2-carboxylic acid (0.60 g, 2.11 mmol), 1,1'-carbonyldiimidazole (0.38 g, 2.32 mmol) in dichloromethane (15 ml) was stirred at room temperature for 30 minutes. Aqueous ammonium hydroxide (1.0 ml, 25.7 mmol) was added and stirring was continued for 7 days. Extraction with water/ethyl acetate and chromatography (silica gel, ethyl acetate/heptane=50:50 to 100:0) and trituration with diethyl ether/pentane yielded the title compound as light brown solid (0.24 g, 40%). MS: m/e=284.3 [M+H]+.

EXAMPLE 45

8-(4-Chlorophenyl)-N-(pyridin-3-ylmethyl)-1,6-naphthyridine-2-carboxamide

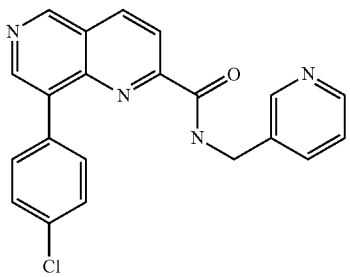 [SMILES: O=C(NCc1cccnc1)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Pyridin-3-ylmethanamine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.001 g, 1%). MS: m/e=375.3 [M+H]+.

EXAMPLE 46

8-(4-Chlorophenyl)-N-(pyridin-2-ylmethyl)-1,6-naphthyridine-2-carboxamide

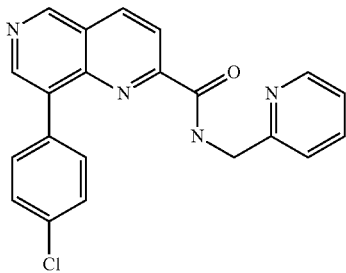

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Pyridin-2-ylmethanamine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.008 g, 7%). MS: m/e=375.3 [M+H]+.

EXAMPLE 47

8-(4-Chlorophenyl)-N-(2-methoxybenzyl)-1,6-naphthyridine-2-carboxamide

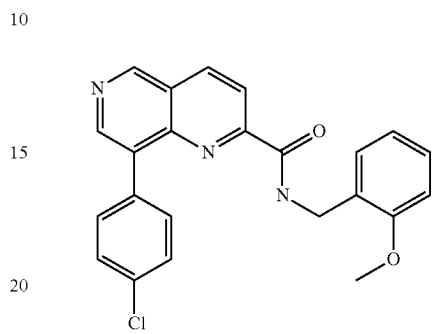

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. (2-Methoxyphenyl)methanamine (0.04 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.005 g, 5%). MS: m/e=404.3 [M+H]+.

EXAMPLE 48

8-(4-Chlorophenyl)-N-((5-methylpyrazin-2-yl)methyl)-1,6-naphthyridine-2-carboxamide

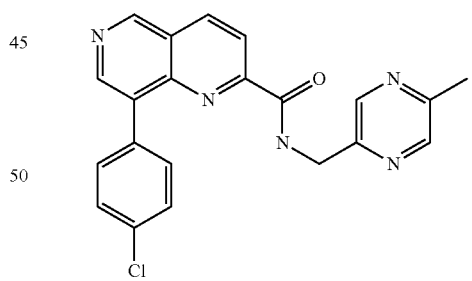

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. (5-Methylpyrazin-2-yl)methanamine (0.04 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.004 g, 4%). MS: m/e=390.4 [M+H]+.

EXAMPLE 49

N'-(8-(4-Chlorophenyl)-1,6-naphthyridine-2-carbonyl)methanesulfonohydrazide

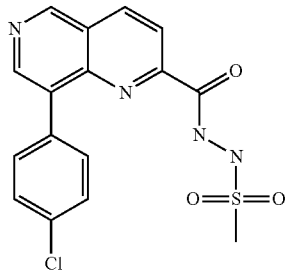 [SMILES: CS(=O)(=O)NNC(=O)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Methanesulfonohydrazide (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.001 g, 1%). MS: m/e=377.3 [M+H]$^+$.

EXAMPLE 50

8-(4-Chlorophenyl)-N-(4-(methylsulfonyl)benzyl)-1,6-naphthyridine-2-carboxamide

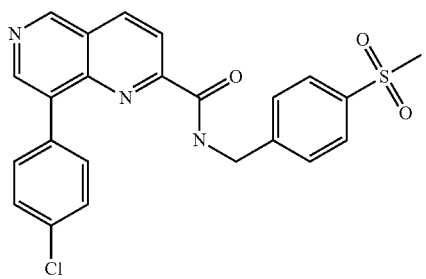 [SMILES: CS(=O)(=O)c1ccc(CNC(=O)c2ccc3cncc(-c4ccc(Cl)cc4)c3n2)cc1]

A mixture of 8-(4-chlorophenyl)-1,6-naphthyridine-2-carboxylic acid (0.30 g, 1.05 mmol), N,N-diisopropylethylamine (0.17 g, 0.23 ml, 1.29 mmol) and O-(7-azabenzotriazol-1-yl)-N,N,N',N'-tetramethyluronium hexafluorophosphate (HATU, 0.49 g, 1.29 mmol) in dimethylformamide (10 ml) was stirred at room temperature for 2 minutes. (4-(Methylsulfonyl)phenyl)methanamine (0.20 g, 1.05 mmol) was added and stirring was continued for 5 days. Removal of the solvent by distillation and chromatography (silica gel, ethyl acetate/heptane=50:50 to 100:0, and C18 reverse phase, methanol/water (0.1% formic acid)=20:80 to 95:5) yielded the title compound as a light yellow solid (0.03 g, 6%). MS: m/e=452.4 [M+H]$^+$.

EXAMPLE 51

8-(4-Chlorophenyl)-N-(3-(methylsulfonyl)benzyl)-1,6-naphthyridine-2-carboxamide

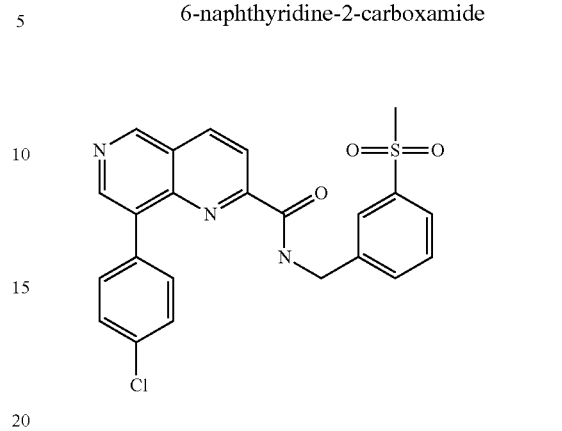

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. (3-(Methylsulfonyl)phenyl)methanamine (0.06 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.001 g, 1%). MS: m/e=452.3 [M+H]$^+$.

EXAMPLE 52

(−)-8-(4-Chlorophenyl)-N-(1-(3-(methylsulfonyl)phenyl)ethyl)-1,6-naphthyridine-2-carboxamide a) 8-Bromo-N-(1-(3-(methylsulfonyl)phenyl)ethyl)-1,6-naphthyridine-2-carboxamide

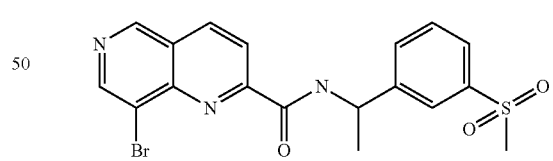

A mixture of 8-bromo-1,6-naphthyridine-2-carboxylic acid (0.20 g, 0.79 mmol), N,N-diisopropylethylamine (0.23 g, 0.31 ml, 1.75 mmol) and O-(7-azabenzotriazol-1-yl)-N,N,N',N'-tetramethyluronium hexafluorophosphate (HATU, 0.37 g, 0.96 mmol) in dimethylformamide (6 ml) was stirred at room temperature for 1 hour. 1-(3-(Methylsulfonyl)phenyl)ethanamine hydrochloride (0.18 g, 0.79 mmol) was added and stirring was continued overnight. Extraction with water/ethyl acetate and chromatography (silica gel, ethyl acetate/heptane=50:50 to 100:0) yielded the title compound as light brown solid (0.22 g, 63%). MS: m/e=434.4, 436.3 [M+H]$^+$.

b) 8-(4-Chlorophenyl)-N-(1-(3-(methylsulfonyl)phenyl)ethyl)-1,6-naphthyridine-2-carboxamide

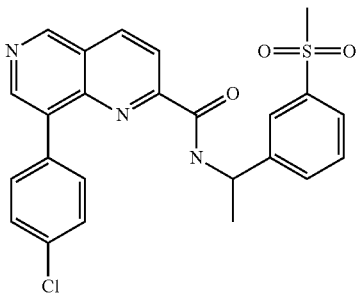 [SMILES: CC(NC(=O)c1ccc2cncc(-c3ccc(Cl)cc3)c2n1)c1cccc(S(C)(=O)=O)c1]

To a suspension of 8-bromo-N-(1-(3-(methylsulfonyl)phenyl)ethyl)-1,6-naphthyridine-2-carboxamide (0.20 g, 0.46 mmol) and 4-chlorophenylboronic acid (0.07 g, 0.46 mmol) and cesium carbonate (0.17 g, 0.51 mmol) in dioxane (25 ml) and water (2.5 ml) was added bis(diphenylphosphino)ferrocene-palladium(II)dichloride (0.02 g, 0.02 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as yellow solid (0.14 g, 72%). MS: m/e=466.3 [M+H]+.

c) (−)-8-(4-Chloro-phenyl)-[1,6]naphthyridine-2-carboxylic acid [(S or R)-1-(3-methanesulfonyl-phenyl)-ethyl]-amide

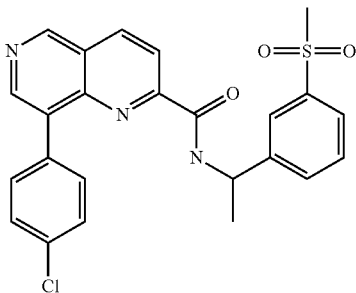 [SMILES: CC(NC(=O)c1ccc2cncc(-c3ccc(Cl)cc3)c2n1)c1cccc(S(C)(=O)=O)c1]

Rac-8-(4-Chlorophenyl)-N-(1-(3-(methylsulfonyl)phenyl)ethyl)-1,6-naphthyridine-2-carboxamide (0.48 g) was separated by chromatography (Chiralpak AD, ethanol/heptane=40:60) to yield the title compound as brown solid (0.17 g, 35%), MS: m/e=466.4 [M+H]+, and the (+)-[R or S]-8-(4-Chlorophenyl)-N-(1-(3-(methylsulfonyl)phenyl)ethyl)-1,6-naphthyridine-2-carboxamide enantiomer was isolated as light yellow solid (0.18 g, 38%), MS: m/e=466.4 [M+H]+.

EXAMPLE 53

8-(4-Chlorophenyl)-N-phenyl-1,6-naphthyridine-2-carboxamide

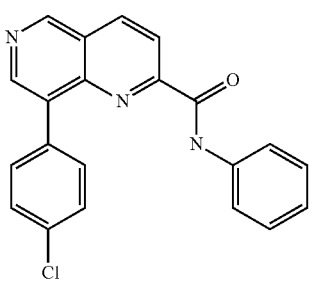 [SMILES: O=C(Nc1ccccc1)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Aniline (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.001 g, 1%). MS: m/e=360.3 [M+H]+.

EXAMPLE 54

8-(4-Chlorophenyl)-N-(pyridin-3-yl)-1,6-naphthyridine-2-carboxamide

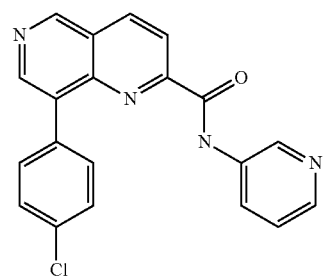 [SMILES: O=C(Nc1cccnc1)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Pyridin-3-amine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.006 g, 6%). MS: m/e=361.2 [M+H]+.

EXAMPLE 55

8-(4-Chlorophenyl)-N-(1-methyl-1H-pyrazol-4-yl)-1,6-naphthyridine-2-carboxamide

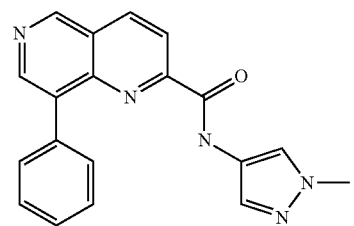

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. 1-Methyl-1H- pyrazol-4-amine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.01 g, 10%). MS: m/e=364.4 [M+H]+.

EXAMPLE 56

(8-(4-Chlorophenyl)-1,6-naphthyridin-2-yl)(piperidin-1-yl)methanone

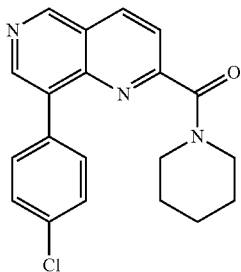

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Piperidine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.007 g, 7%). MS: m/e=352.4 [M+H]+.

EXAMPLE 57

(8-(4-Chlorophenyl)-1,6-naphthyridin-2-yl)(morpholino)methanone

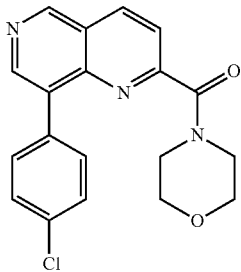 [SMILES: O=C(c1ccc2cncc(-c3ccc(Cl)cc3)c2n1)N1CCOCC1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Morpholine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.001 g, 1%). MS: m/e=354.4 [M+H]+.

EXAMPLE 58 tert-Butyl 4-(8-(4-chlorophenyl)-1,6-naphthyridine-2-carbonyl)piperazine-1-carboxylate

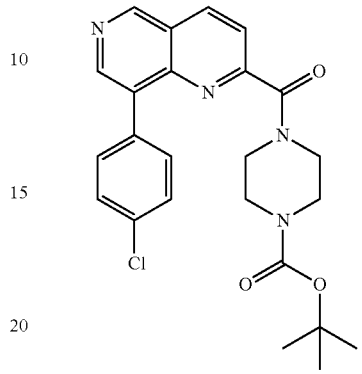

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. tert-Butyl piperazine-1-carboxylate (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.003 g, 3%). MS: m/e=453.5 [M+H]+.

EXAMPLE 59

8-(4-Chlorophenyl)-N-(piperidin-1-yl)-1,6-naphthyridine-2-carboxamide

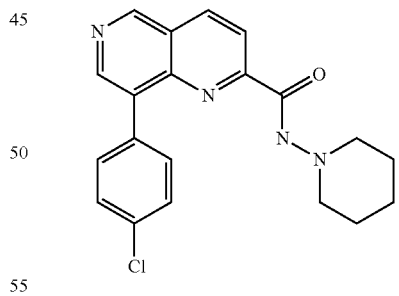

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Piperidin-1-amine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.002 g, 2%). MS: m/e=367.4 [M+H]+.

EXAMPLE 60

8-(4-Chlorophenyl)-N-(tetrahydrofuran-3-yl)-1,6-naphthyridine-2-carboxamide

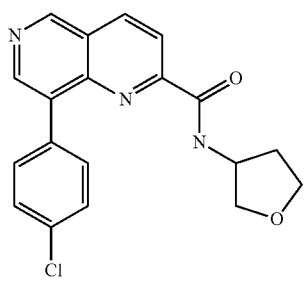

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Tetrahydrofuran-3-amine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.002 g, 2%). MS: m/e=354.4 [M+H]$^+$.

EXAMPLE 61

(8-(4-Chlorophenyl)-1,6-naphthyridin-2-yl)(piperazin-1-yl)methanone

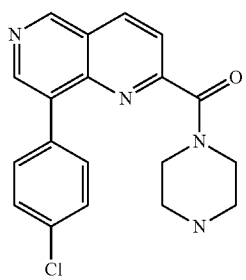

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Piperazine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.006 g, 6%). MS: m/e=354.4 [M+H]$^+$.

EXAMPLE 62

8-(4-Chlorophenyl)-N-((2-methyl-5-oxopyrrolidin-2-yl)methyl)-1,6-naphthyridine-2-carboxamide a) 8-Bromo-N-((2-methyl-5-oxopyrrolidin-2-yl)methyl)-1,6-naphthyridine-2-carboxamide

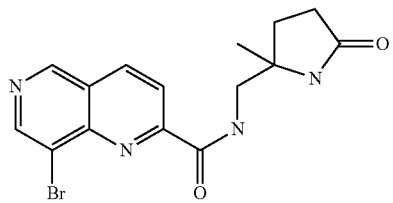 [SMILES: CC1(CNC(=O)c2ccc3cncc(Br)c3n2)CCC(=O)N1]

8-Bromo-1,6-naphthyridine-2-carboxylic acid (0.20 g, 0.79 mmol) was combined with dichloromethane (10 ml) and 3 drops dimethylformamide. The light brown suspension was cooled in an ice bath and oxalyl chloride (0.89 g, 0.62 ml, 7.03 mmol) was added. The mixture was stirred for 30 minutes at 0° C. and for 30 minutes at room temperature. All volatiles were distilled off. The residue was taken up in dichloromethane (10 ml) and was added to a mixture of 5-(aminomethyl)-5-methylpyrrolidin-2-one hydrochloride (0.12 g, 0.70 mmol) and triethylamine (0.15 g, 0.21 mml, 1.48 mmol) in dichloromethane at 0° C. The mixture was stirred for 45 minutes at 0° C. and then at room temperature overnight. Extraction with water/dichloromethane and chromatography (silica gel, methanol/dichloromethane=0:100 to 20:80 and trituration with dichloromethane (5 mL) yielded the title compound as off-white solid (0.11 g, 33%). MS: m/e=363.4, 365.4 [M+H]$^+$.

b) 8-(4-Chlorophenyl)-N-((2-methyl-5-oxopyrrolidin-2-yl)methyl)-1,6-naphthyridine-2-carboxamide

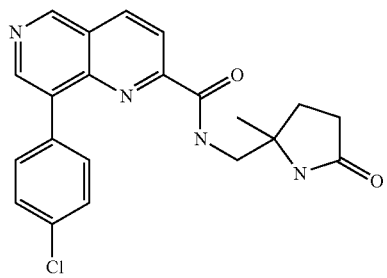 [SMILES: CC1(CNC(=O)c2ccc3cncc(-c4ccc(Cl)cc4)c3n2)CCC(=O)N1]

To a suspension of 8-bromo-N-((2-methyl-5-oxopyrrolidin-2-yl)methyl)-1,6-naphthyridine-2-carboxamide (0.10 g, 0.27 mmol) and 4-chlorophenylboronic acid (0.04 g, 0.28 mmol) and cesium carbonate (0.10 g, 0.30 mmol) in dioxane (12 ml) and water (1.2 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, dichloromethane/methanol=100:0 to 20:80) and trituration with diethyl ether yielded the title compound as light brown solid (0.10 g, 91%). MS: m/e=395.5 [M+H]$^+$.

EXAMPLE 63

8-(4-Chlorophenyl)-N-(2,2,2-trifluoroethyl)-1,6-naphthyridine-2-carboxamide

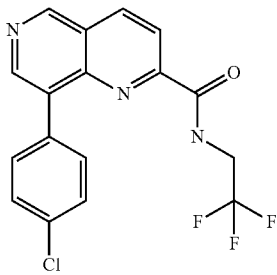 [SMILES: O=C(NCC(F)(F)F)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. 2,2,2-Trifluoroethanamine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.006 g, 6%). MS: m/e=366.4 [M+H]+.

EXAMPLE 64

8-(4-Chlorophenyl)-N-(3,3,3-trifluoropropyl)-1,6-naphthyridine-2-carboxamide

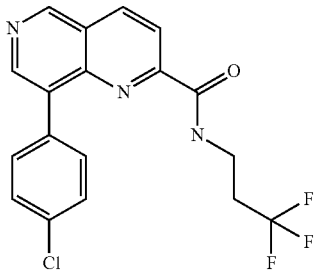 [SMILES: O=C(NCCC(F)(F)F)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. 3,3,3-Trifluoropropan-1-amine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.004 g, 4%). MS: m/e=380.4 [M+H]+.

EXAMPLE 65

8-(4-Chlorophenyl)-N-cyclopropyl-1,6-naphthyridine-2-carboxamide

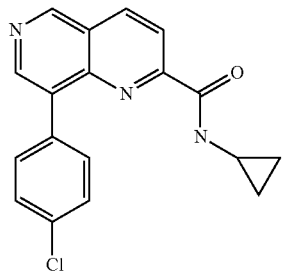 [SMILES: O=C(NC1CC1)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Cyclopropanamine (0.02 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.009 g, 10%). MS: m/e=324.4 [M+H]+.

EXAMPLE 66

8-(4-Chlorophenyl)-N-(cyclopropylmethyl)-N-methyl-1,6-naphthyridine-2-carboxamide

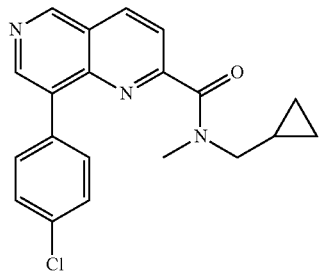

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Cyclopropylmethyl-methyl-amine (0.02 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.007 g, 7%). MS: m/e=352.5 [M+H]+.

EXAMPLE 67

8-(4-Chlorophenyl)-N-(cyclopropylmethyl)-1,6-naphthyridine-2-carboxamide

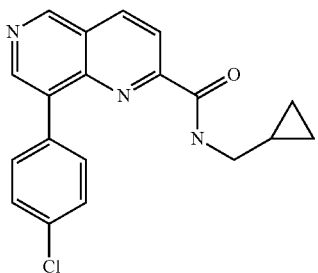 [SMILES: O=C(NCC1CC1)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Cyclopropylmethanamine (0.02 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.002 g, 2%). MS: m/e=338.4 [M+H]$^+$.

EXAMPLE 68

8-(4-Chlorophenyl)-N-neopentyl-1,6-naphthyridine-2-carboxamide

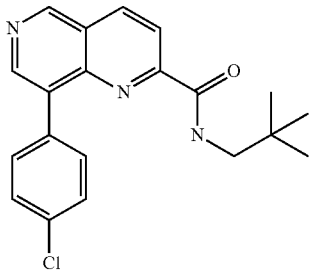 [SMILES: CC(C)(C)CNC(=O)c1ccc2cncc(-c3ccc(Cl)cc3)c2n1]

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. 2,2-Dimethylpropan-1-amine (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.01 g, 12%). MS: m/e=354.4 [M+H]$^+$.

EXAMPLE 69

N-tert-Butyl-8-(4-chlorophenyl)-1,6-naphthyridine-2-carboxamide

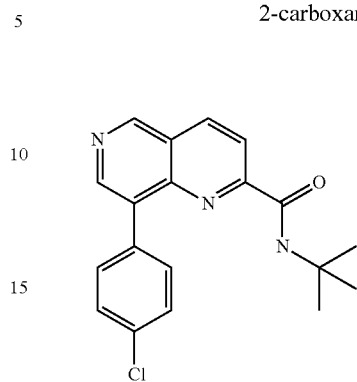

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. 2-Methylpropan-2-amine (0.02 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.009 g, 9%). MS: m/e=340.4 [M+H]$^+$.

EXAMPLE 70

8-(4-Chlorophenyl)-N-isopropyl-1,6-naphthyridine-2-carboxamide

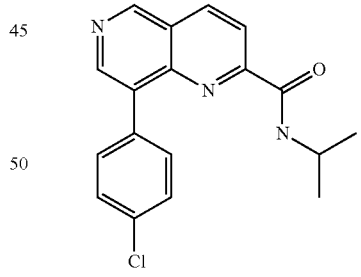

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. Propan-2-amine (0.02 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.005 g, 6%). MS: m/e=326.3 [M+H]$^+$.

EXAMPLE 71

8-(4-Chlorophenyl)-N-(1-hydroxy-2-methylpropan-2-yl)-1,6-naphthyridine-2-carboxamide

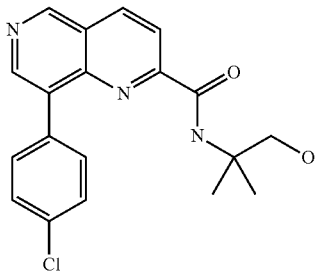

A mixture of 8-(4-chlorophenyl)-1,6-naphthyridine-2-carboxylic acid (0.08 g, 0.28 mmol), N,N-diisopropylethylamine (0.04 g, 0.06 ml, 0.34 mmol) and O-(7-azabenzotriazol-1-yl)-N,N,N',N'-tetramethyluronium hexafluorophosphate (HATU, 0.13 g, 0.35 mmol) in dimethylformamide (1 ml) was stirred at room temperature for 1 hour. 2-Amino-2-methylpropan-1-ol (0.03 g, 0.31 mmol) was added and stirring was continued for 5 hours. Removal of the solvent by distillation and chromatography (C18 reverse phase, methanol/water (0.1% formic acid)=20:80 to 95:5) yielded the title compound as a solid (0.007 g, 7%). MS: m/e=356.4 [M+H]+.

EXAMPLE 72

8-(4-Chlorophenyl)-N-(2-(methylsulfonyl)ethyl)-1,6-naphthyridine-2-carboxamide

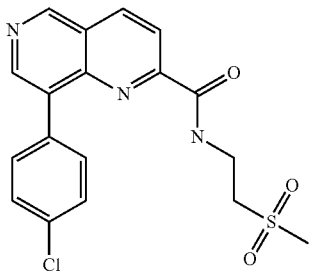 [SMILES: CS(=O)(=O)CCNC(=O)c1ccc2cncc(-c3ccc(Cl)cc3)c2n1]

A mixture of 8-(4-chlorophenyl)-1,6-naphthyridine-2-carboxylic acid (0.30 g, 1.05 mmol), N,N-diisopropylethylamine (0.17 g, 0.23 ml, 1.29 mmol) and O-(7-azabenzotriazol-1-yl)-N,N,N',N'-tetramethyluronium hexafluorophosphate (HATU, 0.49 g, 1.29 mmol) in dimethylformamide (10 ml) was stirred at room temperature for 2 minutes. 2-(Methylsulfonyl)ethanamine (0.13 g, 1.05 mmol) was added and stirring was continued for 5 days. Removal of the solvent by distillation and chromatography (silica gel, ethyl acetate/heptane=50:50 to 100:0 and C18 reverse phase, methanol/water (0.1% formic acid)=20:80 to 95:5) yielded the title compound as a light brown solid (0.03 g, 7%). MS: m/e=390.4 [M+H]+.

EXAMPLE 73

(8-(4-Chlorophenyl)-1,6-naphthyridin-2-yl)(4-methylpiperazin-1-yl)methanone

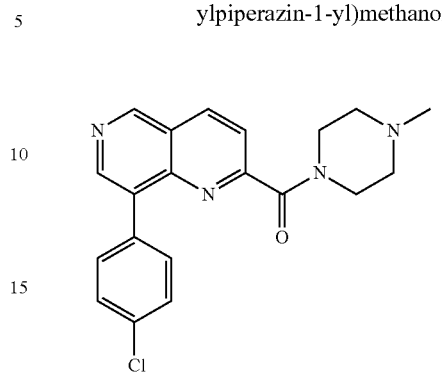

A mixture of 8-(4-chlorophenyl)-1,6-naphthyridine-2-carboxylic acid (0.20 g, 0.07 mmol), N,N-diisopropylethylamine (0.11 g, 0.15 ml, 0.86 mmol) and O-(7-azabenzotriazol-1-yl)-N,N,N',N'-tetramethyluronium hexafluorophosphate (HATU, 0.33 g, 0.86 mmol) in dimethylformamide (4 ml) was stirred at room temperature for 1 hour. 1-Methylpiperazine (0.07 g, 0.70 mmol) was added and stirring was continued overnight. Removal of the solvent by distillation and chromatography (silica gel, ethyl acetate/heptane=50:50 to 100:0) and trituration with diethyl ether/pentane yielded the title compound as brown solid (0.13 g, 52%). MS: m/e=367.5 [M+H]+.

EXAMPLE 74

[8-(4-Chloro-phenyl)-[1,6]naphthyridin-2-yl]-(1,1-dioxo-thiomorpholin-4-yl)-methanone

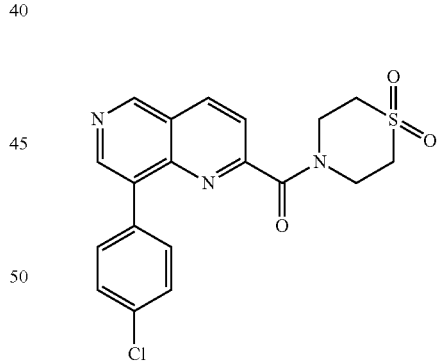

A mixture of 8-(4-chlorophenyl)-1,6-naphthyridine-2-carboxylic acid (0.20 g, 0.70 mmol), N,N-diisopropylethylamine (0.11 g, 0.15 ml, 0.86 mmol) and O-(7-azabenzotriazol-1-yl)-N,N,N',N'-tetramethyluronium hexafluorophosphate (HATU, 0.33 g, 0.86 mmol) in dimethylformamide (4 ml) was stirred at room temperature for 1 hour. Thiomorpholine 1,1-dioxide (0.10 g, 0.77 mmol) was added and stirring was continued for 2 hours. Extraction with water/ethyl acetate and chromatography (silica gel, ethyl acetate/heptane=50:50 to 100:0, and C18 reverse phase, methanol/water (0.1% formic acid)=20:80 to 95:5) yielded the title compound as off-white solid (0.12 g, 41%). MS: m/e=402.3 [M+H]+.

EXAMPLE 75

(8-(4-Chlorophenyl)-1,6-naphthyridin-2-yl)(3-hydroxypyrrolidin-1-yl)methanone

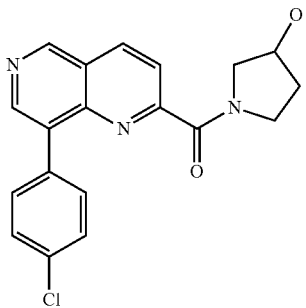 [SMILES: O=C(c1ccc2cncc(-c3ccc(Cl)cc3)c2n1)N1CCC(O)C1]

A mixture of 8-(4-chlorophenyl)-1,6-naphthyridine-2-carboxylic acid (0.20 g, 0.70 mmol), N,N-diisopropylethylamine (0.11 g, 0.15 ml, 0.86 mmol) and O-(7-azabenzotriazol-1-yl)-N,N,N',N'-tetramethyluronium hexafluorophosphate (HATU, 0.33 g, 0.86 mmol) in dimethylformamide (4 ml) was stirred at room temperature for 1 hour. Pyrrolidin-3-ol (0.06 g, 0.70 mmol) was added and stirring was continued overnight. Extraction with water/ethyl acetate and chromatography (silica gel, ethyl acetate/heptane=50:50 to 100:0) yielded the title compound as brown solid (0.17 g, 70%). MS: m/e=354.3 [M+H]$^+$.

EXAMPLE 76

8-(4-Chlorophenyl)-N-(1-cyanocyclopropyl)-1,6-naphthyridine-2-carboxamide

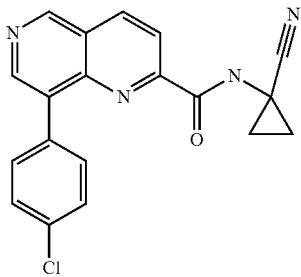 [SMILES: N#CC1(NC(=O)c2ccc3cncc(-c4ccc(Cl)cc4)c3n2)CC1]

A mixture of 8-(4-chlorophenyl)-1,6-naphthyridine-2-carboxylic acid (0.20 g, 0.70 mmol), N,N-diisopropylethylamine (0.11 g, 0.15 ml, 0.86 mmol) and O-(7-azabenzotriazol-1-yl)-N,N,N',N'-tetramethyluronium hexafluorophosphate (HATU, 0.33 g, 0.86 mmol) in dimethylformamide (4 ml) was stirred at room temperature for 1 hour. 1-Aminocyclopropanecarbonitrile (0.06 g, 0.70 mmol) was added and stirring was continued during the weekend. Extraction with water/ethyl acetate and chromatography (silica gel, ethyl acetate/heptane=50:50 to 100:0, and C18 reverse phase, methanol/water (0.1% formic acid)=20:80 to 95:5) yielded the title compound as light yellow solid (0.07 g, 30%). MS: m/e=349.3 [M+H]$^+$.

EXAMPLE 77

8-(4-Fluorophenyl)-1,6-naphthyridine-2-carboxamide

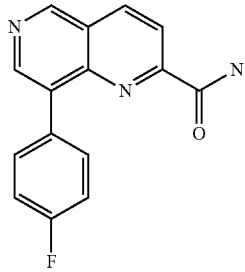 [SMILES: NC(=O)c1ccc2cncc(-c3ccc(F)cc3)c2n1]

To a suspension of 8-bromo-1,6-naphthyridine-2-carboxamide (CAS 875514-62-8, 0.08 g, 0.32 mmol) and 4-fluorophenylboronic acid (0.04 g, 0.32 mmol) and cesium carbonate (0.11 g, 0.35 mmol) in dioxane (5 ml) and water (0.5 ml) was added bis(diphenylphosphino)ferrocene-palladium (II)dichloride (0.01 g, 0.02 mmol). The mixture was stirred at 80° C. for 20 hours. Removal of the solvent by distillation and chromatography (silica gel, ethyl acetate/heptane=50:50 to 100:0) yielded the title compound as off-white solid (0.06 g, 76%). MS: m/e=268.4 [M+H]$^+$.

EXAMPLE 78

8-(3-Fluorophenyl)-1,6-naphthyridine-2-carboxamide

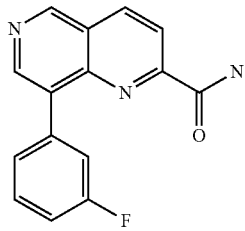 [SMILES: NC(=O)c1ccc2cncc(-c3cccc(F)c3)c2n1]

To a suspension of 8-bromo-1,6-naphthyridine-2-carboxamide (0.08 g, 0.32 mmol) and 3-fluorophenylboronic acid (0.04 g, 0.32 mmol) and cesium carbonate (0.11 g, 0.35 mmol) in dioxane (5 ml) and water (0.5 ml) was added bis(diphenylphosphino)ferrocene-palladium(II)dichloride (0.01 g, 0.02 mmol). The mixture was stirred at 80° C. for 20 hours. Removal of the solvent by distillation and chromatography (silica gel, ethyl acetate/heptane=50:50 to 100:0) and trituration with diethyl ether yielded the title compound as light brown solid (0.08 g, 94%). MS: m/e=268.4 [M+H]$^+$.

EXAMPLE 79

8-(2-Fluorophenyl)-1,6-naphthyridine-2-carboxamide

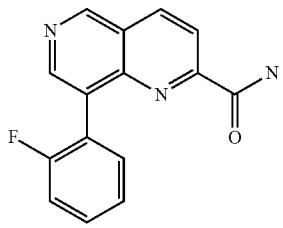 [SMILES: NC(=O)c1ccc2cncc(-c3ccccc3F)c2n1]

To a suspension of 8-bromo-1,6-naphthyridine-2-carboxamide (0.06 g, 0.24 mmol) and 2-fluorophenylboronic acid (0.03 g, 0.24 mmol) and cesium carbonate (0.09 g, 0.26 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.05 g, 83%). MS: m/e=268.4 [M+H]$^+$.

EXAMPLE 80

8-Tolyl-1,6-naphthyridine-2-carboxamide

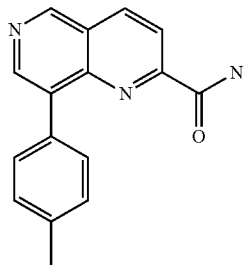 [SMILES: Cc1ccc(-c2cncc3ccc(C(N)=O)nc23)cc1]

To a suspension of 8-bromo-1,6-naphthyridine-2-carboxamide (0.06 g, 0.24 mmol) and p-tolylboronic acid (0.03 g, 0.24 mmol) and cesium carbonate (0.09 g, 0.26 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.04 g, 62%). MS: m/e=264.4 [M+H]$^+$.

EXAMPLE 81

8-m-Tolyl-1,6-naphthyridine-2-carboxamide

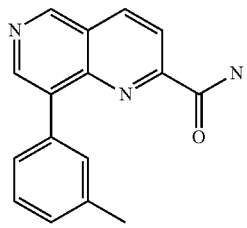 [SMILES: Cc1cccc(-c2cncc3ccc(C(N)=O)nc23)c1]

To a suspension of 8-bromo-1,6-naphthyridine-2-carboxamide (0.04 g, 0.16 mmol) and m-tolylboronic acid (0.02 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.04 g, 84%). MS: m/e=264.4 [M+H]$^+$.

EXAMPLE 82

8-o-Tolyl-1,6-naphthyridine-2-carboxamide

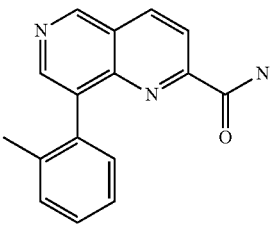 [SMILES: Cc1ccccc1-c1cncc2ccc(C(N)=O)nc12]

To a suspension of 8-bromo-1,6-naphthyridine-2-carboxamide (0.04 g, 0.16 mmol) and o-tolylboronic acid (0.02 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.04 g, 84%). MS: m/e=264.4 [M+H]$^+$.

EXAMPLE 83

8-(3,4-Difluorophenyl)-1,6-naphthyridine-2-carboxamide

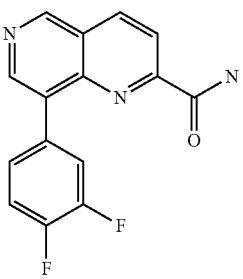 [SMILES: NC(=O)c1ccc2cncc(-c3ccc(F)c(F)c3)c2n1]

To a suspension of 8-bromo-1,6-naphthyridine-2-carboxamide (0.04 g, 0.16 mmol) and 3,4-difluorophenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (0.04 g, 88%). MS: m/e=286.3 [M+H]$^+$.

EXAMPLE 84

8-(3,4,5-Trifluorophenyl)-1,6-naphthyridine-2-carboxamide

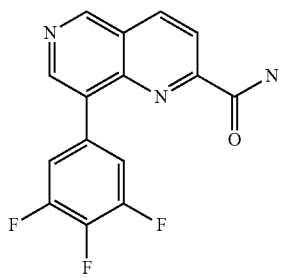 [SMILES: NC(=O)c1ccc2cncc(-c3cc(F)c(F)c(F)c3)c2n1]

To a suspension of 8-bromo-1,6-naphthyridine-2-carboxamide (0.04 g, 0.16 mmol) and 3,4,5-trifluorophenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.04 g, 85%). MS: m/e=304.3 [M+H]$^+$.

EXAMPLE 85

8-(4-Cyanophenyl)-1,6-naphthyridine-2-carboxamide

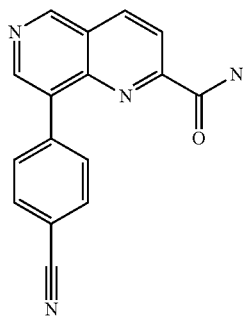 [SMILES: N#Cc1ccc(-c2cncc3ccc(C(N)=O)nc23)cc1]

To a suspension of 8-bromo-1,6-naphthyridine-2-carboxamide (0.04 g, 0.16 mmol) and 4-cyanophenylboronic acid (0.02 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.04 g, 97%). MS: m/e=275.5 [M+H]$^+$.

EXAMPLE 86

8-(4-(Methylsulfonyl)phenyl)-1,6-naphthyridine-2-carboxamide

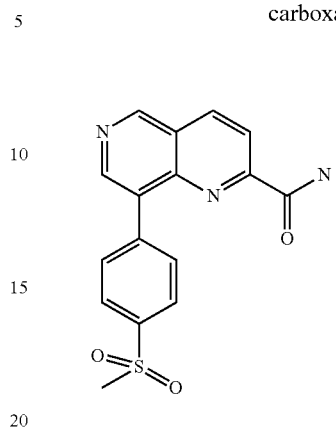

To a suspension of 8-bromo-1,6-naphthyridine-2-carboxamide (0.04 g, 0.16 mmol) and 4-(methylsulfonyl)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (0.04 g, 85%). MS: m/e=328.4 [M+H]$^+$.

EXAMPLE 87

8-(3-(Methylsulfonyl)phenyl)-1,6-naphthyridine-2-carboxamide

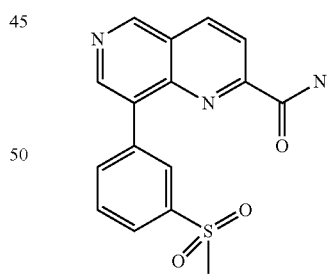

To a suspension of 8-bromo-1,6-naphthyridine-2-carboxamide (0.04 g, 0.16 mmol) and 3-(methylsulfonyl)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.02 g, 46%). MS: m/e=328.4 [M+H]$^+$.

EXAMPLE 88

8-(2-(Methylsulfonyl)phenyl)-1,6-naphthyridine-2-carboxamide

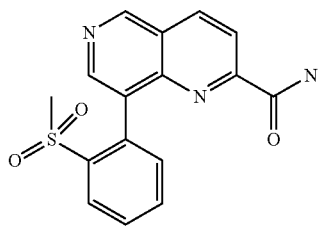 [SMILES: CS(=O)(=O)c1ccccc1-c1cncc2ccc(C(N)=O)nc12]

To a suspension of 8-bromo-1,6-naphthyridine-2-carboxamide (0.04 g, 0.16 mmol) and 2-(methylsulfonyl)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as brown solid (0.04 g, 79%). MS: m/e=328.4 [M+H]$^+$.

EXAMPLE 89

8-(6-Methoxypyridin-3-yl)-1,6-naphthyridine-2-carboxamide

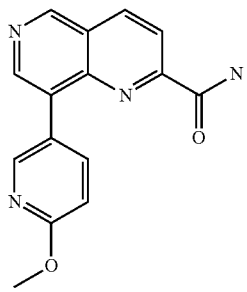

To a suspension of 8-bromo-1,6-naphthyridine-2-carboxamide (0.04 g, 0.16 mmol) and 6-methoxypyridin-3-ylboronic acid (0.02 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light yellow solid (0.03 g, 76%). MS: m/e=281.4 [M+H]$^+$.

EXAMPLE 90

8-(2-Methylpyridin-4-yl)-1,6-naphthyridine-2-carboxamide

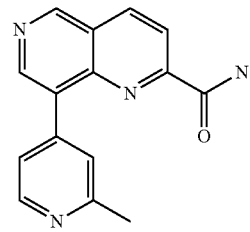

To a suspension of 8-bromo-1,6-naphthyridine-2-carboxamide (0.04 g, 0.16 mmol) and 2-methylpyridin-4-ylboronic acid (0.02 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, methanol/dichloromethane=0:100 to 20:80) and trituration with diethyl ether yielded the title compound as brown solid (0.04 g, 93%). MS: m/e=265.4 [M+H]$^+$.

EXAMPLE 91

8-(Benzo[d][1,3]dioxol-5-yl)-1,6-naphthyridine-2-carboxamide

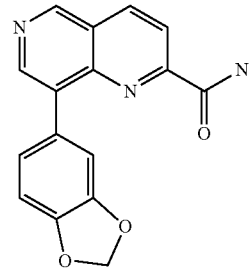 [SMILES: NC(=O)c1ccc2cncc(-c3ccc4c(c3)OCO4)c2n1]

To a suspension of 8-bromo-1,6-naphthyridine-2-carboxamide (0.04 g, 0.16 mmol) and benzo[d][1,3]dioxol-5-ylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light yellow solid (0.03 g, 69%). MS: m/e=294.4 [M+H]$^+$.

EXAMPLE 92

8-(2,3-Dihydrobenzo[b][1,4]dioxin-6-yl)-1,6-naphthyridine-2-carboxamide

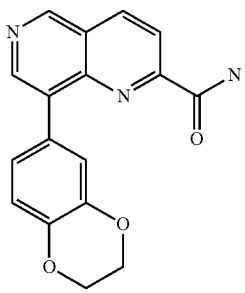 [SMILES: NC(=O)c1ccc2cncc(-c3ccc4c(c3)OCCO4)c2n1]

To a suspension of 8-bromo-1,6-naphthyridine-2-carboxamide (0.04 g, 0.16 mmol) and 2,3-dihydrobenzo[b][1,4]dioxin-6-ylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as brown solid (0.04 g, 82%). MS: m/e=308.4 [M+H]$^+$.

EXAMPLE 93

8-(3-Morpholinophenyl)-1,6-naphthyridine-2-carboxamide

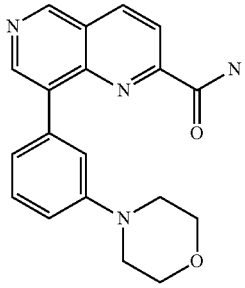

To a suspension of 8-bromo-1,6-naphthyridine-2-carboxamide (0.04 g, 0.16 mmol) and 3-morpholinophenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as yellow solid (0.04 g, 72%). MS: m/e=335.4 [M+H]$^+$.

EXAMPLE 94

8-(4-Morpholinophenyl)-1,6-naphthyridine-2-carboxamide

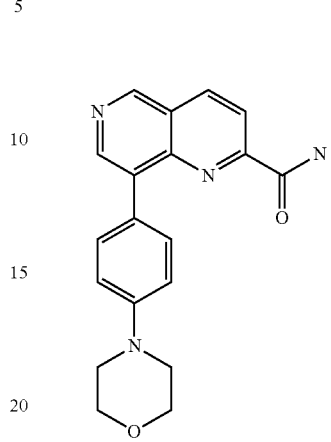

To a suspension of 8-bromo-1,6-naphthyridine-2-carboxamide (0.04 g, 0.16 mmol) and 4-morpholinophenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as yellow solid (0.04 g, 74%). MS: m/e=335.4 [M+H]$^+$.

EXAMPLE 95

8-(4-(Trifluoromethoxy)phenyl)-1,6-naphthyridine-2-carboxamide

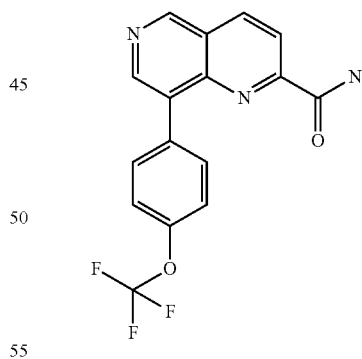

To a suspension of 8-bromo-1,6-naphthyridine-2-carboxamide (0.04 g, 0.16 mmol) and 4-(trifluoromethoxy)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (0.05 g, 85%). MS: m/e=334.3 [M+H]$^+$.

EXAMPLE 96

8-(4-Chlorophenyl)-N-(pyrimidin-4-ylmethyl)-1,6-naphthyridine-2-carboxamide

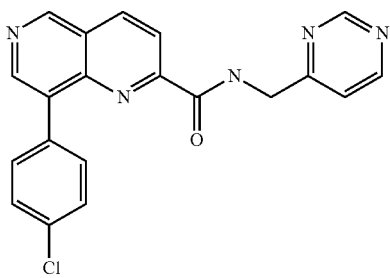 [SMILES: O=C(NCc1ccncn1)c1ccc2cncc(-c3ccc(Cl)cc3)c2n1]

The synthesis was conducted in flow. Reagent solution A contained 8-(4-chlorophenyl)-1,6-naphthyridine-2-carboxylic acid (0.008 g, 0.028 mmol), O-(benzotriazol-1-yl)-N,N,N',N'-tetramethyluronium tetrafluoroborate (TBTU, 0.011 g, 0.034 mmol) and N,N-diisopropylethylamine (0.011 mg, 0.015 ml, 0.084 mmol) in dimethylformamide (0.23 ml) and reagent solution B contained 4-pyridimidinemethanamine (0.105 ml of a 0.4 M stock solution in dimethylformamide, 0.042 mmol) in dimethylformamide (0.145 ml). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as an off-white solid (0.003 g, 27%). MS: m/e=376.4 [M+H]$^+$.

EXAMPLE 97

8-(4-Chlorophenyl)-N-cyclopropyl-N-methyl-1,6-naphthyridine-2-carboxamide

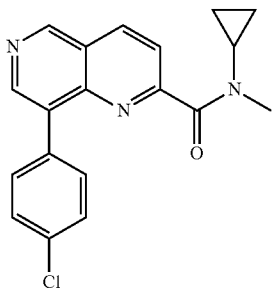

The synthesis was conducted in flow. Reagent solution A contained 8-(4-chlorophenyl)-1,6-naphthyridine-2-carboxylic acid (0.008 g, 0.028 mmol), O-(benzotriazol-1-yl)-N,N,N',N'-tetramethyluronium tetrafluoroborate (TBTU, 0.011 g, 0.034 mmol) and N,N-diisopropylethylamine (0.011 mg, 0.015 ml, 0.084 mmol) in dimethylformamide (0.23 ml) and reagent solution B contained cyclopropylmethylamine (0.105 ml of a 0.4 M stock solution in dimethylformamide, 0.042 mmol) in dimethylformamide (0.145 ml). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as light brown solid (0.005 g, 57%). MS: m/e=338.0 [M+H]$^+$.

EXAMPLE 98

8-(1-Methyl-1H-pyrazol-4-yl)-1,6-naphthyridine-2-carboxamide

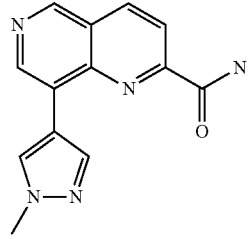 [SMILES: Cn1cc(-c2cncc3ccc(C(N)=O)nc23)cn1]

To a suspension of 8-bromo-1,6-naphthyridine-2-carboxamide (0.04 g, 0.16 mmol) and 1-methyl-4-(4,4,5,5-tetramethyl-1,3,2-dioxaborolan-2-yl)-1H-pyrazole (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, methanol/dichloromethane=0:100 to 20:80) and trituration with diethyl ether yielded the title compound as brown solid (0.04 g, 85%). MS: m/e=254.4 [M+H]$^+$.

EXAMPLE 99

8-(1-Methyl-1H-pyrazol-5-yl)-1,6-naphthyridine-2-carboxamide

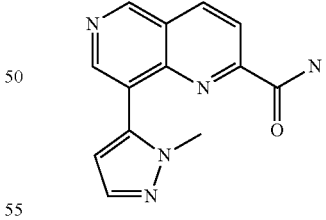

To a suspension of 8-bromo-1,6-naphthyridine-2-carboxamide (0.04 g, 0.16 mmol) and 1-methyl-5-(4,4,5,5-tetramethyl-1,3,2-dioxaborolan-2-yl)-1H-pyrazole (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, methanol/dichloromethane=0:100 to 20:80) and trituration with diethyl ether yielded the title compound as light brown solid (0.03 g, 67%). MS: m/e=254.4 [M+H]$^+$.

EXAMPLE 100

8-(3-(Methoxymethyl)phenyl)-1,6-naphthyridine-2-carboxamide

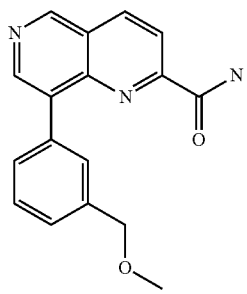 [SMILES: COCc1cccc(-c2cncc3ccc(C(N)=O)nc23)c1]

To a suspension of 8-bromo-1,6-naphthyridine-2-carboxamide (0.04 g, 0.16 mmol) and 3-(methoxymethyl)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.04 g, 84%). MS: m/e=294.4 [M+H]$^+$.

EXAMPLE 101

8-(4-(Trifluoromethyl)phenyl)-1,6-naphthyridine-2-carboxamide

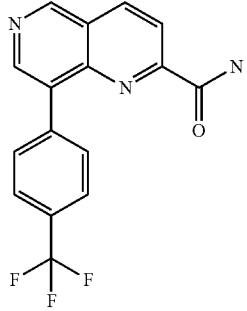 [SMILES: NC(=O)c1ccc2cncc(-c3ccc(C(F)(F)F)cc3)c2n1]

To a suspension of 8-bromo-1,6-naphthyridine-2-carboxamide (0.04 g, 0.16 mmol) and 4-(trifluoromethyl)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.04 g, 83%). MS: m/e=318.4 [M+H]$^+$.

EXAMPLE 102

8-(2,4-Dimethylthiazol-5-yl)-1,6-naphthyridine-2-carboxamide

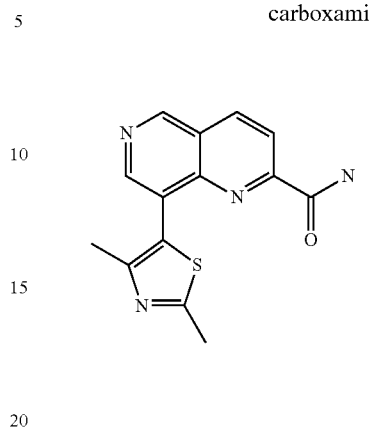

To a suspension of 8-bromo-1,6-naphthyridine-2-carboxamide (0.04 g, 0.16 mmol) and 2,4-dimethyl-5-(4,4,5,5-tetramethyl-1,3,2-dioxaborolan-2-yl)thiazole (0.04 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=20:80 to 100:0) and trituration with diethyl ether yielded the title compound as light brown solid (0.03 g, 67%). MS: m/e=285.4 [M+H]$^+$.

EXAMPLE 103

8-(4-(1H-Pyrazol-1-yl)phenyl)-1,6-naphthyridine-2-carboxamide

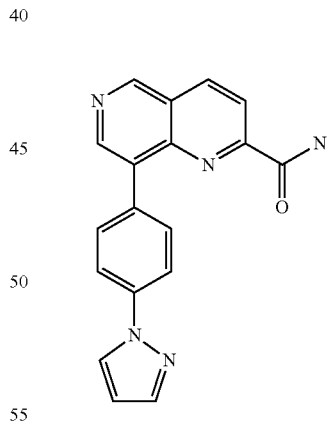

To a suspension of 8-bromo-1,6-naphthyridine-2-carboxamide (0.04 g, 0.16 mmol) and 4-(1H-pyrazol-1-yl)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light green solid (0.05 g, 96%). MS: m/e=316.4 [M+H]$^+$.

EXAMPLE 104

8-(4-(Methoxymethyl)phenyl)-1,6-naphthyridine-2-carboxamide

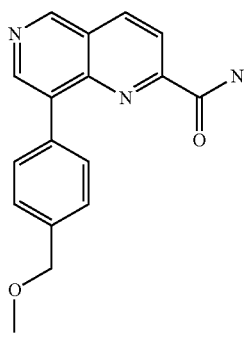 [SMILES: COCc1ccc(-c2cncc3ccc(C(N)=O)nc23)cc1]

To a suspension of 8-bromo-1,6-naphthyridine-2-carboxamide (0.04 g, 0.16 mmol) and 4-(methoxymethyl)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (0.05 g, 97%). MS: m/e=294.4 [M+H]$^+$.

EXAMPLE 105

8-(4-Isopropoxyphenyl)-1,6-naphthyridine-2-carboxamide

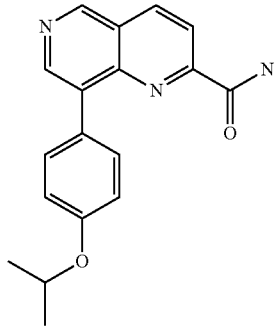 [SMILES: CC(C)Oc1ccc(-c2cncc3ccc(C(N)=O)nc23)cc1]

To a suspension of 8-bromo-1,6-naphthyridine-2-carboxamide (0.04 g, 0.16 mmol) and 4-(isopropoxy)phenylboronic acid (0.03 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as brown solid (0.04 g, 88%). MS: m/e=308.4 [M+H]$^+$.

EXAMPLE 106

8-(4-(N,N-Dimethylsulfamoyl)phenyl)-1,6-naphthyridine-2-carboxamide

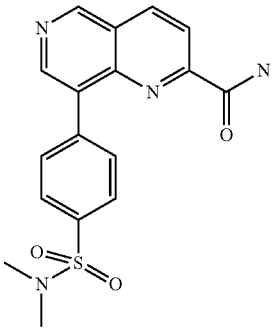 [SMILES: CN(C)S(=O)(=O)c1ccc(-c2cncc3ccc(C(N)=O)nc23)cc1]

To a suspension of 8-bromo-1,6-naphthyridine-2-carboxamide (0.04 g, 0.16 mmol) and N,N-dimethyl-4-(4,4,5,5-tetramethyl-1,3,2-dioxaborolan-2-yl)benzenesulfonamide (0.05 g, 0.16 mmol) and cesium carbonate (0.06 g, 0.18 mmol) in dioxane (5 ml) and water (0.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether yielded the title compound as brown solid (0.02 g, 32%). MS: m/e=357.4 [M+H]$^+$.

EXAMPLE 107

8-(4-Fluorophenyl)-N-(1-(4-(methylsulfonyl)phenyl)ethyl)-1,6-naphthyridine-2-carboxamide

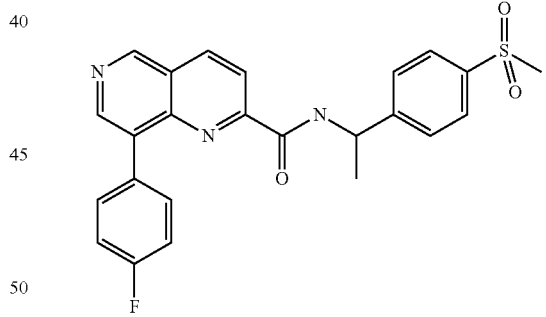

a) 8-Bromo-N-(1-(4-(methylsulfonyl)phenyl)ethyl)-1,6-naphthyridine-2-carboxamide

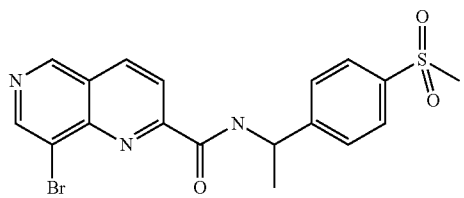 [SMILES: CC(NC(=O)c1ccc2cncc(Br)c2n1)c1ccc(S(C)(=O)=O)cc1]

A mixture of 8-bromo-1,6-naphthyridine-2-carboxylic acid (1.00 g, 3.95 mmol), N,N-diisopropylethylamine (0.62 g, 0.84 ml, 4.82 mmol) and O-(7-azabenzotriazol-1-yl)-N,N,N',N'-tetramethyluronium hexafluorophosphate (HATU, 1.83 g, 4.82 mmol) in dimethylformamide (10 ml) was stirred at room temperature for 2 minutes. 1-(4-(Methylsulfonyl)phenyl)ethanamine hydrochloride (0.79 g, 3.95 mmol) was added and stirring was continued for 2 hours. Extraction with water/ethyl acetate and chromatography (silica gel, ethyl acetate/heptane=50:50 to 100:0) yielded the title compound as orange solid (1.69 g, 94%). MS: m/e=434.3, 436.3 [M+H]⁺.

b) 8-(4-Fluorophenyl)-N-(1-(4-(methylsulfonyl)phenyl)ethyl)-1,6-naphthyridine-2-carboxamide

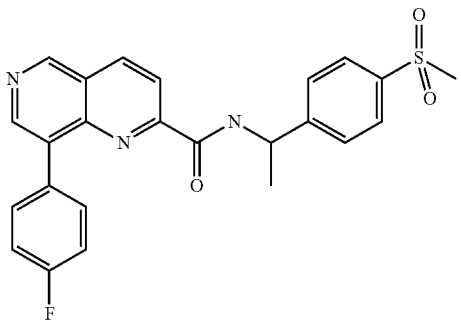 [SMILES: CC(NC(=O)c1ccc2cncc(-c3ccc(F)cc3)c2n1)c1ccc(S(C)(=O)=O)cc1]

To a suspension of 8-bromo-N-(1-(4-(methylsulfonyl)phenyl)ethyl)-1,6-naphthyridine-2-carboxamide (0.05 g, 0.12 mmol) and 4-fluorophenylboronic acid (0.02 g, 0.12 mmol) and cesium carbonate (0.04 g, 0.13 mmol) in dioxane (6.25 ml) and water (2.5 ml) was added bis(diphenylphosphino)ferrocene-palladium(II)dichloride (0.004 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 95%). MS: m/e=450.4 [M+H]⁺.

EXAMPLE 108

8-(2-Fluorophenyl)-N-(1-(4-(methylsulfonyl)phenyl)ethyl)-1,6-naphthyridine-2-carboxamide

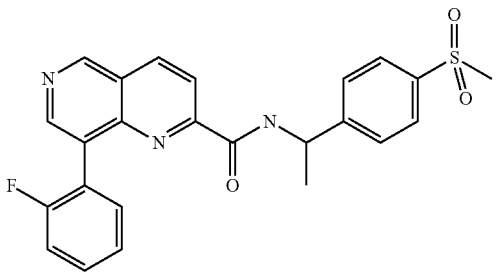

To a suspension of 8-bromo-N-(1-(4-(methylsulfonyl)phenyl)ethyl)-1,6-naphthyridine-2-carboxamide (0.05 g, 0.12 mmol) and 2-fluorophenylboronic acid (0.02 g, 0.12 mmol) and cesium carbonate (0.04 g, 0.13 mmol) in dioxane (6.25 ml) and water (2.5 ml) was added bis(diphenylphosphino)ferrocene-palladium(II)dichloride (0.004 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 93%). MS: m/e=450.4 [M+H]⁺.

EXAMPLE 109

8-(3-Fluorophenyl)-N-(1-(4-(methylsulfonyl)phenyl)ethyl)-1,6-naphthyridine-2-carboxamide

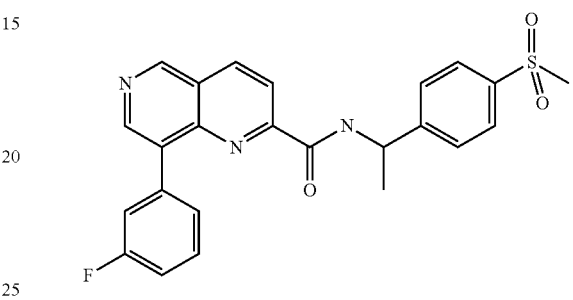

To a suspension of 8-bromo-N-(1-(4-(methylsulfonyl)phenyl)ethyl)-1,6-naphthyridine-2-carboxamide (0.07 g, 0.16 mmol) and 3-fluorophenylboronic acid (0.02 g, 0.12 mmol) and cesium carbonate (0.04 g, 0.13 mmol) in dioxane (6.25 ml) and water (2.5 ml) was added bis(diphenylphosphino)ferrocene-palladium(II)dichloride (0.004 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as light brown solid (0.07 g, 94%). MS: m/e=450.4 [M+H]⁺.

EXAMPLE 110

8-(2,4-Difluorophenyl)-N-(1-(4-(methylsulfonyl)phenyl)ethyl)-1,6-naphthyridine-2-carboxamide

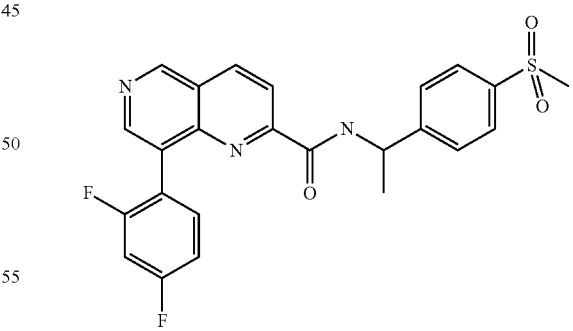

To a suspension of 8-bromo-N-(1-(4-(methylsulfonyl)phenyl)ethyl)-1,6-naphthyridine-2-carboxamide (0.07 g, 0.16 mmol) and 2,4-difluorophenylboronic acid (0.03 g, 0.16 mmol) and cesium carbonate (0.06 g, 0.18 mmol) in dioxane (6.25 ml) and water (2.5 ml) was added bis(diphenylphosphino)ferrocene-palladium(II)dichloride (0.004 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.06 g, 82%). MS: m/e=468.4 [M+H]⁺.

EXAMPLE 111

8-(3,4-Difluorophenyl)-N-(1-(4-(methylsulfonyl)phenyl)ethyl)-1,6-naphthyridine-2-carboxamide

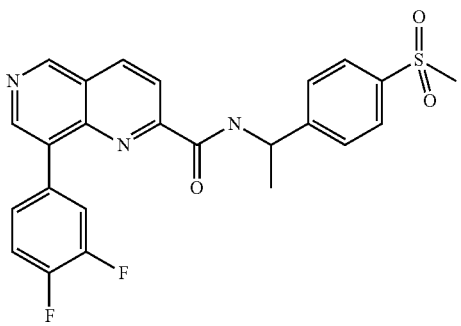 [SMILES: CC(NC(=O)c1ccc2cncc(-c3ccc(F)c(F)c3)c2n1)c1ccc(S(C)(=O)=O)cc1]

To a suspension of 8-bromo-N-(1-(4-(methylsulfonyl)phenyl)ethyl)-1,6-naphthyridine-2-carboxamide (0.07 g, 0.15 mmol) and 3,4-difluorophenylboronic acid (0.02 g, 0.15 mmol) and cesium carbonate (0.05 g, 0.17 mmol) in dioxane (6.25 ml) and water (2.5 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.06 g, 90%). MS: m/e=468.4 [M+H]⁺.

EXAMPLE 112

8-(2-Fluorophenyl)-N-(4-(methylsulfonyl)benzyl)-1,6-naphthyridine-2-carboxamide

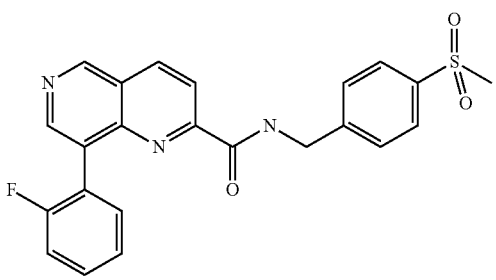

a) 8-Bromo-N-(4-(methylsulfonyl)benzyl)-1,6-naphthyridine-2-carboxamide

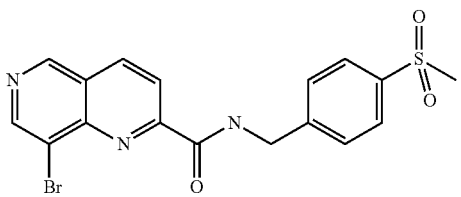 [SMILES: CS(=O)(=O)c1ccc(CNC(=O)c2ccc3cncc(Br)c3n2)cc1]

A mixture of 8-bromo-1,6-naphthyridine-2-carboxylic acid (0.73 g, 2.88 mmol), N,N-diisopropylethylamine (0.83 g, 1.12 ml, 6.40 mmol) and O-(7-azabenzotriazol-1-yl)-N,N,N',N'-tetramethyluronium hexafluorophosphate (HATU, 1.34 g, 3.52 mmol) in dimethylformamide (5 ml) was stirred at room temperature for 2 minutes. (4-(Methylsulfonyl)phenyl)methanamine hydrochloride (0.64 g, 2.88 mmol) was added and stirring was continued for 2 hours. Extraction with water/ethyl acetate and chromatography (silica gel, ethyl acetate/heptane=50:50 to 100:0) yielded the title compound as yellow solid (0.69 g, 57%). MS: m/e=420.3, 422.3 [M+H]⁺.

b) 8-(2-Fluorophenyl)-N-(4-(methylsulfonyl)benzyl)-1,6-naphthyridine-2-carboxamide

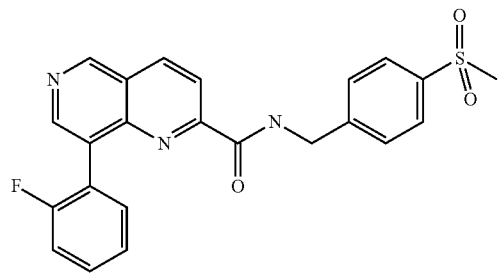

To a suspension of 8-bromo-N-(4-(methylsulfonyl)benzyl)-1,6-naphthyridine-2-carboxamide (0.05 g, 0.12 mmol) and 2-fluorophenylboronic acid (0.02 g, 0.12 mmol) and cesium carbonate (0.04 g, 0.13 mmol) in dioxane (6 ml) and water (0.6 ml) was added bis(diphenylphosphino)ferrocene-palladium(II)dichloride (0.004 g, 0.006 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 95%). MS: m/e=436.5 [M+H]⁺.

EXAMPLE 113

8-(3-Fluorophenyl)-N-(4-(methylsulfonyl)benzyl)-1,6-naphthyridine-2-carboxamide

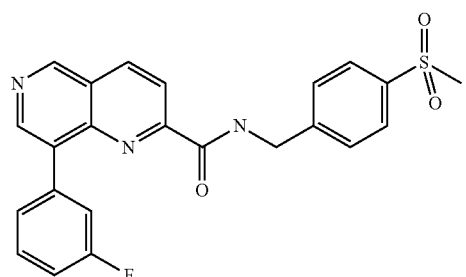

To a suspension of 8-bromo-N-(4-(methylsulfonyl)benzyl)-1,6-naphthyridine-2-carboxamide (0.05 g, 0.12 mmol) and 3-fluorophenylboronic acid (0.02 g, 0.12 mmol) and cesium carbonate (0.04 g, 0.13 mmol) in dioxane (6 ml) and water (0.6 ml) was added bis(diphenylphosphino)ferrocene-palladium(II)dichloride (0.004 g, 0.006 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 96%). MS: m/e=436.5 [M+H]+.

EXAMPLE 114

8-(2,4-Difluorophenyl)-N-(4-(methylsulfonyl)benzyl)-1,6-naphthyridine-2-carboxamide

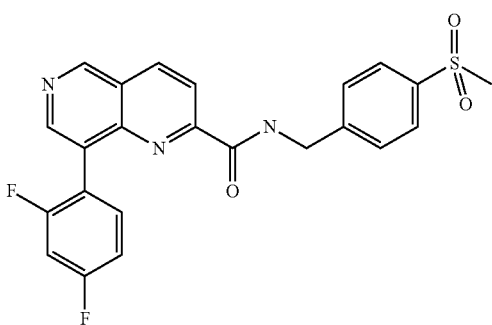

To a suspension of 8-bromo-N-(4-(methylsulfonyl)benzyl)-1,6-naphthyridine-2-carboxamide (0.05 g, 0.12 mmol) and 2,4-difluorophenylboronic acid (0.02 g, 0.12 mmol) and cesium carbonate (0.04 g, 0.13 mmol) in dioxane (6 ml) and water (0.6 ml) was added bis(diphenylphosphino)ferrocenepalladium(II)dichloride (0.004 g, 0.006 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 91%). MS: m/e=454.4 [M+H]+.

EXAMPLE 115

8-(3,4-Difluorophenyl)-N-(4-(methylsulfonyl)benzyl)-1,6-naphthyridine-2-carboxamide

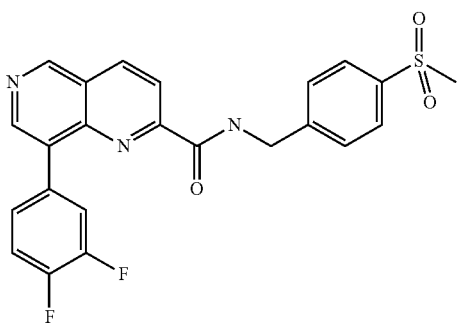 [SMILES: CS(=O)(=O)c1ccc(CNC(=O)c2ccc3cncc(-c4ccc(F)c(F)c4)c3n2)cc1]

To a suspension of 8-bromo-N-(4-(methylsulfonyl)benzyl)-1,6-naphthyridine-2-carboxamide (0.05 g, 0.12 mmol) and 3,4-difluorophenylboronic acid (0.02 g, 0.12 mmol) and cesium carbonate (0.04 g, 0.13 mmol) in dioxane (6 ml) and water (0.6 ml) was added bis(diphenylphosphino)ferrocenepalladium(II)dichloride (0.004 g, 0.006 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 91%). MS: m/e=454.4 [M+H]+.

EXAMPLE 116

8-(2,5-Difluorophenyl)-N-(4-(methylsulfonyl)benzyl)-1,6-naphthyridine-2-carboxamide

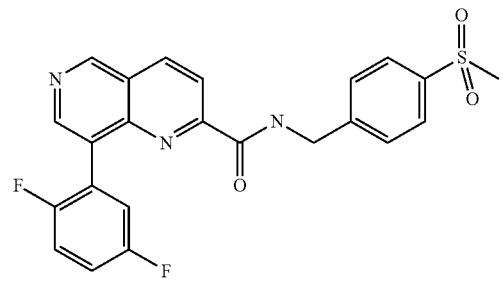 [SMILES: CS(=O)(=O)c1ccc(CNC(=O)c2ccc3cncc(-c4cc(F)ccc4F)c3n2)cc1]

To a suspension of 8-bromo-N-(4-(methylsulfonyl)benzyl)-1,6-naphthyridine-2-carboxamide (0.05 g, 0.12 mmol) and 2,5-difluorophenylboronic acid (0.02 g, 0.12 mmol) and cesium carbonate (0.04 g, 0.13 mmol) in dioxane (6 ml) and water (0.6 ml) was added bis(diphenylphosphino)ferrocenepalladium(II)dichloride (0.004 g, 0.006 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.04 g, 78%). MS: m/e=454.4 [M+H]+.

EXAMPLE 117

8-(4-Fluorophenyl)-N-neopentyl-1,6-naphthyridine-2-carboxamide

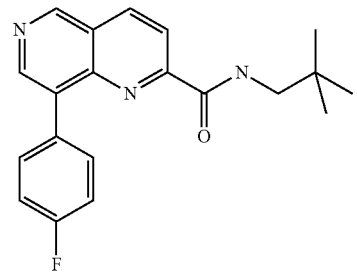 [SMILES: CC(C)(C)CNC(=O)c1ccc2cncc(-c3ccc(F)cc3)c2n1]

a) 8-Bromo-N-neopentyl-1,6-naphthyridine-2-carboxamide

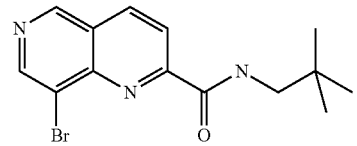 [SMILES: CC(C)(C)CNC(=O)c1ccc2cncc(Br)c2n1]

A mixture of 8-bromo-1,6-naphthyridine-2-carboxylic acid (0.70 g, 2.77 mmol), N,N-diisopropylethylamine (0.79 g, 1.07 ml, 6.14 mmol) and O-(7-azabenzotriazol-1-yl)-N,N,N',N'-tetramethyluronium hexafluorophosphate (HATU, 1.28 g, 3.37 mmol) in dimethylformamide (5 ml) was stirred at room temperature for 2 minutes. 2,2-Dimethylpropan-1-amine (0.24 g, 2.77 mmol) was added and stirring was continued for 2 hours. Extraction with water/ethyl acetate and chromatography (silica gel, ethyl acetate/heptane=50:50 to 100:0) yielded the title compound as yellow oil (0.78 g, 87%). MS: m/e=322.4, 324.4 [M+H]$^+$.

b) 8-(4-Fluorophenyl)-N-neopentyl-1,6-naphthyridine-2-carboxamide

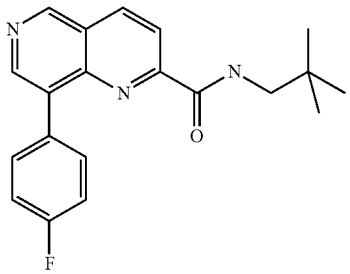

To a suspension of 8-bromo-N-neopentyl-1,6-naphthyridine-2-carboxamide (0.05 g, 0.16 mmol) and 4-fluorophenylboronic acid (0.02 g, 0.16 mmol) and cesium carbonate (0.06 g, 0.17 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.04 g, 75%). MS: m/e=338.5 [M+H]$^+$.

EXAMPLE 118

8-(2-Fluorophenyl)-N-neopentyl-1,6-naphthyridine-2-carboxamide

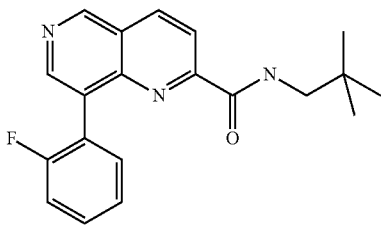

To a suspension of 8-bromo-N-neopentyl-1,6-naphthyridine-2-carboxamide (0.05 g, 0.16 mmol) and 2-fluorophenylboronic acid (0.02 g, 0.16 mmol) and cesium carbonate (0.06 g, 0.17 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 86%). MS: m/e=338.5 [M+H]$^+$.

EXAMPLE 119

8-(3-Fluorophenyl)-N-neopentyl-1,6-naphthyridine-2-carboxamide

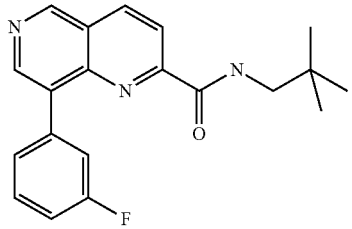

To a suspension of 8-bromo-N-neopentyl-1,6-naphthyridine-2-carboxamide (0.05 g, 0.16 mmol) and 3-fluorophenylboronic acid (0.02 g, 0.16 mmol) and cesium carbonate (0.06 g, 0.17 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) yielded the title compound as brown oil (0.03 g, 61%). MS: m/e=338.5 [M+H]$^+$.

EXAMPLE 120

8-(2,4-Difluorophenyl)-N-neopentyl-1,6-naphthyridine-2-carboxamide

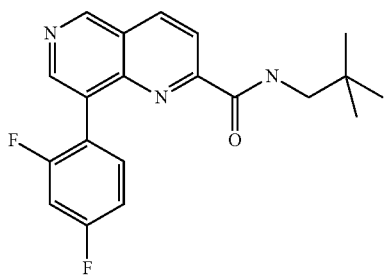 [SMILES: CC(C)(C)CNC(=O)c1ccc2cncc(-c3ccc(F)cc3F)c2n1]

To a suspension of 8-bromo-N-neopentyl-1,6-naphthyridine-2-carboxamide (0.07 g, 0.22 mmol) and 2,4-difluorophenylboronic acid (0.03 g, 0.22 mmol) and cesium carbonate (0.08 g, 0.24 mmol) in dioxane (6 ml) and water (0.6 ml) was added bis(diphenylphosphino)ferrocene-palladium(II) dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as light brown solid (0.07 g, 84%). MS: m/e=356.4 [M+H]$^+$.

EXAMPLE 121

8-(3,4-Difluorophenyl)-N-neopentyl-1,6-naphthyridine-2-carboxamide

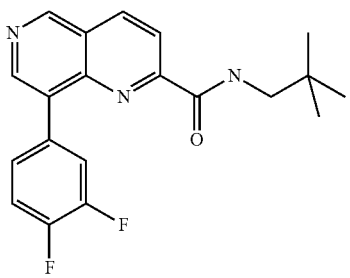 [SMILES: CC(C)(C)CNC(=O)c1ccc2cncc(-c3ccc(F)c(F)c3)c2n1]

To a suspension of 8-bromo-N-neopentyl-1,6-naphthyridine-2-carboxamide (0.07 g, 0.22 mmol) and 3,4-difluorophenylboronic acid (0.03 g, 0.22 mmol) and cesium carbonate (0.08 g, 0.24 mmol) in dioxane (6 ml) and water (0.6 ml) was added bis(diphenylphosphino)ferrocene-palladium(II) dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as light brown solid (0.07 g, 86%). MS: m/e=356.5 [M+H]$^+$.

EXAMPLE 122

8-(2,5-Difluorophenyl)-N-neopentyl-1,6-naphthyridine-2-carboxamide

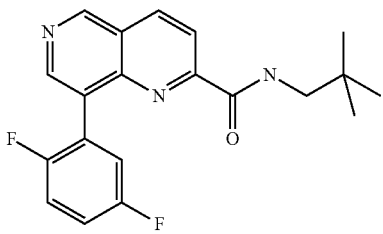 [SMILES: CC(C)(C)CNC(=O)c1ccc2cncc(-c3cc(F)ccc3F)c2n1]

To a suspension of 8-bromo-N-neopentyl-1,6-naphthyridine-2-carboxamide (0.05 g, 0.16 mmol) and 2,5-difluorophenylboronic acid (0.02 g, 0.16 mmol) and cesium carbonate (0.06 g, 0.17 mmol) in dioxane (6 ml) and water (0.6 ml) was added bis(diphenylphosphino)ferrocene-palladium(II) dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as light brown solid (0.05 g, 93%). MS: m/e=356.5 [M+H]$^+$.

EXAMPLE 123

8-(3-Fluorophenyl)-N-(2,2,2-trifluoroethyl)-1,6-naphthyridine-2-carboxamide

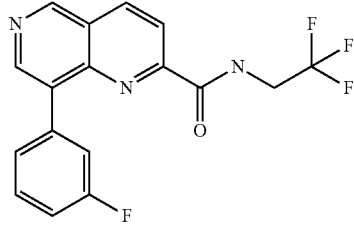 [SMILES: O=C(NCC(F)(F)F)c1ccc2cncc(-c3cccc(F)c3)c2n1]

a) 8-Bromo-N-(2,2,2-trifluoroethyl)-1,6-naphthyridine-2-carboxamide

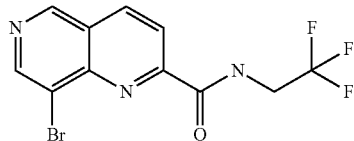 [SMILES: O=C(NCC(F)(F)F)c1ccc2cncc(Br)c2n1]

A mixture of 8-bromo-1,6-naphthyridine-2-carboxylic acid (0.70 g, 2.77 mmol), N,N-diisopropylethylamine (0.79 g, 1.1 ml, 6.14 mmol) and O-(7-azabenzotriazol-1-yl)-N,N,N',N'-tetramethyluronium hexafluorophosphate (HATU, 1.28 g, 3.37 mmol) in dimethylformamide (5 ml) was stirred at room temperature for 2 minutes. 2,2,2-Trifluoroethanamine (0.27 g, 2.77 mmol) was added and stirring was continued for 2 hours. Extraction with water/ethyl acetate and chromatography (silica gel, ethyl acetate/heptane=50:50 to 100:0) yielded the title compound as yellow solid (0.74 g, 80%). MS: m/e=334.3, 336.3 [M+H]$^+$.

b) 8-(3-Fluorophenyl)-N-(2,2,2-trifluoroethyl)-1,6-naphthyridine-2-carboxamide

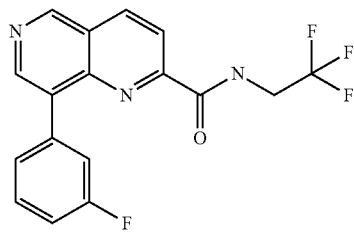

To a suspension of 8-bromo-N-(2,2,2-trifluoroethyl)-1,6-naphthyridine-2-carboxamide (0.07 g, 0.21 mmol) and 3-fluorophenylboronic acid (0.03 g, 0.21 mmol) and cesium carbonate (0.08 g, 0.23 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/

EXAMPLE 124

8-(4-Fluorophenyl)-N-(2,2,2-trifluoroethyl)-1,6-naphthyridine-2-carboxamide

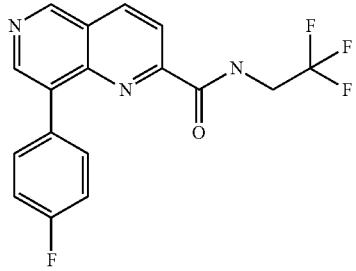 [SMILES: O=C(NCC(F)(F)F)c1ccc2cncc(-c3ccc(F)cc3)c2n1]

To a suspension of 8-bromo-N-(2,2,2-trifluoroethyl)-1,6-naphthyridine-2-carboxamide (0.05 g, 0.15 mmol) and 4-fluorophenylboronic acid (0.02 g, 0.15 mmol) and cesium carbonate (0.05 g, 0.16 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.04 g, 75%). MS: m/e=350.4 [M+H]$^+$.

EXAMPLE 125

8-(2-Fluorophenyl)-N-(2,2,2-trifluoroethyl)-1,6-naphthyridine-2-carboxamide

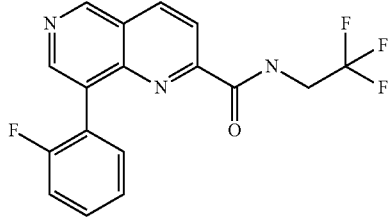 [SMILES: O=C(NCC(F)(F)F)c1ccc2cncc(-c3ccccc3F)c2n1]

To a suspension of 8-bromo-N-(2,2,2-trifluoroethyl)-1,6-naphthyridine-2-carboxamide (0.07 g, 0.21 mmol) and 2-fluorophenylboronic acid (0.03 g, 0.21 mmol) and cesium carbonate (0.08 g, 0.23 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.06 g, 75%). MS: m/e=350.4 [M+H]$^+$.

EXAMPLE 126

8-(2,4-Difluorophenyl)-N-(2,2,2-trifluoroethyl)-1,6-naphthyridine-2-carboxamide

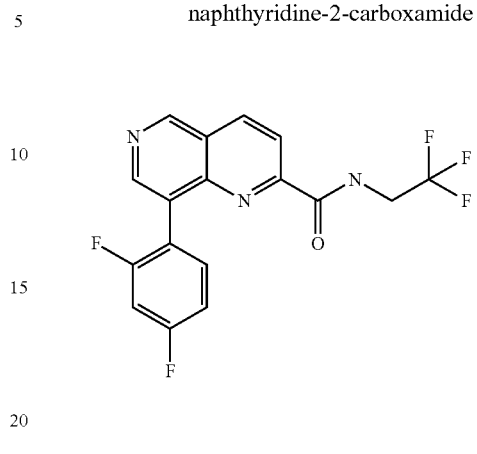

To a suspension of 8-bromo-N-(2,2,2-trifluoroethyl)-1,6-naphthyridine-2-carboxamide (0.07 g, 0.21 mmol) and 2,4-difluorophenylboronic acid (0.03 g, 0.21 mmol) and cesium carbonate (0.08 g, 0.23 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 69%). MS: m/e=368.4 [M+H]$^+$.

EXAMPLE 127

8-(3,4-Difluorophenyl)-N-(2,2,2-trifluoroethyl)-1,6-naphthyridine-2-carboxamide

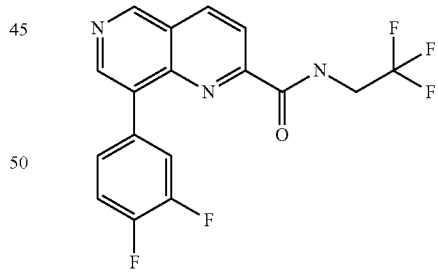

To a suspension of 8-bromo-N-(2,2,2-trifluoroethyl)-1,6-naphthyridine-2-carboxamide (0.07 g, 0.21 mmol) and 3,4-difluorophenylboronic acid (0.03 g, 0.21 mmol) and cesium carbonate (0.08 g, 0.23 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.07 g, 86%). MS: m/e=368.5 [M+H]$^+$.

pentane yielded the title compound as light brown solid (0.07 g, 90%). MS: m/e=350.4 [M+H]$^+$.

EXAMPLE 128

8-(2,5-Difluorophenyl)-N-(2,2,2-trifluoroethyl)-1,6-naphthyridine-2-carboxamide

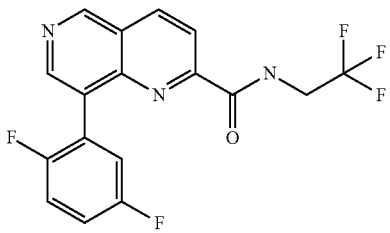

To a suspension of 8-bromo-N-(2,2,2-trifluoroethyl)-1,6-naphthyridine-2-carboxamide (0.07 g, 0.21 mmol) and 2,5-difluorophenylboronic acid (0.03 g, 0.21 mmol) and cesium carbonate (0.08 g, 0.23 mmol) in dioxane (6 ml) and water (0.6 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as brown solid (0.05 g, 62%). MS: m/e=368.4 [M+H]+.

EXAMPLE 129

8-(2,4-Difluorophenyl)-N-(2-(methylsulfonyl)ethyl)-1,6-naphthyridine-2-carboxamide

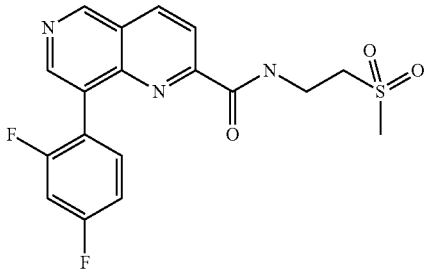 [SMILES: CS(=O)(=O)CCNC(=O)c1ccc2cncc(-c3ccc(F)cc3F)c2n1]

a) 8-Bromo-N-(2-(methylsulfonyl)ethyl)-1,6-naphthyridine-2-carboxamide

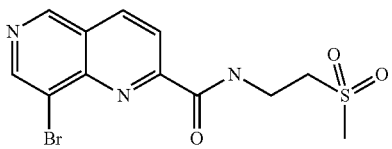 [SMILES: CS(=O)(=O)CCNC(=O)c1ccc2cncc(Br)c2n1]

A mixture of 8-bromo-1,6-naphthyridine-2-carboxylic acid (0.35 g, 1.38 mmol), N,N-diisopropylethylamine (0.40 g, 0.54 ml, 3.07 mmol) and O-(7-azabenzotriazol-1-yl)-N,N,N',N'-tetramethyluronium hexafluorophosphate (HATU, 0.64 g, 1.38 mmol) in dimethylformamide (5 ml) was stirred at room temperature for 2 minutes. 2-(Methylsulfonyl)ethanamine (0.17 g, 1.38 mmol) was added and stirring was continued overnight. Extraction with water/ethyl acetate and chromatography (silica gel, ethyl acetate/heptane=50:50 to 100:0) yielded the title compound as off-white solid (0.27 g, 55%). MS: m/e=358.2, 360.3 [M+H]+.

b) 8-(2,4-Difluorophenyl)-N-(2-(methylsulfonyl)ethyl)-1,6-naphthyridine-2-carboxamide

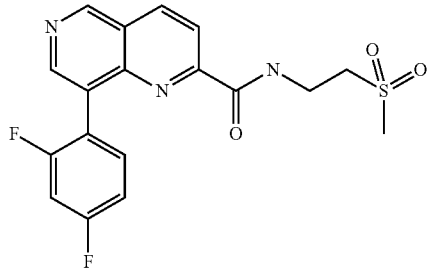 [SMILES: CS(=O)(=O)CCNC(=O)c1ccc2cncc(-c3ccc(F)cc3F)c2n1]

To a suspension of 8-bromo-N-(2-(methylsulfonyl)ethyl)-1,6-naphthyridine-2-carboxamide (0.05 g, 0.14 mmol) and 2,4-difluorophenylboronic acid (0.02 g, 0.14 mmol) and cesium carbonate (0.05 g, 0.15 mmol) in dioxane (6 ml) and water (0.6 ml) was added bis(diphenylphosphino)ferrocene-palladium(II)dichloride (0.01 g, 0.01 mmol). The mixture was stirred at 80° C. for 1.5 hours. Removal of the solvent by distillation and chromatography (silica gel, ethyl acetate/heptane=50:50 to 100:0) and trituration with diethyl ether/pentane yielded the title compound as off-white solid (0.04 g, 73%). MS: m/e=390.4 [M+H]+.

EXAMPLE 130

(8-(4-Chloro-2-fluorophenyl)-1,6-naphthyridin-2-yl)(3-hydroxypyrrolidin-1-yl)methanone

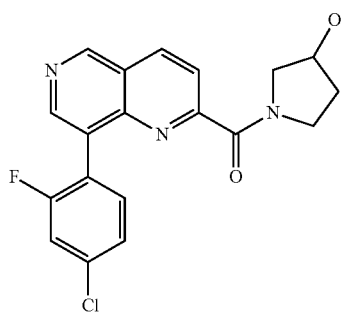 [SMILES: O=C(c1ccc2cncc(-c3ccc(Cl)cc3F)c2n1)N1CCC(O)C1]

a) (8-Bromo-1,6-naphthyridin-2-yl)(3-hydroxypyrrolidin-1-yl)methanone

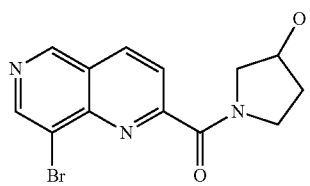 [SMILES: O=C(c1ccc2cncc(Br)c2n1)N1CCC(O)C1]

A mixture of 8-bromo-1,6-naphthyridine-2-carboxylic acid (0.50 g, 1.98 mmol), N,N-diisopropylethylamine (0.57 g, 0.77 ml, 2.22 mmol) and O-(7-azabenzotriazol-1-yl)-N,N,N',N'-tetramethyluronium hexafluorophosphate (HATU, 0.92 g, 2.41 mmol) in dimethylformamide (3 ml) was stirred at room temperature for 2 minutes. Pyrrolidin-3-ol (0.17 g, 1.98 mmol) was added and stirring was continued for 2 hours. Extraction with water/ethyl acetate and chromatography (silica gel, ethyl acetate/heptane=50:50 to 100:0) yielded the title compound as white solid (0.41 g, 64%). MS: m/e=322.4, 324.4 [M+H]$^+$.

b) (8-(4-Chloro-2-fluorophenyl)-1,6-naphthyridin-2-yl)(3-hydroxypyrrolidin-1-yl)methanone

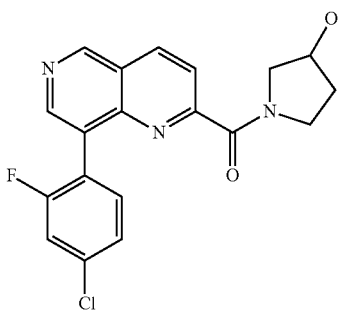

To a suspension of (8-bromo-1,6-naphthyridin-2-yl)(3-hydroxypyrrolidin-1-yl)methanone (0.10 g, 0.31 mmol) and 4-chloro-2-fluorophenylboronic acid (0.05 g, 0.31 mmol) and cesium carbonate (0.11 g, 0.34 mmol) in dioxane (9 ml) and water (0.9 ml) was added bis(diphenylphosphino)ferrocene-palladium(II)dichloride (0.01 g, 0.01 mmol). The mixture was stirred at 80° C. for 1.5 hours. Removal of the solvent by distillation and chromatography (silica gel, ethyl acetate/heptane=50:50 to 100:0) and trituration with diethyl ether/pentane yielded the title compound as light brown solid (0.10 g, 83%). MS: m/e=372.5 [M+H]$^+$.

EXAMPLE 131

(8-(4-Chloro-3-fluorophenyl)-1,6-naphthyridin-2-yl)(3-hydroxypyrrolidin-1-yl)methanone

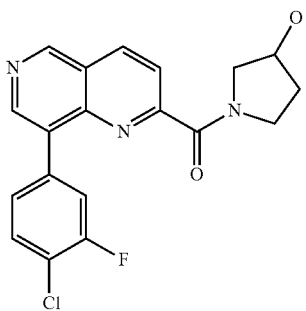

To a suspension of (8-bromo-1,6-naphthyridin-2-yl)(3-hydroxypyrrolidin-1-yl)methanone (0.10 g, 0.31 mmol) and 4-chloro-3-fluorophenylboronic acid (0.05 g, 0.31 mmol) and cesium carbonate (0.11 g, 0.34 mmol) in dioxane (9 ml) and water (0.9 ml) was added bis(diphenylphosphino)ferrocene-palladium(II)dichloride (0.01 g, 0.01 mmol). The mixture was stirred at 80° C. for 2 hours. Removal of the solvent by distillation and chromatography (silica gel, ethyl acetate/heptane=50:50 to 100:0) and trituration with diethyl ether/pentane yielded the title compound as light brown solid (0.11 g, 94%). MS: m/e=372.4 [M+H]$^+$.

EXAMPLE 132

8-(4-Chlorophenyl)-N-(2-(methylsulfonyl)benzyl)-1,6-naphthyridine-2-carboxamide

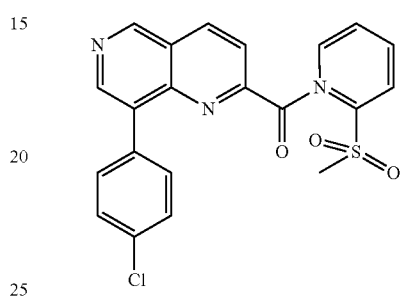

8-(4-Chlorophenyl)-1,6-naphthyridine-2-carboxylic acid (0.10 g, 0.35 mmol) was combined with dichloromethane (10 ml) and 3 drops of dimethylformamide to give a brown suspension. At 0° C. oxalyl chloride (0.07 g, 0.05 ml, 0.53 mmol) was added slowly and the mixture was stirred in an ice bath for 30 minutes and then at room temperature for 1 hour. The solvent was removed by distillation and the residue was added at 0° C. to a solution of (2-(methylsulfonyl)phenyl)methanamine (0.07 g, 0.35 mmol) and triethylamine (0.18 g, 0.25 ml, 1.76 mmol) in dichloromethane (10 ml). The mixture was stirred at 0° C. for 30 minutes and then at room temperature for 3 hours. Extraction with water/ethyl acetate and chromatography (silica gel, ethyl acetate/heptane=50:50 to 100:0) and trituration with diethyl ether/pentane yielded the title compound as brown solid (0.05 g, 30%). MS: m/e=452.4 [M+H]$^+$.

EXAMPLE 133

8-(2-Fluorophenyl)-N-(2-(methylsulfonyl)ethyl)-1,6-naphthyridine-2-carboxamide

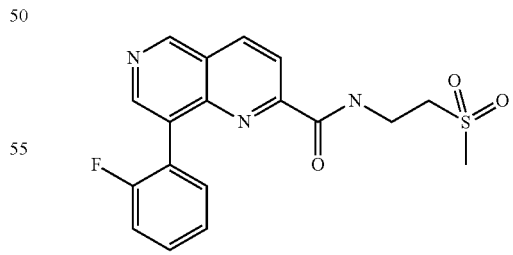

To a suspension of 8-bromo-N-(2-(methylsulfonyl)ethyl)-1,6-naphthyridine-2-carboxamide (0.05 g, 0.14 mmol) and 2-fluorophenylboronic acid (0.02 g, 0.14 mmol) and cesium carbonate (0.05 g, 0.15 mmol) in dioxane (6 ml) and water (0.6 ml) was added bis(diphenylphosphino)ferrocene-palladium(II)dichloride (0.01 g, 0.01 mmol). The mixture was stirred at 80° C. for 1.5 hours. Removal of the solvent by distillation and chromatography (silica gel, ethyl acetate/heptane=50:50 to 100:0) and trituration with diethyl ether/pentane yielded the title compound as light brown solid (0.05 g, 88%). MS: m/e=374.4 [M+H]⁺.

EXAMPLE 134

8-(3-Fluorophenyl)-N-(2-(methylsulfonyl)ethyl)-1,6-naphthyridine-2-carboxamide

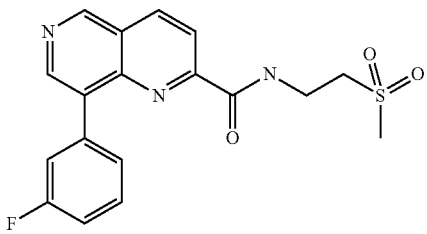 [SMILES: CS(=O)(=O)CCNC(=O)c1ccc2cncc(-c3cccc(F)c3)c2n1]

To a suspension of 8-bromo-N-(2-(methylsulfonyl)ethyl)-1,6-naphthyridine-2-carboxamide (0.05 g, 0.14 mmol) and 3-fluorophenylboronic acid (0.02 g, 0.14 mmol) and cesium carbonate (0.05 g, 0.15 mmol) in dioxane (6 ml) and water (0.6 ml) was added bis(diphenylphosphino)ferrocene-palladium(II)dichloride (0.01 g, 0.01 mmol). The mixture was stirred at 80° C. for 3 hours. Removal of the solvent by distillation and chromatography (silica gel, ethyl acetate/heptane=50:50 to 100:0) and trituration with diethyl ether/pentane yielded the title compound as off-white solid (0.05 g, 99%). MS: m/e=374.5 [M+H]⁺.

EXAMPLE 135

8-(4-Fluorophenyl)-N-(2-(methylsulfonyl)ethyl)-1,6-naphthyridine-2-carboxamide

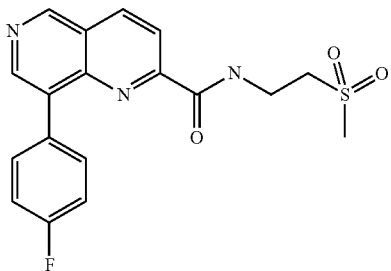 [SMILES: CS(=O)(=O)CCNC(=O)c1ccc2cncc(-c3ccc(F)cc3)c2n1]

To a suspension of 8-bromo-N-(2-(methylsulfonyl)ethyl)-1,6-naphthyridine-2-carboxamide (0.05 g, 0.14 mmol) and 4-fluorophenylboronic acid (0.02 g, 0.14 mmol) and cesium carbonate (0.05 g, 0.15 mmol) in dioxane (6 ml) and water (0.6 ml) was added bis(diphenylphosphino)ferrocene-palladium(II)dichloride (0.01 g, 0.01 mmol). The mixture was stirred at 80° C. for 6 hours. Removal of the solvent by distillation and chromatography (silica gel, ethyl acetate/heptane=50:50 to 100:0) and trituration with diethyl ether/pentane yielded the title compound as off-white solid (0.05 g, 94%). MS: m/e=374.4 [M+H]⁺.

EXAMPLE 136

8-Isobutyl-1,6-naphthyridine-2-carboxamide

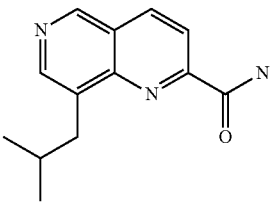 [SMILES: CC(C)Cc1cncc2ccc(C(N)=O)nc12]

a) Isobutyl 8-isobutyl-1,6-naphthyridine-2-carboxylate

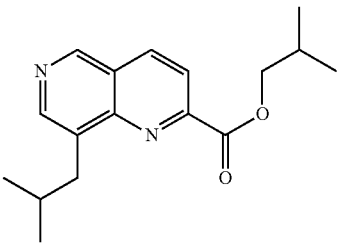 [SMILES: CC(C)COC(=O)c1ccc2cncc(CC(C)C)c2n1]

Methyl 8-bromo-1,6-naphthyridine-2-carboxylate (0.20 g, 0.75 mmol) and bis(diphenylphosphino)ferrocene-palladium(II)dichloride (0.03 g, 0.04 mmol) were combined in tetrahydrofurane (20 ml). Isobutylzinc(II) bromide (0.5M in tetrahydrofurane, 3.15 ml, 1.57 mmol) was added and the mixture was stirred at 50° C. for 2 hours. Extraction with saturated aqueous sodium bicarbonate/ethyl acetate and chromatography (silica gel, ethyl acetate/heptane=20:80 to 100:0) yielded the title compound as brown oil (0.10 g, 45%). MS: m/e=287.5 [M+H]⁺.

b) 8-Isobutyl-1,6-naphthyridine-2-carboxylic acid

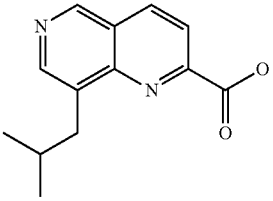 [SMILES: CC(C)Cc1cncc2ccc(C(N)=O)nc12]

Isobutyl 8-isobutyl-1,6-naphthyridine-2-carboxylate (0.09 g, 0.32 mmol) in dioxane (30 ml) was stirred with lithium hydroxide (0.02 g, 0.64 mmol) in water (3 ml) for 3 h. Water (20 ml) was added and the mixture was acidified with 2N aqueous hydrochloric acid. Extraction with ethyl acetate and trituration with diethyl ether yielded the title compound as light brown solid (0.05 g, 73%). MS: m/e=231.4 [M+H]⁺.

c) 8-Isobutyl-1,6-naphthyridine-2-carboxamide

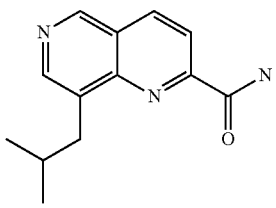

A mixture of 8-isobutyl-1,6-naphthyridine-2-carboxylic acid (0.05 g, 0.22 mmol), 1,1'-carbonyldiimidazole (0.04 g, 0.22 mmol) in dichloromethane (10 ml) was stirred at room temperature for 1 hour. Ammonium hydroxide (5 ml, 128 mmol) was added and stirring was continued for 1 hour. Extraction with water/dichloromethane and trituration with diethyl ether/pentane yielded the title compound as off-white solid (0.02 g, 40%). MS: m/e=230.4 [M+H]$^+$.

EXAMPLE 137

8-(3,4-Difluorophenyl)-N-(2-(methylsulfonyl)ethyl)-1,6-naphthyridine-2-carboxamide

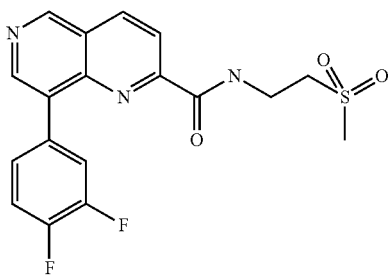 [SMILES: CS(=O)(=O)CCNC(=O)c1ccc2cncc(-c3ccc(F)c(F)c3)c2n1]

To a suspension of 8-bromo-N-(2-(methylsulfonyl)ethyl)-1,6-naphthyridine-2-carboxamide (0.05 g, 0.14 mmol) and 3,4-difluorophenylboronic acid (0.02 g, 0.14 mmol) and cesium carbonate (0.05 g, 0.15 mmol) in dioxane (6 ml) and water (0.6 ml) was added bis(diphenylphosphino)ferrocene-palladium(II)dichloride (0.01 g, 0.01 mmol). The mixture was stirred at 80° C. for 1 hour. Removal of the solvent by distillation and chromatography (silica gel, ethyl acetate/heptane=50:50 to 100:0) and trituration with diethyl ether/pentane yielded the title compound as brown solid (0.05 g, 97%). MS: m/e=392.4 [M+H]$^+$.

EXAMPLE 138

8-(2,5-Difluorophenyl)-N-(2-(methylsulfonyl)ethyl)-1,6-naphthyridine-2-carboxamide

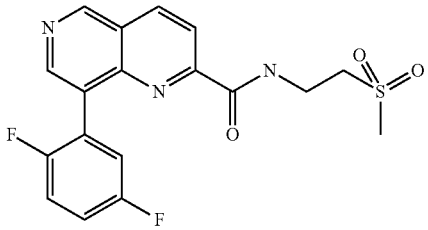 [SMILES: CS(=O)(=O)CCNC(=O)c1ccc2cncc(-c3cc(F)ccc3F)c2n1]

To a suspension of 8-bromo-N-(2-(methylsulfonyl)ethyl)-1,6-naphthyridine-2-carboxamide (0.05 g, 0.14 mmol) and 2,5-difluorophenylboronic acid (0.02 g, 0.14 mmol) and cesium carbonate (0.05 g, 0.15 mmol) in dioxane (6 ml) and water (0.6 ml) was added bis(diphenylphosphino)ferrocene-palladium(II)dichloride (0.01 g, 0.01 mmol). The mixture was stirred at 80° C. for 1 hour. Removal of the solvent by distillation and chromatography (silica gel, ethyl acetate/heptane=50:50 to 100:0) and trituration with diethyl ether/pentane yielded the title compound as off-white solid (0.05 g, 92%). MS: m/e=392.5 [M+H]$^+$.

EXAMPLE 139

8-(4-Chloro-2-fluorophenyl)-N-(2-(methylsulfonyl)ethyl)-1,6-naphthyridine-2-carboxamide

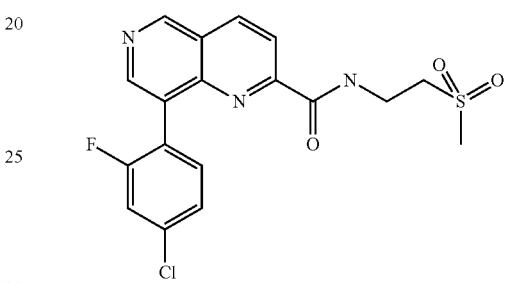

To a suspension of 8-bromo-N-(2-(methylsulfonyl)ethyl)-1,6-naphthyridine-2-carboxamide (0.05 g, 0.14 mmol) and 4-chloro-2-fluorophenylboronic acid (0.02 g, 0.14 mmol) and cesium carbonate (0.05 g, 0.15 mmol) in dioxane (6 ml) and water (0.6 ml) was added bis(diphenylphosphino)ferrocene-palladium(II)dichloride (0.01 g, 0.01 mmol). The mixture was stirred at 80° C. for 2.5 hours. Removal of the solvent by distillation and chromatography (silica gel, ethyl acetate/heptane=50:50 to 100:0) and trituration with diethyl ether/pentane yielded the title compound as grey solid (0.03 g, 58%). MS: m/e=408.4 [M+H]$^+$.

EXAMPLE 140

8-(2-(Dimethylamino)pyridin-4-yl)-1,6-naphthyridine-2-carboxamide

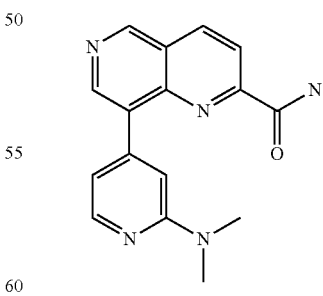

To a suspension of 8-bromo-1,6-naphthyridine-2-carboxamide (0.03 g, 0.12 mmol) and 2-(dimethylamino)pyridin-4-ylboronic acid (0.02 g, 0.12 mmol) and cesium carbonate (0.04 g, 0.13 mmol) in dioxane (5 ml) and water (0.5 ml) was added bis(diphenylphosphino)ferrocene-palladium(II)dichloride (0.005 g, 0.006 mmol). The mixture was stirred at

EXAMPLE 141

8-(4-Chlorophenyl)-N-((2-methyl-5-oxopyrrolidin-2-yl)methyl)-1,6-naphthyridine-2-carboxamide

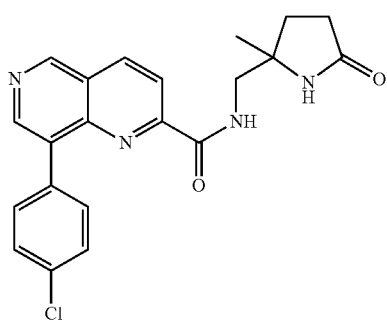 [SMILES: CC1(CNC(=O)c2ccc3cncc(-c4ccc(Cl)cc4)c3n2)CCC(=O)N1]

a) 8-Bromo-N-((2-methyl-5-oxopyrrolidin-2-yl)methyl)-1,6-naphthyridine-2-carboxamide

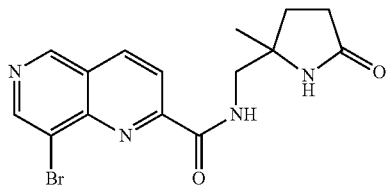 [SMILES: CC1(CNC(=O)c2ccc3cncc(Br)c3n2)CCC(=O)N1]

In a 25 mL round-bottomed flask, 8-bromo-1,6-naphthyridine-2-carboxylic acid (200 mg, 790 μmol) was combined with dichloromethane (10 ml) and 3 drops dimethylformamide to give a light brown suspension. The mixture was cooled in an ice bath and oxalyl chloride (892 mg, 615 μl, 7.03 mmol) was added. The mixture was stirred 30 minutes at 0° C. and 30 minutes at room temperature. The reaction mixture was concentrated in vacuo. The mixture was taken up in dichloromethane (10 ml) and was added to a mixture of 5-(aminomethyl)-5-methylpyrrolidin-2-one hydrochloride (116 mg, 703 μmol) and triethylamine (149 mg, 206 μl, 1.48 mmol) in dichloromethane at 0° C. The reaction mixture was stirred for 45 minutes at 0° C. and then at room temperature overnight. The reaction mixture was poured into 25 ml water and extracted with dichloromethane (4×50 ml). Chromatography (silica gel, methanol/dichloromethane=0:100 to 20:80) yielded the title compound (110 mg, 33%) as off-white solid. MS: m/e=363.4, 365.4 [M+H]⁺.

b) 8-(4-Chlorophenyl)-N-((2-methyl-5-oxopyrrolidin-2-yl)methyl)-1,6-naphthyridine-2-carboxamide

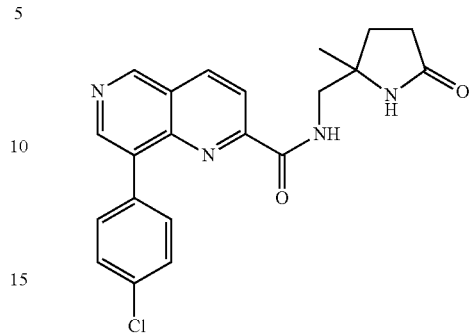

The title compound, light brown solid, (99 mg, 91%), MS: m/e=395.5 [M+H]⁺, was prepared in analogy to the general method of example 2 from 8-bromo-N-((2-methyl-5-oxopyrrolidin-2-yl)methyl)-1,6-naphthyridine-2-carboxamide and 4-chlorophenylboronic acid.

EXAMPLE 142

8-Morpholino-1,6-naphthyridine-2-carboxamide

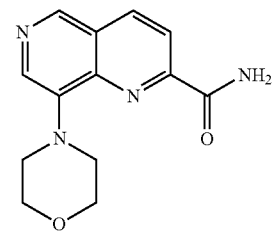

a) Methyl 8-morpholino-1,6-naphthyridine-2-carboxylate

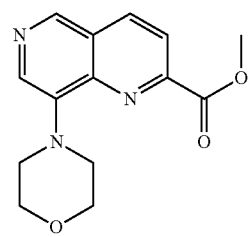 [SMILES: COC(=O)c1ccc2cncc(N3CCOCC3)c2n1]

In a 25 mL three-necked flask, methyl 8-bromo-1,6-naphthyridine-2-carboxylate (50 mg, 187 μmol) and cesium carbonate (183 mg, 562 μmol) were combined with toluene (3 ml) to give a light brown suspension. Under nitrogen palladium (II) acetate (4.2 mg, 18.7 μmol) and (RS)-(±)-2,2'-bis(diphenylphosphino)-1,1'-binaphthyl (BINAP (23.3 mg, 37.4 μmol) and morpholine (24.5 mg, 281 μmol) were added. The reaction mixture was heated to 80° C. and stirred for 15 hours. The crude reaction mixture was concentrated in vacuo and purified by chromatography (silica gel, ethyl acetate/heptane=50:50 to 100:0) to yield the title compound (24 mg, 47%) as yellow solid. MS: m/e=274.4 [M+H]+.

b) 8-Morpholino-1,6-naphthyridine-2-carboxylic acid

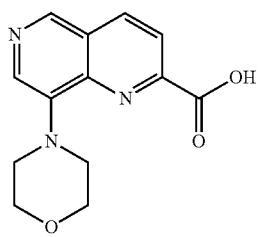 [SMILES: O=C(O)c1ccc2cncc(N3CCOCC3)c2n1]

In a 50 mL round-bottomed flask, methyl 8-morpholino-1,6-naphthyridine-2-carboxylate (275 mg, 1.01 mmol) was combined with dioxane (12 ml) to give an orange solution. Lithium hydroxide (28.9 mg, 1.21 mmol) in water (2 ml) was added and stirring was continued at room temperature for 2 hours. The crude reaction mixture was concentrated in vacuo. The reaction mixture was poured into 25 ml water, acidified with hydrochloric acid (2N) and extracted with ethyl acetate (5×50 ml). The organic layers were dried over magnesium sulfate and concentrated in vacuo. The crude material was triturated with methanol (1 ml), filtered and dried in vacuo to yield the title compound (247 mg, 95%) as orange solid. MS: m/e=260.4 [M+H]+.

c) 8-Morpholino-1,6-naphthyridine-2-carboxamide

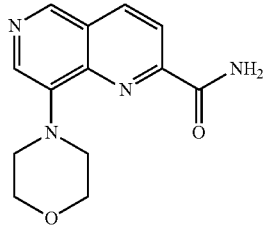 [SMILES: NC(=O)c1ccc2cncc(N3CCOCC3)c2n1]

In a 50 mL round-bottomed flask, 8-morpholino-1,6-naphthyridine-2-carboxylic acid (245 mg, 945 µmol) was combined with dichloromethane (15 ml) to give an orange suspension. 1,1'-Carbonyldiimidazole (153 mg, 945 µmol) was added and stirring was continued at room temperature for 1 hour. Then aqueous ammonium hydroxide (3.6 g, 4 ml, 103 mmol) was added and stirring was continued for 1 hour. The reaction mixture was poured into 20 ml water and extracted with dichloromethane (6×50 ml). The organic layers were dried over magnesium sulfate and concentrated in vacuo. The solid was taken up in dioxane (15.0 ml), 1,1'-carbonyldiimidazole (153 mg, 945 µmol) was added and stirred for 1 hour at room temperature. Then ammonium chloride (505 mg, 9.45 mmol) was added and then slowly triethylamine (956 mg, 1.32 ml, 9.45 mmol) and stirring was continued overnight. The reaction mixture was poured into 25 ml water and extracted with dichloromethane (5×50 ml). Chromatography (silica gel, methanol/dichloromethane=0: 100 to 20:80) yielded the title compound (11 mg, 4.5%) as yellow solid. MS: m/e=259.4 [M+H]+.

EXAMPLE 143

8-(3-Methoxyphenyl)-1,6-naphthyridine-2-carboxamide

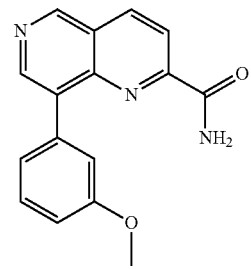 [SMILES: COc1cccc(-c2cncc3ccc(C(N)=O)nc23)c1]

The title compound, off-white solid, (59 mg, 89%), MS: m/e=280.4 [M+H]+, was prepared in analogy to the general method of example 2 from 8-bromo-1,6-naphthyridine-2-carboxamide and 3-methoxyphenylboronic acid.

EXAMPLE 144

N-(2-Hydroxyethyl)-8-(3-hydroxyphenyl)-1,6-naphthyridine-2-carboxamide

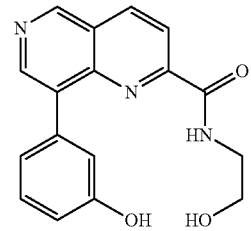

a) 8-Bromo-N-(2-hydroxyethyl)-1,6-naphthyridine-2-carboxamide

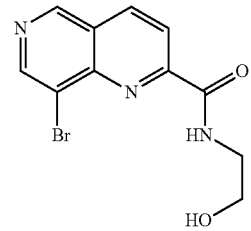 [SMILES: O=C(NCCO)c1ccc2cncc(Br)c2n1]

The title compound, light brown solid, (76 mg, 65%), MS: m/e=296.3, 298.3 [M+H]+, was prepared in analogy to the general method of example 1 from 8-bromo-1,6-naphthyridine-2-carboxylic acid and 2-aminoethanol.

b) N-(2-Hydroxyethyl)-8-(3-hydroxyphenyl)-1,6-naphthyridine-2-carboxamide

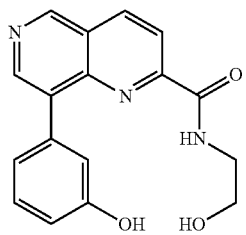

The title compound, grey solid, (71 mg, 97%), MS: m/e=310.4 [M+H]⁺, was prepared in analogy to the general method of example 2 from 8-bromo-N-(2-hydroxyethyl)-1,6-naphthyridine-2-carboxamide and 3-hydroxyphenylboronic acid.

EXAMPLE 145

8-(4-Chlorophenyl)-N-hexyl-1,6-naphthyridine-2-carboxamide

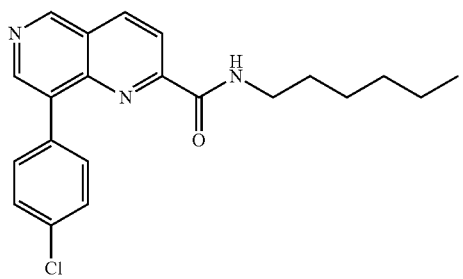

a) 8-Bromo-N-hexyl-1,6-naphthyridine-2-carboxamide

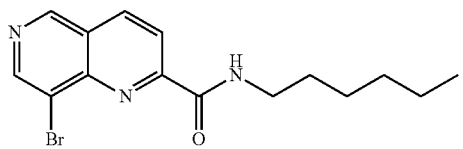 [SMILES: CCCCCCNC(=O)c1ccc2cncc(Br)c2n1]

In a 25 mL round-bottomed flask, 8-bromo-1,6-naphthyridine-2-carboxylic acid (200 mg, 790 µmol) was combined with dichlormethane (10 ml) and 3 drops of dimethylformimde to give a brown suspension. At 0° C. oxalyl chloride (502 mg, 346 µl, 3.95 mmol) was added slowly. The reaction mixture was stirred at 0° C. for 20 min and then at room temperature for 1 hour. The reaction mixture was concentrated in vacuo, taken up in dichloromethane (10 ml) and added slowly to a solution of hexan-1-amine (80.0 mg, 105 µl, 790 µmol) and triethylamine (168 mg, 231 µl, 1.66 mmol) in dichloromethane (10 ml) at 0° C. The mixture was stirred at 0° C. for 30 minutes and then at room temperature for 2 hours. The reaction mixture was poured into 25 ml water and extracted with dichloromethane (5×50 ml). The organic layers were dried over magnesium sulfate and concentrated in vacuo. Chromatography (silica gel, ethyl acetate/heptane=20:80 to 50:50) yielded the title compound (235 mg, 88%) as brown oil. MS: m/e=336.3, 338.4 [M+H]⁺.

b) 8-(4-Chlorophenyl)-N-hexyl-1,6-naphthyridine-2-carboxamide

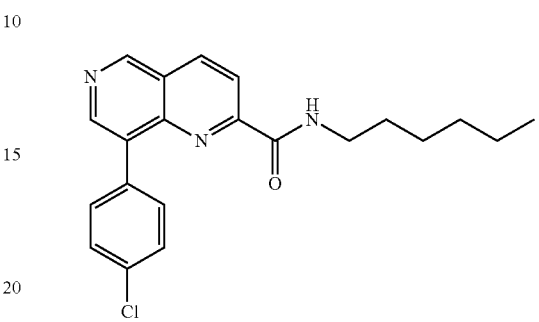

The title compound, off-white solid, (42 mg, 38%), MS: m/e=368.4 [M+H]⁺, was prepared in analogy to the general method of example 2 from 8-bromo-N-hexyl-1,6-naphthyridine-2-carboxamide and 4-chlorophenylboronic acid.

EXAMPLE 146

8-(3,6-Dihydro-2H-pyran-4-yl)-1,6-naphthyridine-2-carboxamide

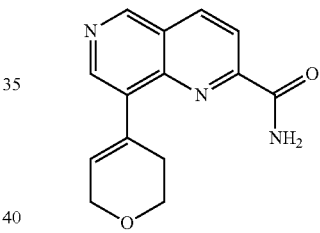

The title compound, off-white solid, (44 mg, 43%), MS: m/e=256.4 [M+H]⁺, was prepared in analogy to the general method of example 2 from 8-bromo-1,6-naphthyridine-2-carboxamide and 2-(3,6-dihydro-2H-pyran-4-yl)-4,4,5,5-tetramethyl-1,3,2-dioxaborolane.

EXAMPLE 147

8-(4-(Hexylcarbamoyl)phenyl)-1,6-naphthyridine-2-carboxamide

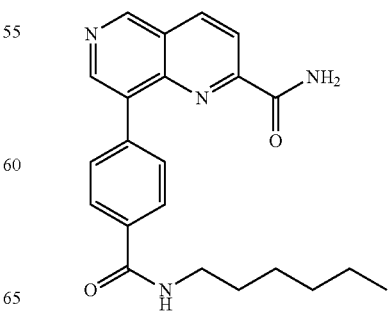

a) 4-(Hexylcarbamoyl)phenylboronic acid

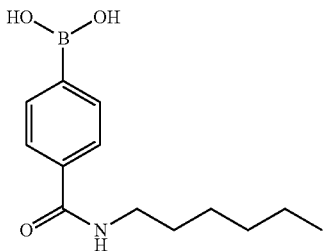 [SMILES: CCCCCCNC(=O)c1ccc(B(O)O)cc1]

In a 25 mL round-bottomed flask, 4-boronobenzoic acid (200 mg, 1.21 mmol) was combined with dichloromethane (15 ml) and 3 drops dimethylformamide to give a light yellow solution. Under cooling oxalyl chloride (765 mg, 528 μl, 6.03 mmol) was added slowly. The reaction mixture was stirred 20 minutes at 0° C. and then for 1 hour at room temperature. The crude reaction mixture was concentrated in vacuo, diluted with dichloromethane (15 ml) and added to a mixture of triethylamine (256 mg, 353 μl, 2.53 mmol) and hexan-1-amine (122 mg, 1.21 mmol) in dichloromethane (15 ml) at 0° C. The mixture was stirred at 0° C. overnight. The reaction mixture was poured into 25 ml water, acidified with conc. hydrochloric acid and extracted with dichloromethane (5×50 ml). The organic layers were dried over magnesium sulfate and concentrated in vacuo. The crude material was triturated with ethyl acetate (2 ml). The solid was filtered through sintered glass and dried in vacuo to yield the title compound (95 mg, 32%) as off-white solid. MS: m/e=248.1 [M−H]+.

b) 8-(4-(Hexylcarbamoyl)phenyl)-1,6-naphthyridine-2-carboxamide

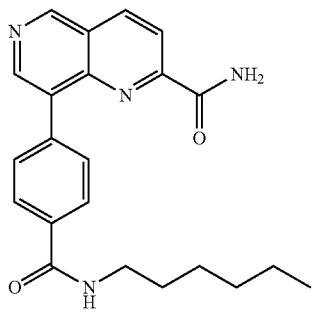

The title compound, off-white solid, (59 mg, 56%), MS: m/e=377.4 [M+H]+, was prepared in analogy to the general method of example 2 from 8-bromo-1,6-naphthyridine-2-carboxamide and 4-(hexylcarbamoyl)phenylboronic acid.

EXAMPLE 148

8-(3-(2-(Hexylamino)-2-oxoethyl)phenyl)-1,6-naphthyridine-2-carboxamide

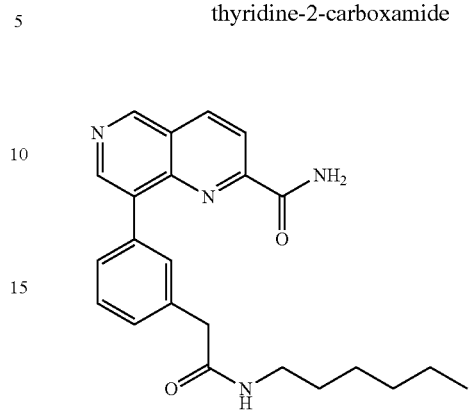

a) 3-(2-(Hexylamino)-2-oxoethyl)phenylboronic acid

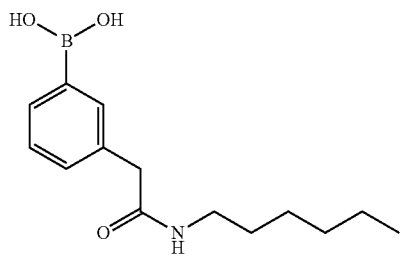 [SMILES: CCCCCCNC(=O)Cc1cccc(B(O)O)c1]

In a 25 mL round-bottomed flask, 2-(3-boronophenyl)acetic acid (200 mg, 1.11 mmol) was combined with dichloromethane (20.0 ml) and 3 drops dimethylformamide to give a light yellow solution. Under cooling oxalyl chloride (705 mg, 486 μl, 5.56 mmol) was added slowly. The mixture was stirred for 20 minutes at 0° C. and then for 1 hour at room temperature. The reaction mixture was concentrated in vacuo, diluted with dichloromethane (20.0 ml) and added to a mixture of triethylamine (236 mg, 325 μl, 2.33 mmol) and hexan-1-amine (112 mg, 1.11 mmol) in dichloromethane (20.0 ml) at 0° C. The mixture was stirred at 0° C. for 30 minutes and then for 2 hours at room temperature. The reaction mixture was concentrated in vacuo, poured into 20 ml 1 M hydrochloric acid and extracted with ethyl acetetae (3×50 ml). The organic layers were dried over magnesium sulfate and concentrated in vacuo. The material was triturated with ethyl acetate (1 ml). The solid was filtered through sintered glass and dried in vacuo to yield the title compound (87 mg, 30%) as off-white solid. MS: m/e=264.4 [M+H]+.

b) 8-(3-(2-(Hexylamino)-2-oxoethyl)phenyl)-1,6-naphthyridine-2-carboxamide

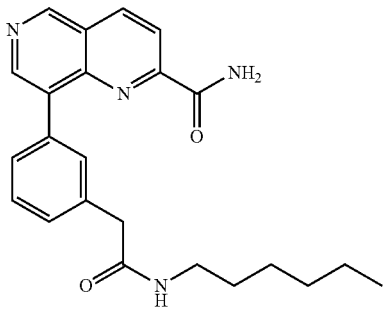 [SMILES: CCCCCCNC(=O)Cc1cccc(-c2cncc3ccc(C(N)=O)nc23)c1]

The title compound, off-white solid, (60 mg, 78%), MS: m/e=391.5 [M+H]$^+$, was prepared in analogy to the general method of example 2 from 8-bromo-1,6-naphthyridine-2-carboxamide and 3-(2-(hexylamino)-2-oxoethyl)phenylboronic acid.

EXAMPLE 149

8-(4-(Heptanamidomethyl)phenyl)-1,6-naphthyridine-2-carboxamide

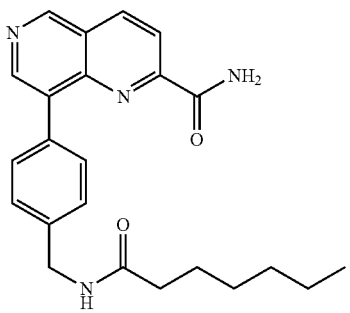 [SMILES: CCCCCCC(=O)NCc1ccc(-c2cncc3ccc(C(N)=O)nc23)cc1]

a) N-(4-(4,4,5,5-Tetramethyl-1,3,2-dioxaborolan-2-yl)benzyl)heptanamide

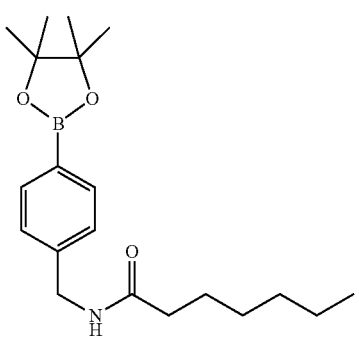 [SMILES: CCCCCCC(=O)NCc1ccc(B2OC(C)(C)C(C)(C)O2)cc1]

In a 50 mL round-bottomed flask, heptanoic acid (275 mg, 2.11 mmol) was combined with dichloromethane (20 ml) and 3 drops dimethylformamide to give a colorless solution. At 0° C. oxalyl chloride (1.34 g, 925 µl, 10.6 mmol) was added slowly and the mixture was stirred for 20 minutes at 0° C. and then for 30 minutes at room temperature. The reaction mixture was concentrated in vacuo, taken up in dichloromethane (20 ml) and was added to a mixture of (4-(4,4,5,5-tetramethyl-1,3,2-dioxaborolan-2-yl)phenyl)methanamine (492 mg, 2.11 mmol) and triethylamine (641 mg, 883 µl, 6.34 mmol) in dichloromethane (20 ml). The reaction mixture was stirred at room temperature for 1 hour. The reaction mixture was poured into 20 ml water and extracted with dichloromethane (5×25 ml). The organic layers were dried over magnesium sulfate and concentrated in vacuo. The mixture was then poured into 20 ml 1 M hydrochloric acid and extracted with ethyl acetate (3×50 ml). The organic layers were dried over magnesium sulfate, concentrated in vacuo and purified by chromatography (silica gel, ethyl acetate/heptane=10:90 to 100:0) to yield the title compound (240 mg, 33%) as yellow oil. MS: m/e=346.5 [M+H]$^+$.

b) 8-(4-(Heptanamidomethyl)phenyl)-1,6-naphthyridine-2-carboxamide

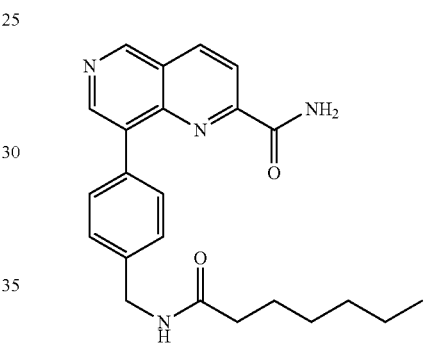

The title compound, off-white solid, (88 mg, 63%), MS: m/e=391.5 [M+H]$^+$, was prepared in analogy to the general method of example 2 from 8-bromo-1,6-naphthyridine-2-carboxamide and N-(4-(4,4,5,5-tetramethyl-1,3,2-dioxaborolan-2-yl)benzyl)heptanamide.

EXAMPLE 150

8-(4-(2-(Hexylamino)-2-oxoethyl)phenyl)-1,6-naphthyridine-2-carboxamide

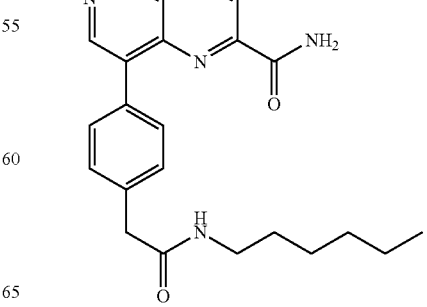

a) 4-(2-(Hexylamino)-2-oxoethyl)phenylboronic acid

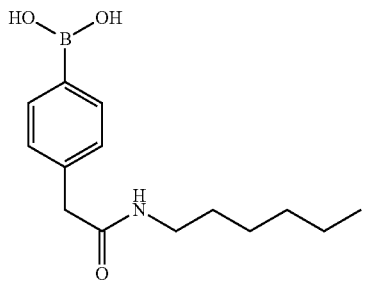 [SMILES: CCCCCCNC(=O)Cc1ccc(B(O)O)cc1]

In a 50 mL round-bottomed flask, 2-(4-boronophenyl)acetic acid (300 mg, 1.67 mmol) was combined with dichloromethane (20 ml) and 3 drops dimethylformamide to give a colorless solution. At 0° C. oxalyl chloride (1.06 g, 730 µl, 8.33 mmol) was added slowly and the mixture was stirred for 20 minutes at 0° C. and then for 30 minutes at room temperature. The reaction mixture was concentrated in vacuo, taken up in dichloromethane (20 ml) and was added to a mixture of hexan-1-amine (169 mg, 1.67 mmol) and triethylamine (506 mg, 697 µl, 5.00 mmol) in dichloromethane (20 ml). The mixture was stirred at room temperature for 1 hour. The reaction mixture was poured into 20 ml water and extracted with dichloromethane (5×25 ml). The organic layers were dried over magnesium sulfate and concentrated in vacuo. The mixture was then poured into 20 ml 1 M hydrochloric acid and extracted with ethyl acetate (3×50 ml). The organic layers were dried over magnesium sulfate and concentrated in vacuo. The material was triturated with ethylacetate (1 ml). The solid was filtered through sintered glass and dried in vacuo to yield the title compound (160 mg, 33%) as light yellow solid. MS: m/e=264.5 [M+H]$^+$.

b) 8-(4-(2-(Hexylamino)-2-oxoethyl)phenyl)-1,6-naphthyridine-2-carboxamide

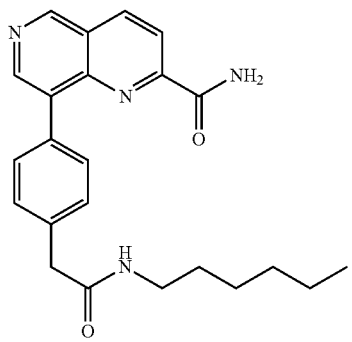

The title compound, off-white solid, (91 mg, 59%), MS: m/e=391.5 [M+H]$^+$, was prepared in analogy to the general method of example 2 from 8-bromo-1,6-naphthyridine-2-carboxamide and 4-(2-(hexylamino)-2-oxoethyl)phenylboronic acid.

EXAMPLE 151

8-(3-(Heptanamidomethyl)phenyl)-1,6-naphthyridine-2-carboxamide

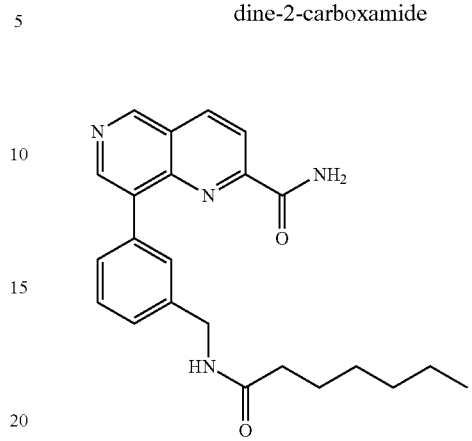

a) 3-(Heptanamidomethyl)phenylboronic acid

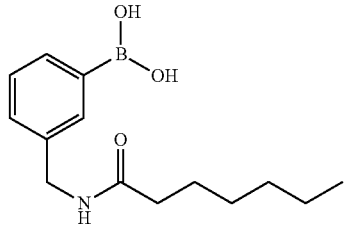 [SMILES: CCCCCCC(=O)NCc1cccc(B(O)O)c1]

In a 50 mL round-bottomed flask, heptanoic acid (300 mg, 2.3 mmol) was combined with dichloromethane (22 ml) and 3 drops dimethylformamide to give a colorless solution. At 0° C. oxalyl chloride (1.46 g, 1.01 ml, 11.5 mmol) was added slowly and the mixture was stirred for 20 minutes at 0° C. and then for 30 minutes at room temperature. The reaction mixture was concentrated in vacuo, taken up in dichloromethane (22 ml) and was added to a mixture of heptanoic acid (300 mg, 2.3 mmol) and triethylamine (1.17 g, 1.61 ml, 11.5 mmol) in dichloromethane (22 ml). The reaction mixture was stirred at room temperature for 1 hour. The reaction mixture was poured into 20 ml water and extracted with dichloromethane (5×25 ml). The organic layers were dried over magnesium sulfate and concentrated in vacuo. The reaction mixture was then poured into 20 ml 1 M hydrochloric acid and extracted with ethyl acetate (3×50 ml). The organic layers were dried over magnesium sulfate, concentrated in vacuo and purified by flash chromatography (silica gel, ethyl acetate/heptane=10:90 to 100:0) to yield the title compound (193 mg, 29%) as yellow solid. MS: m/e=264.5 [M+H]$^+$.

b) 8-(3-(Heptanamidomethyl)phenyl)-1,6-naphthyridine-2-carboxamide

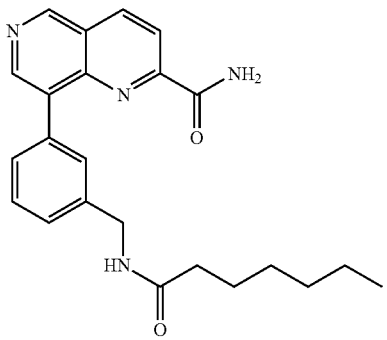 [SMILES: CCCCCCC(=O)NCc1cccc(-c2cncc3ccc(C(N)=O)nc23)c1]

The title compound, light grey solid, (105 mg, 57%), MS: m/e=391.5 [M+H]⁺, was prepared in analogy to the general method of example 2 from 8-bromo-1,6-naphthyridine-2-carboxamide and 3-(heptanamidomethyl)phenylboronic acid.

EXAMPLE 152

8-(4-Chlorophenyl)-3-methyl-1,6-naphthyridine-2-carboxamide

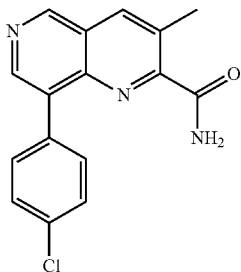 [SMILES: Cc1cc2cncc(-c3ccc(Cl)cc3)c2nc1C(N)=O]

a)
8-Bromo-3-methyl-1,6-naphthyridine-2-carboxamide

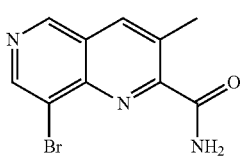

In a 50 mL round-bottomed flask, 8-bromo-3-methyl-1,6-naphthyridine-2-carboxylic acid (CAS 887412-32-0, 145 mg, 543 µmol: 1.00) and 1,1'-carbonyldiimidazole (106 mg, 651 µmol) were combined with dichloromethane (20 ml) to give a yellow solution. The mixture was stirred at room temperature for 1 hour, then ammonium chloride (145 mg, 2.71 mmol) and triethylamine (275 mg, 378 µl, 2.71 mmol) were added and stirring was continued for 3 hours. The crude reaction mixture was concentrated in vacuo and purified by chromatography (silica gel, ethyl acetate/heptane=50:50 to 100:0) to yield the title compound (120 mg, 83%) as light yellow solid. MS: m/e=266.3, 268.2 [M+H]⁺.

b) 8-(4-Chlorophenol)-3-methyl-1,6-naphthyridine-2-carboxamide

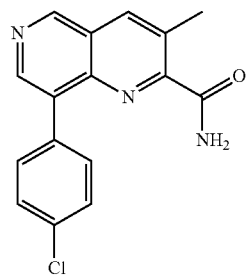 [SMILES: Cc1cc2cncc(-c3ccc(Cl)cc3)c2nc1C(N)=O]

The title compound, off-white solid, (37 mg, 60%), MS: m/e=298.3 [M+H]⁺, was prepared in analogy to the general method of example 2 from 8-bromo-3-methyl-1,6-naphthyridine-2-carboxamide and 4-chlorophenylboronic acid.

EXAMPLE 153

8-(4-Fluorophenyl)-3-methyl-1,6-naphthyridine-2-carboxamide

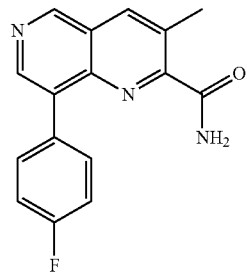 [SMILES: Cc1cc2cncc(-c3ccc(F)cc3)c2nc1C(N)=O]

The title compound, off-white solid, (44 mg, 76%), MS: m/e=282.4 [M+H]⁺, was prepared in analogy to the general method of example 2 from 8-bromo-3-methyl-1,6-naphthyridine-2-carboxamide and 4-fluorophenylboronic acid.

EXAMPLE 154

3-Methyl-8-(4-(trifluoromethoxy)phenyl)-1,6-naphthyridine-2-carboxamide

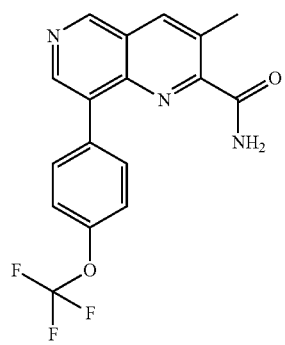 [SMILES: Cc1cc2cncc(-c3ccc(OC(F)(F)F)cc3)c2nc1C(N)=O]

The title compound, off-white solid, (119 mg, 91%), MS: m/e=348.4 [M+H]⁺, was prepared in analogy to the general method of example 2 from 8-bromo-3-methyl-1,6-naphthyridine-2-carboxamide and 4-(trifluoromethoxy)phenylboronic acid.

EXAMPLE 155

8-(4-Cyanophenyl)-3-methyl-1,6-naphthyridine-2-carboxamide

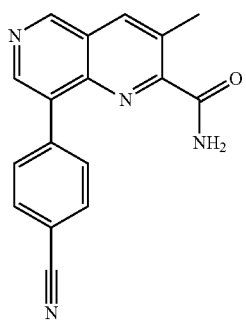 [SMILES: Cc1cc2cncc(-c3ccc(C#N)cc3)c2nc1C(N)=O]

The title compound, light brown solid, (72 mg, 67%), MS: m/e=289.4 [M+H]⁺, was prepared in analogy to the general method of example 2 from 8-bromo-3-methyl-1,6-naphthyridine-2-carboxamide and 4-(4,4,5,5-tetramethyl-1,3,2-dioxaborolan-2-yl)benzonitrile.

EXAMPLE 156

8-(4-(Aminomethyl)phenyl)-1,6-naphthyridine-2-carboxamide

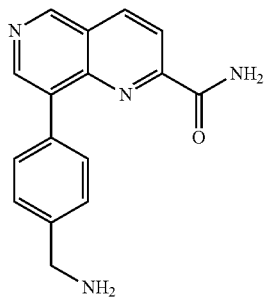 [SMILES: NCc1ccc(-c2cncc3ccc(C(N)=O)nc23)cc1]

The title compound, off-white solid, (131 mg, 79%), MS: m/e=279.4 [M+H]⁺, was prepared in analogy to the general method of example 2 from 8-bromo-1,6-naphthyridine-2-carboxamide and (4-(4,4,5,5-tetramethyl-1,3,2-dioxaborolan-2-yl)phenyl)methanamine.

EXAMPLE 157

3-Methyl-8-[4-(trifluoromethyl)phenyl]-1,6-naphthyridine-2-carboxamide

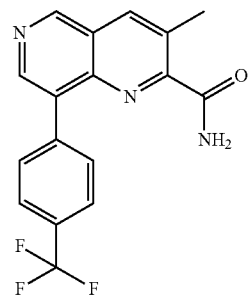 [SMILES: Cc1cc2cncc(-c3ccc(C(F)(F)F)cc3)c2nc1C(N)=O]

The title compound, off-white solid, (62 mg, 62%), MS: m/e=332.3 [M+H]⁺, was prepared in analogy to the general method of example 2 from 8-bromo-3-methyl-1,6-naphthyridine-2-carboxamide and 4-(trifluoromethyl)phenylboronic acid.

EXAMPLE 158

8-(4-Chlorophenyl)-N-(2-hydroxyethyl)-1,6-naphthyridine-2-carboxamide

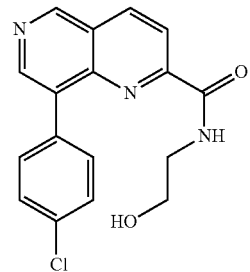 [SMILES: O=C(NCCO)c1ccc2cncc(-c3ccc(Cl)cc3)c2n1]

a) 8-Bromo-N-(2-hydroxyethyl)-1,6-naphthyridine-2-carboxamide

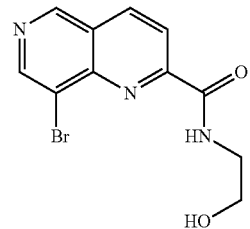 [SMILES: O=C(NCCO)c1ccc2cncc(Br)c2n1]

The title compound, light brown solid, (76 mg, 65%), MS: m/e=296.3, 298.3 [M+H]⁺, was prepared in analogy to the general method of example 1 from 8-bromo-1,6-naphthyridine-2-carboxylic acid and 2-aminoethanol.

b) 8-(4-Chlorophenyl)-N-(2-hydroxyethyl)-1,6-naphthyridine-2-carboxamide

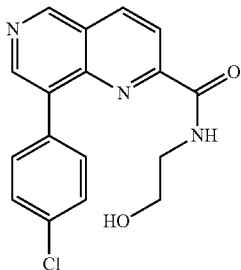 [SMILES: O=C(NCCO)c1ccc2cncc(-c3ccc(Cl)cc3)c2n1]

The title compound, off-white solid, (14.2 mg, 32%), MS: m/e=328.3 [M+H]⁺, was prepared in analogy to the general method of example 2 from 8-bromo-N-(2-hydroxyethyl)-1,6-naphthyridine-2-carboxamide and 4-chlorophenylboronic acid.

EXAMPLE 159

8-(6-Chloropyridin-3-yl)-1,6-naphthyridine-2-carboxamide

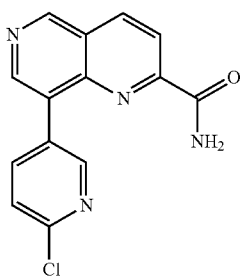 [SMILES: NC(=O)c1ccc2cncc(-c3ccc(Cl)nc3)c2n1]

The title compound, off-white solid, (35 mg, 44%), MS: m/e=285.4 [M+H]⁺, was prepared in analogy to the general method of example 2 from 8-bromo-1,6-naphthyridine-2-carboxamide and 6-chloropyridin-3-ylboronic acid.

EXAMPLE 160

8-(2,4-Dichlorophenyl)-1,6-naphthyridine-2-carboxamide

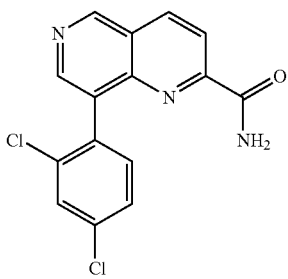 [SMILES: NC(=O)c1ccc2cncc(-c3ccc(Cl)cc3Cl)c2n1]

The title compound, light brown solid, (70 mg, 79%), MS: m/e=318.3, 320.3 [M+H]⁺, was prepared in analogy to the general method of example 2 from 8-bromo-1,6-naphthyridine-2-carboxamide and 2,4-dichlorophenylboronic acid.

EXAMPLE 161

N-(3-Hydroxy-3-methylbutan-2-yl)-8-(4-(trifluoromethyl)phenyl)-1,6-naphthyridine-2-carboxamide

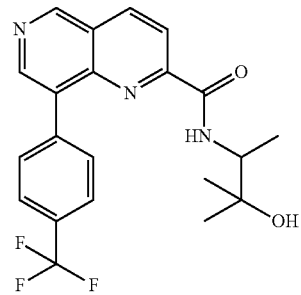 [SMILES: CC(NC(=O)c1ccc2cncc(-c3ccc(C(F)(F)F)cc3)c2n1)C(C)(C)O]

a) 8-Bromo-N-(3-hydroxy-3-methylbutan-2-yl)-1,6-naphthyridine-2-carboxamide

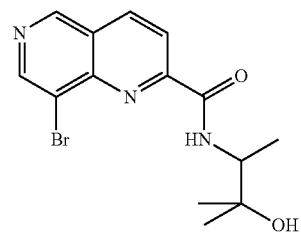 [SMILES: CC(NC(=O)c1ccc2cncc(Br)c2n1)C(C)(C)O]

The title compound, light yellow oil, (220 mg, 82%), MS: m/e=338.1, 340.1 [M+H]⁺, was prepared in analogy to the general method of example 1 from 8-bromo-1,6-naphthyridine-2-carboxylic acid and 3-amino-2-methylbutan-2-ol.

b) N-(3-Hydroxy-3-methylbutan-2-yl)-8-(4-(trifluoromethyl)phenyl)-1,6-naphthyridine-2-carboxamide

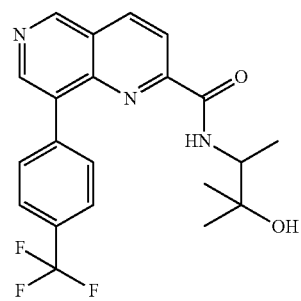 [SMILES: CC(NC(=O)c1ccc2cncc(-c3ccc(C(F)(F)F)cc3)c2n1)C(C)(C)O]

The title compound, off-white solid, (54 mg, 90%), MS: m/e=404.3 [M+H]⁺, was prepared in analogy to the general method of example 2 from 8-bromo-N-(3-hydroxy-3-methylbutan-2-yl)-1,6-naphthyridine-2-carboxamide and 4-(trifluoromethyl)phenylboronic acid.

EXAMPLE 162

8-(4-Chlorophenyl)-N-(3-hydroxy-3-methylbutan-2-yl)-1,6-naphthyridine-2-carboxamide

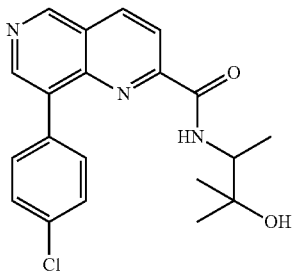 [SMILES: CC(NC(=O)c1ccc2cncc(-c3ccc(Cl)cc3)c2n1)C(C)(C)O]

The title compound, off-white solid, (43 mg, 78%), MS: m/e=370.2 [M+H]$^+$, was prepared in analogy to the general method of example 2 from 8-bromo-N-(3-hydroxy-3-methylbutan-2-yl)-1,6-naphthyridine-2-carboxamide and 4-chlorophenylboronic acid.

EXAMPLE 163

N-(3-Hydroxy-3-methylbutan-2-yl)-8-(4-(2,2,2-trifluoroethoxyl)phenyl)-1,6-naphthyridine-2-carboxamide

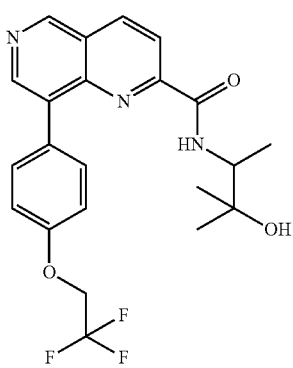

The title compound, off-white solid, (52 mg, 81%), MS: m/e=434.2 [M+H]$^+$, was prepared in analogy to the general method of example 2 from 8-bromo-N-(3-hydroxy-3-methylbutan-2-yl)-1,6-naphthyridine-2-carboxamide and 4-(2,2,2-trifluoroethoxyl)phenylboronic acid.

EXAMPLE 164

N-(3-Hydroxy-3-methylbutan-2-yl)-8-(3-(2,2,2-trifluoroethoxyl)phenyl)-1,6-naphthyridine-2-carboxamide

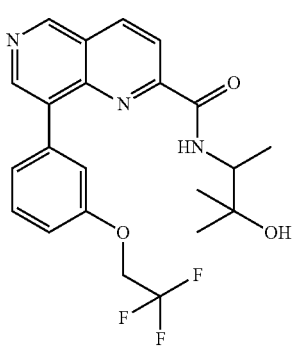 [SMILES: CC(NC(=O)c1ccc2cncc(-c3cccc(OCC(F)(F)F)c3)c2n1)C(C)(C)O]

The title compound, brown foam, (58 mg, 91%), MS: m/e=434.2 [M+H]$^+$, was prepared in analogy to the general method of example 2 from 8-bromo-N-(3-hydroxy-3-methylbutan-2-yl)-1,6-naphthyridine-2-carboxamide and 3-(2,2,2-trifluoroethoxyl)phenylboronic acid.

EXAMPLE 165

8-(4-(2,2,2-Trifluoroethoxyl)phenyl)-1,6-naphthyridine-2-carboxamide

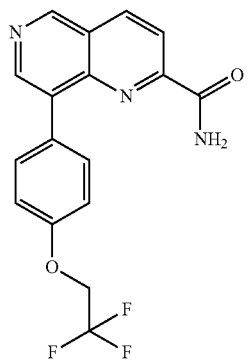 [SMILES: NC(=O)c1ccc2cncc(-c3ccc(OCC(F)(F)F)cc3)c2n1]

The title compound, off-white solid, (45 mg, 65%), MS: m/e=348.1 [M+H]$^+$, was prepared in analogy to the general method of example 2 from 8-bromo-1,6-naphthyridine-2-carboxamide and 4-(2,2,2-trifluoroethoxyl)phenylboronic acid.

EXAMPLE 166

8-(3-(2,2,2-Trifluoroethoxyl)phenyl)-1,6-naphthyridine-2-carboxamide

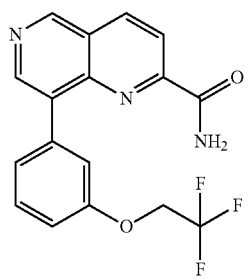

The title compound, colorless solid, (37 mg, 54%), MS: m/e=348.1 [M+H]$^+$, was prepared in analogy to the general method of example 2 from 8-bromo-1,6-naphthyridine-2-carboxamide and 3-(2,2,2-trifluoroethoxyl)phenylboronic acid.

EXAMPLE 167

8-(3-Chlorophenyl)-1,6-naphthyridine-2-carboxamide

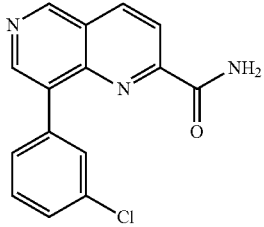 [SMILES: NC(=O)c1ccc2cncc(-c3cccc(Cl)c3)c2n1]

The title compound, off-white solid, (45 mg, 80%), MS: m/e=284.1 [M+H]+, was prepared in analogy to the general method of example 2 from 8-bromo-1,6-naphthyridine-2-carboxamide and 3-chlorophenylboronic acid.

EXAMPLE 168

8-(2-Chlorophenyl)-1,6-naphthyridine-2-carboxamide

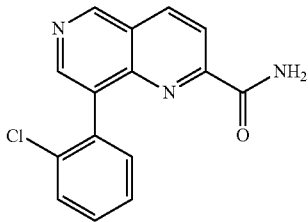 [SMILES: NC(=O)c1ccc2cncc(-c3ccccc3Cl)c2n1]

The title compound, off-white solid, (42 mg, 75%), MS: m/e=284.1 [M+H]+, was prepared in analogy to the general method of example 2 from 8-bromo-1,6-naphthyridine-2-carboxamide and 2-chlorophenylboronic acid.

EXAMPLE 169

8-(4-Chloro-3-fluorophenyl)-1,6-naphthyridine-2-carboxamide

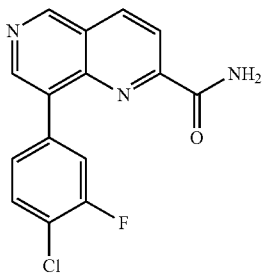 [SMILES: NC(=O)c1ccc2cncc(-c3ccc(Cl)c(F)c3)c2n1]

The title compound, off-white solid, (37 mg, 62%), MS: m/e=302.1 [M+H]+, was prepared in analogy to the general method of example 2 from 8-bromo-1,6-naphthyridine-2-carboxamide and 4-chloro-3-fluorophenylboronic acid.

EXAMPLE 170

8-(4-Chloro-3-fluorophenyl)-N-(3-hydroxy-3-methylbutan-2-yl)-1,6-naphthyridine-2-carboxamide

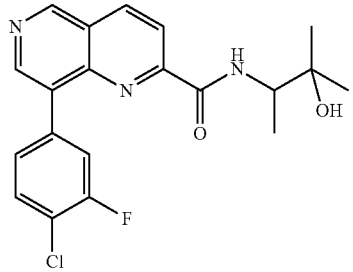 [SMILES: CC(NC(=O)c1ccc2cncc(-c3ccc(Cl)c(F)c3)c2n1)C(C)(C)O]

The title compound, off-white solid, (44 mg, 77%), MS: m/e=388.2 [M+H]+, was prepared in analogy to the general method of example 2 from 8-bromo-N-(3-hydroxy-3-methylbutan-2-yl)-1,6-naphthyridine-2-carboxamide and 4-chloro-3-fluorophenylboronic acid.

EXAMPLE 171

8-(2-Chlorophenyl)-N-(3-hydroxy-3-methylbutan-2-yl)-1,6-naphthyridine-2-carboxamide

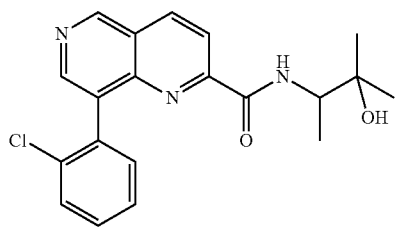 [SMILES: CC(NC(=O)c1ccc2cncc(-c3ccccc3Cl)c2n1)C(C)(C)O]

The title compound, off-white solid, (11 mg, 20%), MS: m/e=370.3 [M+H]+, was prepared in analogy to the general method of example 2 from 8-bromo-N-(3-hydroxy-3-methylbutan-2-yl)-1,6-naphthyridine-2-carboxamide and 2-chlorophenylboronic acid.

EXAMPLE 172

8-(2,4-Dichlorophenyl)-N-(3-hydroxy-3-methylbutan-2-yl)-1,6-naphthyridine-2-carboxamide

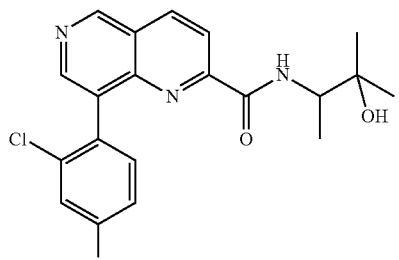

The title compound, off-white solid, (49 mg, 82%), MS: m/e=404.2, 406.2 [M+H]+, was prepared in analogy to the general method of example 2 from 8-bromo-N-(3-hydroxy-3-methylbutan-2-yl)-1,6-naphthyridine-2-carboxamide and 2,4-dichlorophenylboronic acid.

EXAMPLE 173

N-(3-Hydroxy-3-methylbutan-2-yl)-8-(3,4,5-trifluorophenyl)-1,6-naphthyridine-2-carboxamide

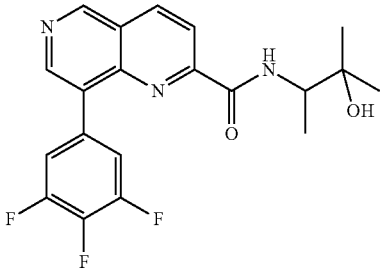 [SMILES: CC(NC(=O)c1ccc2cncc(-c3cc(F)c(F)c(F)c3)c2n1)C(C)(C)O]

The title compound, off-white solid, (36 mg, 63%), MS: m/e=390.2 [M+H]+, was prepared in analogy to the general method of example 2 from 8-bromo-N-(3-hydroxy-3-methylbutan-2-yl)-1,6-naphthyridine-2-carboxamide and 3,4,5-trifluorophenylboronic acid.

EXAMPLE 174

8-(6-Chloropyridin-3-yl)-N-(3-hydroxy-3-methylbutan-2-yl)-1,6-naphthyridine-2-carboxamide

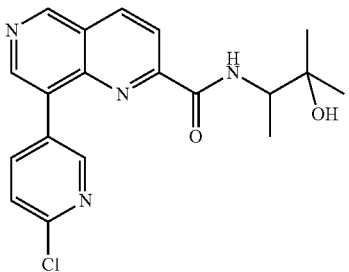

The title compound, off-white solid, (34 mg, 62%), MS: m/e=371.2 [M+H]+, was prepared in analogy to the general method of example 2 from 8-bromo-N-(3-hydroxy-3-methylbutan-2-yl)-1,6-naphthyridine-2-carboxamide and 6-chloropyridin-3-ylboronic acid.

EXAMPLE 175

8-(6-Chloropyridin-2-yl)-N-(3-hydroxy-3-methylbutan-2-yl)-1,6-naphthyridine-2-carboxamide

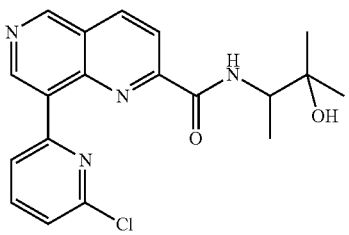

The title compound, off-white solid, (44 mg, 80%), MS: m/e=371.2 [M+H]+, was prepared in analogy to the general method of example 2 from 8-bromo-N-(3-hydroxy-3-methylbutan-2-yl)-1,6-naphthyridine-2-carboxamide and 2-chloro-6-(4,4,5,5-tetramethyl-1,3,2-dioxaborolan-2-yl)pyridine.

EXAMPLE 176

N-(3-Hydroxy-3-methylbutan-2-yl)-8-o-tolyl-1,6-naphthyridine-2-carboxamide

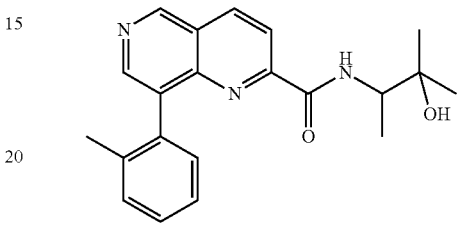

The title compound, off-white solid, (37 mg, 71%), MS: m/e=350.3 [M+H]+, was prepared in analogy to the general method of example 2 from 8-bromo-N-(3-hydroxy-3-methylbutan-2-yl)-1,6-naphthyridine-2-carboxamide and o-tolylboronic acid.

EXAMPLE 177

8-(2-Methyl-4-(trifluoromethyl)phenyl)-1,6-naphthyridine-2-carboxamide

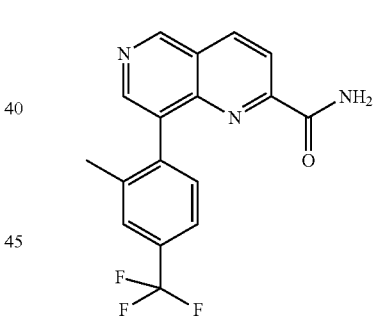

The title compound, off-white solid, (36 mg, 46%), MS: m/e=332.6 [M+H]+, was prepared in analogy to the general method of example 2 from 8-bromo-1,6-naphthyridine-2-carboxamide and 2-methyl-4-(trifluoromethyl)phenylboronic acid.

The invention claimed is:
1. A compounds of formula I

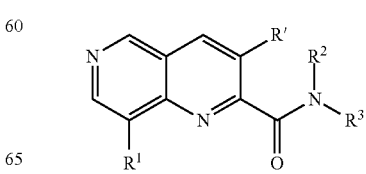

I wherein

R' is hydrogen or lower alkyl;

$R^1$ is cycloalkyl or cyano; or
 is phenyl substituted by one to three substituents selected from, $C_{2-6}$ alkoxy, cyano, C(O)—NH-lower alkyl, $CH_2$—C(O)—NH-lower alkyl, $CH_2$—NH—C(O)-lower alkyl, $CH_2NH_2$, $S(O)_2CH_3$, or $S(O)_2N(CH_3)_2$, groups; or
 is pyrazol-1, 4 or 5-yl, optionally substituted by lower alkyl; or
 is thiazol-5-yl, optionally substituted by one or two lower alkyl groups; or
 is pyridin-3-yl or pyridin-4-yl either optionally substituted by lower alkyl, lower alkoxy, halogen or $N(CH_3)_2$; or
 is 3,6-dihydro-2H-pyran; or
 is benzo[d][1,3]dioxol-5-yl; or
 is 2,3-dihydrobenzo[b][1,4]dioxin-6-yl;

$R^2$ is hydrogen, lower alkyl or lower alkyl substituted by alkoxy;

$R^3$ is hydrogen, lower alkyl, lower alkyl substituted by halogen, lower alkyl substituted by hydroxy, NH—S(O)$_2$—CH$_3$, —(CH$_2$)$_m$—O-lower alkyl or —(CH$_2$)$_n$—S(O)$_2$—CH$_3$; or
 is —(CR$_2$)$_n$-phenyl, optionally substituted by —S(O)$_2$CH$_3$ or lower alkoxy; or
 is —(CH$_2$)$_n$-heterocycloalkyl, optionally substituted by lower alkyl and =O; or
 is —(CH$_2$)$_n$-heteroaryl, optionally substituted by one or two lower alkyl groups wherein the heteroaryl is 4-pyridinyl, 1H-imidazol-1-yl, 1H-pyrazol-1-yl or 1H-pyrazol-4-yl; or
 is —(CH$_2$)$_n$-cycloalkyl, optionally substituted by cyano;
 or $R^2$ and $R^3$ form together with the N atom to which they are attached a heterocyclic ring, selected from morpholine, piperidine, 1,1-dioxo-thiomorpholine or piperazine which may be substituted by lower alkyl or C(O)O-lower alkyl, or may form a pyrrolidine ring, optionally substituted by hydroxy;

R is independently in each occurrence a hydrogen or lower alkyl;

n is 0, 1, 2 or 3;

m is 2;

or a pharmaceutically acceptable acid addition salt, a racemic mixture or its corresponding enantiomer and/or optical isomers thereof.

2. A method for the treatment of depression, anxiety disorders, Parkinson's disease Alzheimer's disease, amyotrophic lateral sclerosis, and stroke, which method comprises administering to a patient in need thereof an effective amount of a compound of a compound of formula I:

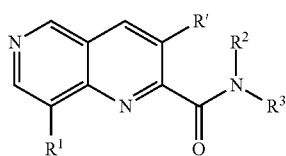

I wherein

R' is hydrogen or lower alkyl;

$R^1$ is halogen, lower alkyl, cycloalkyl or cyano; or
 is phenyl, optionally substituted by one to three substituents, selected from lower alkyl, lower alkyl substituted by halogen, lower alkoxy, lower alkoxy substituted by halogen, cyano, hydroxy, C(O)—NH-lower alkyl, $CH_2$—C(O)—NH-lower alkyl, $CH_2$—NH—C(O)-lower alkyl, $CH_2NH_2$, $S(O)_2CH_3$, $S(O)_2N(CH_3)_2$, or by heterocycloalkyl groups; or
 is pyrazol-1, 4 or 5-yl, optionally substituted by lower alkyl; or
 is thiazol-5-yl, optionally substituted by one or two lower alkyl groups; or
 is pyridine 2, 3 or 4-yl, optionally substituted by lower alkyl, lower alkoxy, halogen or $N(CH_3)_2$; or
 is 3,6-dihydro-2H-pyran; or
 is benzo[d][1,3]dioxol-5-yl; or
 is 2,3-dihydrobenzo[b][1,4]dioxin-6-yl;

$R^2$ is hydrogen, lower alkyl or lower alkyl substituted by alkoxy;

$R^3$ is hydrogen, lower alkyl, lower alkyl substituted by halogen, lower alkyl substituted by hydroxy, NH—S(O)$_2$—CH$_3$, —(CH$_2$)$_m$—O-lower alkyl or —(CH$_2$)$_n$—S(O)$_2$—CH$_3$; or
 is —(CR$_2$)$_n$-phenyl, optionally substituted by —S(O)$_2$CH$_3$ or lower alkoxy; or
 is —(CH$_2$)$_n$-heterocycloalkyl, optionally substituted by lower alkyl and =O; or
 is —(CH$_2$)$_n$-heteroaryl, optionally substituted by one or two lower alkyl groups wherein the heteroaryl is 4-pyridinyl, 1H-imidazol-1-yl, 1H-pyrazol-1-yl or 1H-pyrazol-4-yl; or
 is —(CH$_2$)$_n$-cycloalkyl, optionally substituted by cyano;
 or $R^2$ and $R^3$ form together with the N atom to which they are attached a heterocyclic ring, selected from morpholine, piperidine, 1,1-dioxo-thiomorpholine or piperazine which may be substituted by lower alkyl or C(O)O-lower alkyl, or may form a pyrrolidine ring, optionally substituted by hydroxy;

R is independently in each occurrence a hydrogen or lower alkyl;

n is 0, 1, 2 or 3;

m is 2;

or a pharmaceutically acceptable acid addition salt, a racemic mixture or its corresponding enantiomer and/or optical isomers thereof.

3. The method of claim 2, wherein the compound administered is selected from the group consisting of:

8-Bromo-N-(2-methoxyethyl)-1,6-naphthyridine-2-carboxamide;

N-(2-Methoxyethyl)-8-(4-methoxyphenyl)-1,6-naphthyridine-2-carboxamide;

N-(2-Methoxyethyl)-8-(3-methoxyphenyl)-1,6-naphthyridine-2-carboxamide;

N-(2-Methoxyethyl)-1,6-naphthyridine-2-carboxamide;

N-(2-Methoxyethyl)-8-(2-methoxyphenyl)-1,6-naphthyridine-2-carboxamide;

8-(4-Chlorophenyl)-N-(2-methoxyethyl)-1,6-naphthyridine-2-carboxamide;

8-(3-Chlorophenyl)-N-(2-methoxyethyl)-1,6-naphthyridine-2-carboxamide;

8-(2-Chlorophenyl)-N-(2-methoxyethyl)-1,6-naphthyridine-2-carboxamide;

8-Bromo-[1,6]naphthyridine-2-carboxylic acid (pyridin-4-ylmethyl)-amide;

N-Benzyl-8-bromo-1,6-naphthyridine-2-carboxamide;

N-Benzyl-8-(3-methoxyphenyl)-1,6-naphthyridine-2-carboxamide;

N-Benzyl-8-(2-methoxyphenyl)-1,6-naphthyridine-2-carboxamide;

N-Benzyl-8-(4-chlorophenyl)-1,6-naphthyridine-2-carboxamide;
N-Benzyl-8-(3-chlorophenyl)-1,6-naphthyridine-2-carboxamide;
N-Benzyl-8-(2-chlorophenyl)-1,6-naphthyridine-2-carboxamide;
N-Benzyl-8-(pyridin-4-yl)-1,6-naphthyridine-2-carboxamide;
N-Benzyl-8-(pyridin-3-yl)-1,6-naphthyridine-2-carboxamide;
N-(2-Methoxyethyl)-8-(pyridin-4-yl)-1,6-naphthyridine-2-carboxamide;
N-(2-methoxyethyl)-8-(pyridin-3-yl)-1,6-naphthyridine-2-carboxamide;
8-(4-Methoxyphenyl)-N-phenethyl-1,6-naphthyridine-2-carboxamide;
8-(4-Methoxyphenyl)-1,6-naphthyridine-2-carboxamide;
N-Benzyl-8-(4-methylpyridin-2-yl)-1,6-naphthyridine-2-carboxamide;
8-(4-Methoxyphenyl)-N-(3-phenylpropyl)-1,6-naphthyridine-2-carboxamide;
8-(3-Methoxyphenyl)-N-(pyridin-4-ylmethyl)-1,6-naphthyridine-2-carboxamide;
8-(2-Methoxyphenyl)-N-(pyridin-4-ylmethyl)-1,6-naphthyridine-2-carboxamide;
8-(4-Chlorophenyl)-N-(pyridin-4-ylmethyl)-1,6-naphthyridine-2-carboxamide;
8-(3-Chlorophenyl)-N-(pyridin-4-ylmethyl)-1,6-naphthyridine-2-carboxamide;
8-(2-Chlorophenyl)-N-(pyridin-4-ylmethyl)-1,6-naphthyridine-2-carboxamide;
8-(Pyridin-3-yl)-N-(pyridin-4-ylmethyl)-1,6-naphthyridine-2-carboxamide;
8-(Pyridin-4-yl)-N-(pyridin-4-ylmethyl)-1,6-naphthyridine-2-carboxamide;
N-Benzyl-8-(4-methoxyphenyl)-N-methyl-1,6-naphthyridine-2-carboxamide;
N-Benzyl-N-(2-methoxyethyl)-8-(4-methoxyphenyl)-1,6-naphthyridine-2-carboxamide;
8-(4-Methoxyphenyl)-N-(3,3,3-trifluoropropyl)-1,6-naphthyridine-2-carboxamide;
N-(3-(1H-Imidazol-1-yl)propyl)-8-(3-chlorophenyl)-1,6-naphthyridine-2-carboxamide;
N-(3-(1H-Imidazol-1-yl)propyl)-8-(4-chlorophenyl)-1,6-naphthyridine-2-carboxamide;
N-(3-(1H-Imidazol-1-yl)propyl)-8-(3-methoxyphenyl)-1,6-naphthyridine-2-carboxamide;
N-(3-(1H-Imidazol-1-yl)propyl)-8-(2-methoxyphenyl)-1,6-naphthyridine-2-carboxamide;
N-(3-(1H-Imidazol-1-yl)propyl)-8-(2-chlorophenyl)-1,6-naphthyridine-2-carboxamide;
N-(3-(1H-Imidazol-1-yl)propyl)-8-(pyridin-4-yl)-1,6-naphthyridine-2-carboxamide;
N-(3-(3,5-Dimethyl-1H-pyrazol-1-yl)propyl)-8-(4-methoxyphenyl)-1,6-naphthyridine-2-carboxamide;
N-(3-(1H-Imidazol-1-yl)propyl)-8-(3,6-dihydro-2H-pyran-4-yl)-1,6-naphthyridine-2-carboxamide;
8-(4-Chlorophenyl)-1,6-naphthyridine-2-carboxamide;
8-(4-Chlorophenyl)-N-(2-methoxybenzyl)-1,6-naphthyridine-2-carboxamide;
N'-(8-(4-Chlorophenyl)-1,6-naphthyridine-2-carbonyl)methanesulfonohydrazide;
8-(4-Chlorophenyl)-N-(4-(methylsulfonyl)benzyl)-1,6-naphthyridine-2-carboxamide;
8-(4-Chlorophenyl)-N-(3-(methylsulfonyl)benzyl)-1,6-naphthyridine-2-carboxamide;
(−)-8-(4-Chlorophenyl)-N-(1-(3-(methylsulfonyl)phenyl)ethyl)-1,6-naphthyridine-2-carboxamide;
8-(4-Chlorophenyl)-N-phenyl-1,6-naphthyridine-2-carboxamide;
8-(4-Chlorophenyl)-N-(1-methyl-1H-pyrazol-4-yl)-1,6-naphthyridine-2-carboxamide;
(8-(4-Chlorophenyl)-1,6-naphthyridin-2-yl)(piperidin-1-yl)methanone;
(8-(4-Chlorophenyl)-1,6-naphthyridin-2-yl)(morpholino)methanone;
tert-Butyl 4-(8-(4-chlorophenyl)-1,6-naphthyridine-2-carbonyl)piperazine-1-carboxylate;
8-(4-Chlorophenyl)-N-(piperidin-1-yl)-1,6-naphthyridine-2-carboxamide;
8-(4-Chlorophenyl)-N-(tetrahydrofuran-3-yl)-1,6-naphthyridine-2-carboxamide;
(8-(4-Chlorophenyl)-1,6-naphthyridin-2-yl)(piperazin-1-yl)methanone
8-(4-Chlorophenyl)-N-((2-methyl-5-oxopyrrolidin-2-yl)methyl)-1,6-naphthyridine-2-carboxamide;
8-(4-Chlorophenyl)-N-(2,2,2-trifluoroethyl)-1,6-naphthyridine-2-carboxamide;
8-(4-Chlorophenyl)-N-(3,3,3-trifluoropropyl)-1,6-naphthyridine-2-carboxamide;
8-(4-Chlorophenyl)-N-cyclopropyl-1,6-naphthyridine-2-carboxamide;
8-(4-Chlorophenyl)-N-(cyclopropylmethyl)-N-methyl-1,6-naphthyridine-2-carboxamide;
8-(4-Chlorophenyl)-N-(cyclopropylmethyl)-1,6-naphthyridine-2-carboxamide;
8-(4-Chlorophenyl)-N-neopentyl-1,6-naphthyridine-2-carboxamide;
N-tert-Butyl-8-(4-chlorophenyl)-1,6-naphthyridine-2-carboxamide;
8-(4-Chlorophenyl)-N-isopropyl-1,6-naphthyridine-2-carboxamide;
8-(4-Chlorophenyl)-N-(1-hydroxy-2-methylpropan-2-yl)-1,6-naphthyridine-2-carboxamide;
8-(4-Chlorophenyl)-N-(2-(methylsulfonyl)ethyl)-1,6-naphthyridine-2-carboxamide;
(8-(4-Chlorophenyl)-1,6-naphthyridin-2-yl)(4-methylpiperazin-1-yl)methanone;
[8-(4-Chloro-phenyl)-[1,6]naphthyridin-2-yl]-(1,1-dioxo-thiomorpholin-4-yl)-methanone;
(8-(4-Chlorophenyl)-1,6-naphthyridin-2-yl)(3-hydroxypyrrolidin-1-yl)methanone;
8-(4-Chlorophenyl)-N-(1-cyanocyclopropyl)-1,6-naphthyridine-2-carboxamide;
8-(4-Fluorophenyl)-1,6-naphthyridine-2-carboxamide;
8-(3-Fluorophenyl)-1,6-naphthyridine-2-carboxamide;
8-(2-Fluorophenyl)-1,6-naphthyridine-2-carboxamide;
8-Tolyl-1,6-naphthyridine-2-carboxamide;
8-m-Tolyl-1,6-naphthyridine-2-carboxamide;
8-o-Tolyl-1,6-naphthyridine-2-carboxamide;
8-(3,4-Difluorophenyl)-1,6-naphthyridine-2-carboxamide;
8-(3,4,5-Trifluorophenyl)-1,6-naphthyridine-2-carboxamide;
8-(4-Cyanophenyl)-1,6-naphthyridine-2-carboxamide;
8-(4-(Methylsulfonyl)phenyl)-1,6-naphthyridine-2-carboxamide;
8-(3-(Methylsulfonyl)phenyl)-1,6-naphthyridine-2-carboxamide;
8-(2-(Methylsulfonyl)phenyl)-1,6-naphthyridine-2-carboxamide;
8-(6-Methoxypyridin-3-yl)-1,6-naphthyridine-2-carboxamide;

8-(2-Methylpyridin-4-yl)-1,6-naphthyridine-2-carboxamide;
8-(Benzo[d][1,3]dioxol-5-yl)-1,6-naphthyridine-2-carboxamide;
8-(2,3-Dihydrobenzo[b][1,4]dioxin-6-yl)-1,6-naphthyridine-2-carboxamide;
8-(4-(Trifluoromethoxy)phenyl)-1,6-naphthyridine-2-carboxamide;
8-(4-Chlorophenyl)-N-cyclopropyl-N-methyl-1,6-naphthyridine-2-carboxamide;
8-(1-Methyl-1H-pyrazol-4-yl)-1,6-naphthyridine-2-carboxamide;
8-(1-Methyl-1H-pyrazol-5-yl)-1,6-naphthyridine-2-carboxamide;
8-(3-(Methoxymethyl)phenyl)-1,6-naphthyridine-2-carboxamide;
8-(4-(Trifluoromethyl)phenyl)-1,6-naphthyridine-2-carboxamide;
8-(2,4-Dimethylthiazol-5-yl)-1,6-naphthyridine-2-carboxamide;
8-(4-(1H-Pyrazol-1-yl)phenyl)-1,6-naphthyridine-2-carboxamide;
8-(4-(Methoxymethyl)phenyl)-1,6-naphthyridine-2-carboxamide;
8-(4-Isopropoxyphenyl)-1,6-naphthyridine-2-carboxamide;
8-(4-(N,N-Dimethylsulfamoyl)phenyl)-1, 6-naphthyridine-2-carboxamide;
8-(4-Fluorophenyl)-N-(1-(4-(methylsulfonyl)phenyl) ethyl)-1,6-naphthyridine-2-carboxamide;
8-(2-Fluorophenyl)-N-(1-(4-(methylsulfonyl)phenyl) ethyl)-1,6-naphthyridine-2-carboxamide;
8-(3-Fluorophenyl)-N-(1-(4-(methylsulfonyl)phenyl) ethyl)-1,6-naphthyridine-2-carboxamide;
8-(2,4-Difluorophenyl)-N-(1-(4-(methylsulfonyl)phenyl) ethyl)-1,6-naphthyridine-2-carboxamide;
8-(3,4-Difluorophenyl)-N-(1-(4-(methylsulfonyl)phenyl) ethyl)-1,6-naphthyridine-2-carboxamide;
8-(2-Fluorophenyl)-N-(4-(methylsulfonyl)benzyl)-1,6-naphthyridine-2-carboxamide;
8-(3-Fluorophenyl)-N-(4-(methylsulfonyl)benzyl)-1,6-naphthyridine-2-carboxamide;
8-(2,4-Difluorophenyl)-N-(4-(methylsulfonyl)benzyl)-1, 6-naphthyridine-2-carboxamide;
8-(3,4-Difluorophenyl)-N-(4-(methylsulfonyl)benzyl)-1, 6-naphthyridine-2-carboxamide;
8-(2,5-Difluorophenyl)-N-(4-(methylsulfonyl)benzyl)-1, 6-naphthyridine-2-carboxamide;
8-(4-Fluorophenyl)-N-neopentyl-1,6-naphthyridine-2-carboxamide;
8-(2-Fluorophenyl)-N-neopentyl-1,6-naphthyridine-2-carboxamide;
8-(3-Fluorophenyl)-N-neopentyl-1,6-naphthyridine-2-carboxamide;
8-(2,4-Difluorophenyl)-N-neopentyl-1,6-naphthyridine-2-carboxamide;
8-(3,4-Difluorophenyl)-N-neopentyl-1,6-naphthyridine-2-carboxamide;
8-(2,5-Difluorophenyl)-N-neopentyl-1,6-naphthyridine-2-carboxamide;
8-(3-Fluorophenyl)-N-(2,2,2-trifluoroethyl)-1, 6-naphthyridine-2-carboxamide;
8-(4-Fluorophenyl)-N-(2,2,2-trifluoroethyl)-1, 6-naphthyridine-2-carboxamide;
8-(2-Fluorophenyl)-N-(2,2,2-trifluoroethyl)-1, 6-naphthyridine-2-carboxamide;
8-(2,4-Difluorophenyl)-N-(2,2,2-trifluoroethyl)-1, 6-naphthyridine-2-carboxamide;
8-(3,4-Difluorophenyl)-N-(2,2,2-trifluoroethyl)-1, 6-naphthyridine-2-carboxamide;
8-(2,5-Difluorophenyl)-N-(2,2,2-trifluoroethyl)-1, 6-naphthyridine-2-carboxamide;
8-(2,4-Difluorophenyl)-N-(2-(methylsulfonyl)ethyl)-1, 6-naphthyridine-2-carboxamide;
(8-(4-Chloro-2-fluorophenyl)-1, 6-naphthyridin-2-yl) (3-hydroxypyrrolidin-1-yl)methanone;
(8-(4-Chloro-3-fluorophenyl)-1, 6-naphthyridin-2-yl) (3-hydroxypyrrolidin-1-yl)methanone;
8-(4-Chlorophenyl)-N-(2-(methylsulfonyl)benzyl)-1, 6-naphthyridine-2-carboxamide;
8-(2-Fluorophenyl)-N-(2-(methylsulfonyl)ethyl)-1, 6-naphthyridine-2-carboxamide;
8-(3-Fluorophenyl)-N-(2-(methylsulfonyl)ethyl)-1, 6-naphthyridine-2-carboxamide;
8-(4-Fluorophenyl)-N-(2-(methylsulfonyl)ethyl)-1, 6-naphthyridine-2-carboxamide;
8-Isobutyl-1,6-naphthyridine-2-carboxamide;
8-(3,4-Difluorophenyl)-N-(2-(methylsulfonyl)ethyl)-1,6-naphthyridine-2-carboxamide;
8-(2,5-Difluorophenyl)-N-(2-(methylsulfonyl)ethyl)-1,6-naphthyridine-2-carboxamide;
8-(4-Chloro-2-fluorophenyl)-N-(2-(methylsulfonyl) ethyl)-1,6-naphthyridine-2-carboxamide;
8-(2-(Dimethylamino)pyridin-4-yl)-1,6-naphthyridine-2-carboxamide;
8-(4-Methoxy-phenyl)-[1,6]naphthyridine-2-carboxylic acid (3-imidazol-1-yl-propyl)-amide;
8-(4-Methoxy-phenyl)-[1,6]naphthyridine-2-carboxylic acid (pyridin-4-ylmethyl)-amide;
8-(4-Methoxy-phenyl)-[1,6]naphthyridin-2-yl]-morpholin-4-yl-methanone;
[8-(4-Methoxy-phenyl)-[1,6]naphthyridin-2-yl]-piperidin-1-yl-methanone;
8-(4-Methoxy-phenyl)-[1,6]naphthyridine-2-carboxylic acid benzylamide;
[8-(4-Methoxy-phenyl)-[1,6]naphthyridin-2-yl]-(4-pyridin-2-yl-piperazin-1-yl)-methanone;
8-Phenyl-[1,6]naphthyridine-2-carboxylic acid (3-morpholin-4-yl-propyl)-amide;
8-Phenyl-[1,6]naphthyridine-2-carboxylic acid (3-imidazol-1-yl-propyl)-amide;
8-Phenyl-[1,6]naphthyridine-2-carboxylic acid benzylamide;
(8-Phenyl-[1,6]naphthyridin-2-yl)-(4-pyridin-2-yl-piperazin-1-yl)-methanone;
8-Phenyl-[1,6]naphthyridine-2-carboxylic acid (1-benzyl-piperidin-4-yl)-amide;
8-Phenyl-[1,6]naphthyridine-2-carboxylic acid 2-methoxy-benzylamide;
8-Phenyl-[1,6]naphthyridine-2-carboxylic acid 4-methanesulfonyl-benzylamide;
8-Thiophen-3-yl-[1,6]naphthyridine-2-carboxylic acid (3-imidazol-1-yl-propyl)-amide;
8-Thiophen-3-yl-[1,6]naphthyridine-2-carboxylic acid (pyridin-4-ylmethyl)-amide;
8-Thiophen-3-yl-[1,6]naphthyridine-2-carboxylic acid benzylamide;
(4-Pyridin-2-yl-piperazin-1-yl)-(8-thiophen-3-yl-[1,6] naphthyridin-2-yl)-methanone;
8-Thiophen-3-yl-[1,6]naphthyridine-2-carboxylic acid 4-chloro-benzylamide;
8-Thiophen-3-yl-[1,6]naphthyridine-2-carboxylic acid 2-methoxy-benzylamide;

8-Phenyl-[1,6]naphthyridine-2-carboxylic acid (2-methoxy-ethyl)-amide;
(8-Benzofuran-2-yl-[1,6]naphthyridin-2-yl)-piperidin-1-yl-methanone;
8-Bromo-1,6-naphthyridine-2-carboxamide;
8-Morpholino-1,6-naphthyridine-2-carboxamide;
8-(3-Methoxyphenyl)-1,6-naphthyridine-2-carboxamide;
8-(4-Chlorophenyl)-N-hexyl-1,6-naphthyridine-2-carboxamide;
8-(3,6-Dihydro-2H-pyran-4-yl)-1,6-naphthyridine-2-carboxamide;
8-(4-(Hexylcarbamoyl)phenyl)-1,6-naphthyridine-2-carboxamide;
8-(3-(2-(Hexylamino)-2-oxoethyl)phenyl)-1,6-naphthyridine-2-carboxamide;
8-(4-(Heptanamidomethyl)phenyl)-1,6-naphthyridine-2-carboxamide;
8-(4-(2-(Hexylamino)-2-oxoethyl)phenyl)-1,6-naphthyridine-2-carboxamide;
8-(3-(Heptanamidomethyl)phenyl)-1,6-naphthyridine-2-carboxamide;
8-(4-Chlorophenyl)-3-methyl-1,6-naphthyridine-2-carboxamide;
8-(4-Fluorophenyl)-3-methyl-1,6-naphthyridine-2-carboxamide;
8-(4-Cyanophenyl)-3-methyl-1,6-naphthyridine-2-carboxamide;
8-(4-(Aminomethyl)phenyl)-1,6-naphthyridine-2-carboxamide;
8-(4-Chlorophenyl)-N-(2-hydroxyethyl)-1,6-naphthyridine-2-carboxamide;
8-(6-Chloropyridin-3-yl)-1,6-naphthyridine-2-carboxamide;
8-(2,4-Dichlorophenyl)-1,6-naphthyridine-2-carboxamide;
8-(4-Chlorophenyl)-N-(3-hydroxy-3-methylbutan-2-yl)-1,6-naphthyridine-2-carboxamide;
N-(3-Hydroxy-3-methylbutan-2-yl)-8-(4-(2,2,2-trifluoroethoxy)phenyl)-1,6-naphthyridine-2-carboxamide;
N-(3-Hydroxy-3-methylbutan-2-yl)-8-(3-(2,2,2-trifluoroethoxy)phenyl)-1,6-naphthyridine-2-carboxamide;
8-(4-(2,2,2-Trifluoroethoxy)phenyl)-1,6-naphthyridine-2-carboxamide;
8-(3-(2,2,2-Trifluoroethoxy)phenyl)-1,6-naphthyridine-2-carboxamide;
8-(3-Chlorophenyl)-1,6-naphthyridine-2-carboxamide;
8-(2-Chlorophenyl)-1,6-naphthyridine-2-carboxamide;
8-(4-Chloro-3-fluorophenyl)-1,6-naphthyridine-2-carboxamide;
8-(4-Chloro-3-fluorophenyl)-N-(3-hydroxy-3-methylbutan-2-yl)-1,6-naphthyridine-2-carboxamide;
8-(2-Chlorophenyl)-N-(3-hydroxy-3-methylbutan-2-yl)-1,6-naphthyridine-2-carboxamide;
8-(2,4-Dichlorophenyl)-N-(3-hydroxy-3-methylbutan-2-yl)-1,6-naphthyridine-2-carboxamide;
N-(3-Hydroxy-3-methylbutan-2-yl)-8-(3,4,5-trifluorophenyl)-1,6-naphthyridine-2-carboxamide;
8-(6-Chloropyridin-3-yl)-N-(3-hydroxy-3-methylbutan-2-yl)-1,6-naphthyridine-2-carboxamide;
8-(6-Chloropyridin-2-yl)-N-(3-hydroxy-3-methylbutan-2-yl)-1,6-naphthyridine-2-carboxamide; and, N-(3-Hydroxy-3-methylbutan-2-yl)-8-o-tolyl-1,6-naphthyridine-2-carboxamide; or
a pharmaceutically acceptable salt thereof.

4. The method of claim 3, wherein the compound administered is selected from the group consisting of:

N-(2-Methoxyethyl)-8-(4-methoxyphenyl)-1,6-naphthyridine-2-carboxamide;
N-(2-Methoxyethyl)-8-(3-methoxyphenyl)-1,6-naphthyridine-2-carboxamide;
N-(2-Methoxyethyl)-1,6-naphthyridine-2-carboxamide;
N-(2-Methoxyethyl)-8-(2-methoxyphenyl)-1,6-naphthyridine-2-carboxamide;
8-(4-Chlorophenyl)-N-(2-methoxyethyl)-1,6-naphthyridine-2-carboxamide;
8-(3-Chlorophenyl)-N-(2-methoxyethyl)-1,6-naphthyridine-2-carboxamide;
8-(2-Chlorophenyl)-N-(2-methoxyethyl)-1,6-naphthyridine-2-carboxamide;
8-Bromo-[1,6]naphthyridine-2-carboxylic acid (pyridin-4-ylmethyl)-amide;
N-Benzyl-8-bromo-1,6-naphthyridine-2-carboxamide;
N-Benzyl-8-(3-methoxyphenyl)-1,6-naphthyridine-2-carboxamide;
N-Benzyl-8-(2-methoxyphenyl)-1,6-naphthyridine-2-carboxamide;
N-Benzyl-8-(4-chlorophenyl)-1,6-naphthyridine-2-carboxamide;
N-Benzyl-8-(3-chlorophenyl)-1,6-naphthyridine-2-carboxamide;
N-Benzyl-8-(2-chlorophenyl)-1,6-naphthyridine-2-carboxamide;
N-Benzyl-8-(pyridin-4-yl)-1,6-naphthyridine-2-carboxamide;
N-Benzyl-8-(pyridin-3-yl)-1,6-naphthyridine-2-carboxamide;
N-(2-Methoxyethyl)-8-(pyridin-4-yl)-1,6-naphthyridine-2-carboxamide;
N-(2-methoxyethyl)-8-(pyridin-3-yl)-1,6-naphthyridine-2-carboxamide;
8-(4-Methoxyphenyl)-1,6-naphthyridine-2-carboxamide;
N-Benzyl-8-(4-methylpyridin-2-yl)-1,6-naphthyridine-2-carboxamide;
8-(4-Methoxyphenyl)-N-(3-phenylpropyl)-1,6-naphthyridine-2-carboxamide;
8-(3-Methoxyphenyl)-N-(pyridin-4-ylmethyl)-1,6-naphthyridine-2-carboxamide;
8-(2-Methoxyphenyl)-N-(pyridin-4-ylmethyl)-1,6-naphthyridine-2-carboxamide;
8-(4-Chlorophenyl)-N-(pyridin-4-ylmethyl)-1,6-naphthyridine-2-carboxamide;
8-(3-Chlorophenyl)-N-(pyridin-4-ylmethyl)-1,6-naphthyridine-2-carboxamide;
8-(2-Chlorophenyl)-N-(pyridin-4-ylmethyl)-1,6-naphthyridine-2-carboxamide;
8-(Pyridin-3-yl)-N-(pyridin-4-ylmethyl)-1,6-naphthyridine-2-carboxamide;
8-(Pyridin-4-yl)-N-(pyridin-4-ylmethyl)-1,6-naphthyridine-2-carboxamide;
N-Benzyl-8-(4-methoxyphenyl)-N-methyl-1,6-naphthyridine-2-carboxamide;
N-Benzyl-N-(2-methoxyethyl)-8-(4-methoxyphenyl)-1,6-naphthyridine-2-carboxamide;
8-(4-Methoxyphenyl)-N-(3,3,3-trifluoropropyl)-1,6-naphthyridine-2-carboxamide;
N-(3-(1H-Imidazol-1-yl)propyl)-8-(3-chlorophenyl)-1,6-naphthyridine-2-carboxamide;
N-(3-(1H-Imidazol-1-yl)propyl)-8-(4-chlorophenyl)-1,6-naphthyridine-2-carboxamide;
N-(3-(1H-Imidazol-1-yl)propyl)-8-(3-methoxyphenyl)-1,6-naphthyridine-2-carboxamide;
N-(3-(1H-Imidazol-1-yl)propyl)-8-(2-methoxyphenyl)-1,6-naphthyridine-2-carboxamide;

N-(3-(1H-Imidazol-1-yl)propyl)-8-(2-chlorophenyl)-1,6-naphthyridine-2-carboxamide;
N-(3-(1H-Imidazol-1-yl)propyl)-8-(pyridin-4-yl)-1,6-naphthyridine-2-carboxamide;
N-(3-(3,5-Dimethyl-1H-pyrazol-1-yl)propyl)-8-(4-methoxyphenyl)-1,6-naphthyridine-2-carboxamide;
N-(3-(1H-Imidazol-1-yl)propyl)-8-(3,6-dihydro-2H-pyran-4-yl)-1,6-naphthyridine-2-carboxamide;
8-(4-Chlorophenyl)-1,6-naphthyridine-2-carboxamide;
8-(4-Chlorophenyl)-N-(2-methoxybenzyl)-1,6-naphthyridine-2-carboxamide;
N'-(8-(4-Chlorophenyl)-1,6-naphthyridine-2-carbonyl)methanesulfonohydrazide;
8-(4-Chlorophenyl)-N-(4-(methylsulfonyl)benzyl)-1,6-naphthyridine-2-carboxamide;
8-(4-Chlorophenyl)-N-(3-(methylsulfonyl)benzyl)-1,6-naphthyridine-2-carboxamide;
(−)-8-(4-Chlorophenyl)-N-(1-(3-(methylsulfonyl)phenyl)ethyl)-1,6-naphthyridine-2-carboxamide;
8-(4-Chlorophenyl)-N-phenyl-1,6-naphthyridine-2-carboxamide;
8-(4-Chlorophenyl)-N-(1-methyl-1H-pyrazol-4-yl)-1,6-naphthyridine-2-carboxamide;
(8-(4-Chlorophenyl)-1,6-naphthyridin-2-yl)(piperidin-1-yl)methanone;
(8-(4-Chlorophenyl)-1,6-naphthyridin-2-yl)(morpholino)methanone;
tert-Butyl 4-(8-(4-chlorophenyl)-1,6-naphthyridine-2-carbonyl)piperazine-1-carboxylate;
8-(4-Chlorophenyl)-N-(piperidin-1-yl)-1,6-naphthyridine-2-carboxamide;
8-(4-Chlorophenyl)-N-(tetrahydrofuran-3-yl)-1,6-naphthyridine-2-carboxamide;
(8-(4-Chlorophenyl)-1,6-naphthyridin-2-yl)(piperazin-1-yl)methanone;
8-(4-Chlorophenyl)-N-((2-methyl-5-oxopyrrolidin-2-yl)methyl)-1,6-naphthyridine-2-carboxamide;
8-(4-Chlorophenyl)-N-(2,2,2-trifluoroethyl)-1,6-naphthyridine-2-carboxamide;
8-(4-Chlorophenyl)-N-(3,3,3-trifluoropropyl)-1,6-naphthyridine-2-carboxamide;
8-(4-Chlorophenyl)-N-cyclopropyl-1,6-naphthyridine-2-carboxamide;
8-(4-Chlorophenyl)-N-(cyclopropylmethyl)-N-methyl-1,6-naphthyridine-2-carboxamide;
8-(4-Chlorophenyl)-N-(cyclopropylmethyl)-1,6-naphthyridine-2-carboxamide;
8-(4-Chlorophenyl)-N-neopentyl-1,6-naphthyridine-2-carboxamide;
N-tert-Butyl-8-(4-chlorophenyl)-1,6-naphthyridine-2-carboxamide;
8-(4-Chlorophenyl)-N-isopropyl-1,6-naphthyridine-2-carboxamide;
8-(4-Chlorophenyl)-N-(1-hydroxy-2-methylpropan-2-yl)-1,6-naphthyridine-2-carboxamide;
8-(4-Chlorophenyl)-N-(2-(methylsulfonyl)ethyl)-1,6-naphthyridine-2-carboxamide;
(8-(4-Chlorophenyl)-1,6-naphthyridin-2-yl)(4-methylpiperazin-1-yl)methanone;
[8-(4-Chloro-phenyl)-[1,6]naphthyridin-2-yl]-(1,1-dioxo-thiomorpholin-4-yl)-methanone;
(8-(4-Chlorophenyl)-1,6-naphthyridin-2-yl)(3-hydroxypyrrolidin-1-yl)methanone;
8-(4-Chlorophenyl)-N-(1-cyanocyclopropyl)-1,6-naphthyridine-2-carboxamide;
8-(4-Fluorophenyl)-1,6-naphthyridine-2-carboxamide;
8-(3-Fluorophenyl)-1,6-naphthyridine-2-carboxamide;
8-(2-Fluorophenyl)-1,6-naphthyridine-2-carboxamide;
8-Tolyl-1,6-naphthyridine-2-carboxamide;
8-m-Tolyl-1,6-naphthyridine-2-carboxamide;
8-o -Tolyl-1,6-naphthyridine-2-carboxamide;
8-(3,4-Difluorophenyl)-1,6-naphthyridine-2-carboxamide;
8-(3,4,5-Trifluorophenyl)-1,6-naphthyridine-2-carboxamide;
8-(4-Cyanophenyl)-1,6-naphthyridine-2-carboxamide;
8-(4-(Methylsulfonyl)phenyl)-1,6-naphthyridine-2-carboxamide;
8-(3-(Methylsulfonyl)phenyl)-1,6-naphthyridine-2-carboxamide;
8-(2-(Methylsulfonyl)phenyl)-1,6-naphthyridine-2-carboxamide;
8-(6-Methoxypyridin-3-yl)-1,6-naphthyridine-2-carboxamide;
8-(2-Methylpyridin-4-yl)-1,6-naphthyridine-2-carboxamide;
8-(Benzo[d][1,3]dioxol-5-yl)-1,6-naphthyridine-2-carboxamide;
8-(2,3-Dihydrobenzo[b][1,4]dioxin-6-yl)-1,6-naphthyridine-2-carboxamide;
8-(4-Chlorophenyl)-N-cyclopropyl-N-methyl-1,6-naphthyridine-2-carboxamide;
8-(1-Methyl-1H-pyrazol-4-yl)-1,6-naphthyridine-2-carboxamide;
8-(1-Methyl-1H-pyrazol-5-yl)-1,6-naphthyridine-2-carboxamide;
8-(3-(Methoxymethyl)phenyl)-1,6-naphthyridine-2-carboxamide;
8-(2,4-Dimethylthiazol-5-yl)-1,6-naphthyridine-2-carboxamide;
8-(4-(1H-Pyrazol-1-yl)phenyl)-1,6-naphthyridine-2-carboxamide;
8-(4-(Methoxymethyl)phenyl)-1,6-naphthyridine-2-carboxamide;
8-(4-Isopropoxyphenyl)-1,6-naphthyridine-2-carboxamide;
8-(4-(N,N-Dimethyl sulfamoyl)phenyl)-1,6-naphthyridine-2-carboxamide;
8-(4-Fluorophenyl)-N-(1-(4-(methylsulfonyl)phenyl)ethyl)-1,6-naphthyridine-2-carboxamide;
8-(2-Fluorophenyl)-N-(1-(4-(methylsulfonyl)phenyl)ethyl)-1,6-naphthyridine-2-carboxamide;
8-(3-Fluorophenyl)-N-(1-(4-(methylsulfonyl)phenyl)ethyl)-1,6-naphthyridine-2-carboxamide;
8-(2,4-Difluorophenyl)-N-(1-(4-(methylsulfonyl)phenyl)ethyl)-1,6-naphthyridine-2-carboxamide;
8-(3,4-Difluorophenyl)-N-(1-(4-(methylsulfonyl)phenyl)ethyl)-1,6-naphthyridine-2-carboxamide;
8-(2-Fluorophenyl)-N-(4-(methylsulfonyl)benzyl)-1,6-naphthyridine-2-carboxamide;
8-(3-Fluorophenyl)-N-(4-(methylsulfonyl)benzyl)-1,6-naphthyridine-2-carboxamide;
8-(2,4-Difluorophenyl)-N-(4-(methylsulfonyl)benzyl)-1,6-naphthyridine-2-carboxamide;
8-(3,4-Difluorophenyl)-N-(4-(methylsulfonyl)benzyl)-1,6-naphthyridine-2-carboxamide;
8-(2,5-Difluorophenyl)-N-(4-(methylsulfonyl)benzyl)-1,6-naphthyridine-2-carboxamide;
8-(4-Fluorophenyl)-N-neopentyl-1,6-naphthyridine-2-carboxamide;
8-(2-Fluorophenyl)-N-neopentyl-1,6-naphthyridine-2-carboxamide;
8-(3-Fluorophenyl)-N-neopentyl-1,6-naphthyridine-2-carboxamide;

8-(2,4-Difluorophenyl)-N-neopentyl-1,6-naphthyridine-2-carboxamide;
8-(3,4-Difluorophenyl)-N-neopentyl-1,6-naphthyridine-2-carboxamide;
8-(2,5-Difluorophenyl)-N-neopentyl-1,6-naphthyridine-2-carboxamide;
8-(3-Fluorophenyl)-N-(2,2,2-trifluoroethyl)-1,6-naphthyridine-2-carboxamide;
8-(4-Fluorophenyl)-N-(2,2,2-trifluoroethyl)-1,6-naphthyridine-2-carboxamide;
8-(2-Fluorophenyl)-N-(2,2,2-trifluoroethyl)-1,6-naphthyridine-2-carboxamide;
8-(2,4-Difluorophenyl)-N-(2,2,2-trifluoroethyl)-1,6-naphthyridine-2-carboxamide;
8-(3,4-Difluorophenyl)-N-(2,2,2-trifluoroethyl)-1,6-naphthyridine-2-carboxamide;
8-(2,5-Difluorophenyl)-N-(2,2,2-trifluoroethyl)-1,6-naphthyridine-2-carboxamide;
8-(2,4-Difluorophenyl)-N-(2-(methylsulfonyl)ethyl)-1,6-naphthyridine-2-carboxamide;
(8-(4-Chloro-2-fluorophenyl)-1,6-naphthyridin-2-yl)(3-hydroxypyrrolidin-1-yl)methanone;
(8-(4-Chloro-3-fluorophenyl)-1,6-naphthyridin-2-yl)(3-hydroxypyrrolidin-1-yl)methanone;
8-(4-Chlorophenyl)-N-(2-(methylsulfonyl)benzyl)-1,6-naphthyridine-2-carboxamide;
8-(2-Fluorophenyl)-N-(2-(methylsulfonyl)ethyl)-1,6-naphthyridine-2-carboxamide;
8-(3-Fluorophenyl)-N-(2-(methylsulfonyl)ethyl)-1,6-naphthyridine-2-carboxamide;
8-(4-Fluorophenyl)-N-(2-(methylsulfonyl)ethyl)-1,6-naphthyridine-2-carboxamide;
8-Isobutyl-1,6-naphthyridine-2-carboxamide;
8-(3,4-Difluorophenyl)-N-(2-(methylsulfonyl)ethyl)-1,6-naphthyridine-2-carboxamide;
8-(2,5-Difluorophenyl)-N-(2-(methylsulfonyl)ethyl)-1,6-naphthyridine-2-carboxamide;
8-(4-Chloro-2-fluorophenyl)-N-(2-(methylsulfonyl)ethyl)-1,6-naphthyridine-2-carboxamide;
8-(2-(Dimethylamino)pyridin-4-yl)-1,6-naphthyridine-2-carboxamide;
8-Morpholino-1,6-naphthyridine-2-carboxamide;
8-(4-Chlorophenyl)-N-hexyl-1,6-naphthyridine-2-carboxamide;
8-(3,6-Dihydro-2H-pyran-4-yl)-1,6-naphthyridine-2-carboxamide;
8-(4-(Hexylcarbamoyl)phenyl)-1,6-naphthyridine-2-carboxamide;
8-(3-(2-(Hexylamino)-2-oxoethyl)phenyl)-1,6-naphthyridine-2-carboxamide;
8-(4-(Heptanamidomethyl)phenyl)-1,6-naphthyridine-2-carboxamide;
8-(4-(2-(Hexylamino)-2-oxoethyl)phenyl)-1,6-naphthyridine-2-carboxamide;
8-(3-(Heptanamidomethyl)phenyl)-1,6-naphthyridine-2-carboxamide;
8-(4-Chlorophenyl)-3-methyl-1,6-naphthyridine-2-carboxamide;
8-(4-Fluorophenyl)-3-methyl-1,6-naphthyridine-2-carboxamide;
8-(4-Cyanophenyl)-3-methyl-1,6-naphthyridine-2-carboxamide;
8-(4-(Aminomethyl)phenyl)-1,6-naphthyridine-2-carboxamide;
8-(4-Chlorophenyl)-N-(2-hydroxyethyl)-1,6-naphthyridine-2-carboxamide;
8-(6-Chloropyridin-3-yl)-1,6-naphthyridine-2-carboxamide;
8-(2,4-Dichlorophenyl)-1,6-naphthyridine-2-carboxamide;
8-(4-Chlorophenyl)-N-(3-hydroxy-3-methylbutan-2-yl)-1,6-naphthyridine-2-carboxamide;
N-(3-Hydroxy-3-methylbutan-2-yl)-8-(4-(2,2,2-trifluoroethoxy)phenyl)-1,6-naphthyridine-2-carboxamide;
N-(3-Hydroxy-3-methylbutan-2-yl)-8-(3-(2,2,2-trifluoroethoxy)phenyl)-1,6-naphthyridine-2-carboxamide;
8-(4-(2,2,2-Trifluoroethoxy)phenyl)-1,6-naphthyridine-2-carboxamide;
8-(3-(2,2,2-Trifluoroethoxy)phenyl)-1,6-naphthyridine-2-carboxamide;
8-(3-Chlorophenyl)-1,6-naphthyridine-2-carboxamide;
8-(2-Chlorophenyl)-1,6-naphthyridine-2-carboxamide;
8-(4-Chloro-3-fluorophenyl)-1,6-naphthyridine-2-carboxamide;
8-(4-Chloro-3-fluorophenyl)-N-(3-hydroxy-3-methylbutan-2-yl)-1,6-naphthyridine-2-carboxamide;
8-(2-Chlorophenyl)-N-(3-hydroxy-3-methylbutan-2-yl)-1,6-naphthyridine-2-carboxamide;
8-(2,4-Dichlorophenyl)-N-(3-hydroxy-3-methylbutan-2-yl)-1,6-naphthyridine-2-carboxamide;
N-(3-Hydroxy-3-methylbutan-2-yl)-8-(3,4,5-trifluorophenyl)-1,6-naphthyridine-2-carboxamide;
8-(6-Chloropyridin-3-yl)-N-(3-hydroxy-3-methylbutan-2-yl)-1,6-naphthyridine-2-carboxamide;
8-(6-Chloropyridin-2-yl)-N-(3-hydroxy-3-methylbutan-2-yl)-1,6-naphthyridine-2-carboxamide; and,
N-(3-Hydroxy-3-methylbutan-2-yl)-8-o-tolyl-1,6-naphthyridine-2-carboxamide; or
a pharmaceutically acceptable salt thereof.

\* \* \* \* \*